(12) United States Patent
Lee

(10) Patent No.: US 10,709,750 B2
(45) Date of Patent: Jul. 14, 2020

(54) FEMALE MENOPAUSE ALLEVIATION USE OF COMPOSITION CONTAINING COMPOSITE EXTRACT OF RED CLOVER AND POMEGRANATE AS ACTIVE INGREDIENT

(71) Applicant: HLSCIENCE CO., LTD, Hwaseong-si (KR)

(72) Inventor: Hae-Yeon Lee, Uiwang-si (KR)

(73) Assignees: Hae-Yeon LEE, Gyeonggi-Do (KR); HLSCIENCE Co., LTD, Gyeonggi-Do (KR)

( * ) Notice: Subject to any disclaimer, the term of this patent is extended or adjusted under 35 U.S.C. 154(b) by 143 days.

(21) Appl. No.: 15/295,471

(22) Filed: Oct. 17, 2016

(65) Prior Publication Data

US 2018/0104296 A1    Apr. 19, 2018

Related U.S. Application Data

(63) Continuation of application No. PCT/KR2015/003895, filed on Apr. 17, 2015.

(30) Foreign Application Priority Data

Apr. 17, 2014 (KR) .................. 10-2014-0046185
Apr. 17, 2015 (KR) .................. 10-2015-0054547

(51) Int. Cl.
| | |
|---|---|
| A61K 47/46 | (2006.01) |
| A61K 31/351 | (2006.01) |
| A61K 36/48 | (2006.01) |
| A61K 31/366 | (2006.01) |
| A61K 36/185 | (2006.01) |
| A61K 31/352 | (2006.01) |
| A23L 33/105 | (2016.01) |
| A61K 31/37 | (2006.01) |

(52) U.S. Cl.
CPC ............ *A61K 36/48* (2013.01); *A23L 33/105* (2016.08); *A61K 31/352* (2013.01); *A61K 31/366* (2013.01); *A61K 31/37* (2013.01); *A61K 36/185* (2013.01); *A23V 2002/00* (2013.01); *A61K 2236/00* (2013.01)

(58) Field of Classification Search
CPC .............................. A61K 31/351; A61K 47/46
See application file for complete search history.

(56) References Cited

U.S. PATENT DOCUMENTS 7,976,880 B2    7/2011    Rajendran et al.

FOREIGN PATENT DOCUMENTS

| CN | 101205224 A | 6/2008 |
|---|---|---|
| KR | 10-2004-0101694 A | 12/2004 |
| KR | 10-0734942 B1 | 7/2007 |
| KR | 10-1272602 B1 | 6/2013 |
| WO | WO2015/160226 | * 10/2015 |

OTHER PUBLICATIONS

Kang et al. ("Dried pomegranate potentiates anti-osteoporotic and anti-obesity activities of red clover dry extracts in ovariectomized rats." Nutrients. Apr. 9, 2015;7(4):2622-47. doi: 10.3390/nu7042622). (Year: 2015).*
Lee et al. (wo2015/160226); Oct. 22, 2015. Machine Translation. (Year: 2015).*
Kim, Kyung Hu et al. The anti-climacterium effects of red clover dry extracts combined with pomegranate concentration powder in ovariectomized rats, Journal of Society of Preventive Korean Medicine 2014; (18)2: 133-145.
PCT International Preliminary Search Report for PCT/KR2015/003895, dated Jul. 30, 2015.
Markus Lipovac et al., The effect of red clover isoflavone supplementation over vasomotor and menopausal symptoms in postmenopausal women, Gynecological Endocrinology, 2011, 1-5, Early Online.
Charlotte Atkinson et al., The effects of phytoestrogen isoflavones on bone density in women; a double-blind, randomized, placebo-controlled trial 1-3, Am J Clin nutr 2004;79:326-33, Printed in U.S.A. American Society for Clinical Nutrition.
Urszula Cegiela et al., Effects of Extracts from Trifolium medium L. and Trifolium pratense L. on Development of Estrogen Deficiency-Induced Osteoporosis in Rats, Hindawi Publishing Corporation Evidence-Based Complementary and Alternative Medicine vol. 2012, Article ID 921684, 11 pages.
V Khajuria, V S Chopra, A S Raina, Dietary Supplements in Menopause, vol. 10 No. 1, Jan.-Mar. 2008.

* cited by examiner

*Primary Examiner* — Jeffrey S Lundgren
*Assistant Examiner* — Chris E Simmons
(74) *Attorney, Agent, or Firm* — Faegre Drinker Biddle & Reath LLP

(57) ABSTRACT

The present invention relates to: a natural composition containing a composite extract of pomegranates and red clover, exhibiting synergistic effects with respect to a menopausal symptom alleviation effect, an estrogen-like effect, an anti-obesity effect, a hyperlipidemia inhibitory effect, a fatty liver protective effect, an osteoporosis inhibitory effect and the like without any side effects; and various uses thereof, in particular, pharmaceutical, bromatological and cosmetic uses.

9 Claims, 38 Drawing Sheets

-A-

-B-

-C-

-D-

-E-

-F-

-G-

-H-

-I-

-J-

-K-

-L-

-M-

-N-

FEMALE MENOPAUSE ALLEVIATION USE OF COMPOSITION CONTAINING COMPOSITE EXTRACT OF RED CLOVER AND POMEGRANATE AS ACTIVE INGREDIENT

TECHNICAL FIELD

The present disclosure relates to a natural composition showing an outstanding effect in a variety of applications, and more particularly, to a natural plant composite extract showing an outstanding effect in relieving menopausal symptoms.

The present application claims priority to Korean Patent Application No. 10-2014-0046185 filed in the Republic of Korea on Apr. 17, 2014 and Korean Patent Application No. 10-2015-0054547 filed in the Republic of Korea on Apr. 17, 2015, the disclosures of which are incorporated herein by reference.

BACKGROUND ART

Estrogen shows an essential modulation effect on various organs in women including the uterus, vagina, skeletal muscles and cardiovascular system, and is primarily responsible for catabolism and activation [Couse and Korach, 1999; Korach et al., 1995]. Thus, estrogen deprivation in women at the menopause causes a variety of medical symptoms called menopausal disorders [Turner et al., 1994; Versi et al., 2001].

A menopausal disorder is a term that refers collectively to various symptoms caused by a sharp reduction of a female hormone (estrogen) in women at the menopause [Dennerstein et al., 2002; Wolff et al., 2006]. To reduce menopausal disorders, hormone therapy has been used to supplement the declining level of female hormones [Greendale et al., 1998; Nichols et al., 1984], but its long-term use causes various adverse effects such as uterus cancer, breast cancer, stroke and pulmonary embolism [Han et al., 2002; Beral et al., 2005; Kaari et al., 2006], so recently, plant-derived phytoestrogens are gaining attention [Knight and Eden, 1996; Setchell, 1998; del Giorno et al., 2010; Ateba et al., 2013]. Phytoestrogens are structurally similar to estrogen so that they can bind to estrogen receptor ER-alpha and ER-beta [Akiyama et al., 1987; Kuiper et al., 1997; Cornwell et al., 2004], showing a weak estrogen-like effect [Kuiper et al., 1997], and they are known as showing an effect on inhibition of various metabolic syndromes in women at the menopause [Taku et al., 2007] as well as a relatively good effect on preservation of bone mass [Ma et al., 2008]. It is known that estrogen deprivation causes significant atrophy of female reproductive organs such as uterus and vagina [Versi et al., 2001; Ateba et al., 2013], and estrogen deficiency induced by OVX also causes significant endometrial atrophy [Kawakita et al., 2009; Ateba et al., 2013].

Osteoporosis is a disorder of bone remodeling characterized by higher bone resorption than bone formation, and a metabolic disease that leads to disorders of mineral metabolism in bodies and drastically increased fractures [Sakai et al., 1998], and particularly, fractures near the hip joint cause so serious problems that threaten lives [Yamaguchi et al., 1999]. OVX rats show extremely similar signs to osteoporosis that develops after women's menopause over 4-6 weeks after operation, and have been very usefully used to develop osteoporosis medicines or bone protective materials [Kalu, 1991; Wronski et al., 1991; Frost and Jee, 1992], and particularly, US Food and Drug Administration suggests OVX rats as an essential animal model to investigate the efficacy in developing osteoporosis medicines [US Food and Drug Administration, 1994]. Reductions in bone weight are directly linked to bone mineral loss caused by the development of osteoporosis [Yamamoto et al., 1998], and particularly, inhibition of ash bone weight reduction is used as a direct evidence showing a treatment effect for osteoporosis [Puel et al., 2005; Xie et al., 2005]. Osteocalcin is used as a typical bone turnover marker, and bALP level is known as a typical bone formation marker in serum [Ke et al., 2004; Rissanen et al., 2008; Yang et al., 2011; Kuo et al., 2012]. Generally, as osteoporosis develops, serum osteocalcin levels increase due to increased bone turnover, serum bALP levels remarkably reduce by inhibition of bone formation [Ismail et al., 1988; Ederveen and Kloosterboer, 1999; Rissanen et al., 2008; Yang et al., 2011; Kuo et al., 2012]. BMD and bone strength are important indices showing the quality of bone, and it is known that osteoporosis causes remarkable reductions in bone mineral density and bone strength regardless of causes [Bilston et al., 2002; Diez, 2002; Syed and Khan, 2002]. A histology test provides most accurate morphological information of bone [Yamaguchi et al., 1999; Heikkinen et al., 2004], and as osteoporosis develops, histomorphometrical indices related to bone mass and bone formation remarkably reduce, and factors related to bone resorption increase [Heikkinen et al., 2004; Jakubas-Przewlocka et al., 2005]. Because remarkable reductions in bone mass and structure and increases in bone resorption activity are histologically confirmed in OVX rats, a histology test of bone always provided a direct efficacy evaluation criterion [Glatt et al., 2004; Jakubas-Przewlocka et al., 2005].

DISCLOSURE

Technical Problem

Therefore, the present disclosure is directed to providing a natural composition including a composite extract of pomegranate and red clover that exerts a synergistic effect for the relief of menopausal symptoms without any adverse effect, and its use in a wide range of applications, in particular, drugs, foods, and cosmetics.

Technical Solution

To achieve the object, the present disclosure provides a composition including a composite extract of pomegranate and red clover as an active ingredient.

In an embodiment, the present disclosure provides a composition for reducing a menopausal disorder including a composite extract of pomegranate and red clover as an active ingredient.

Furthermore, the present disclosure provides a method for reducing a menopausal disorder, including the step of administering a composition including a composite extract of pomegranate and red clover as an active ingredient to a subject in need thereof.

Furthermore, the present disclosure provides use of a composite extract of pomegranate and red clover for preparing a composition for reducing a menopausal disorder.

In the present disclosure, hereinafter, it should be understood that the description of 'the composition for reducing a menopausal disorder including a composite extract of pomegranate and red clover as an active ingredient' is equally applied to 'the method for reducing a menopausal disorder, including the step of administering a composition including a composite extract of pomegranate and red clover as an active ingredient to a subject in need thereof' and 'the use of a composite extract of pomegranate and red clover for preparing a composition for reducing a menopausal disorder' to avoid repetition in the description.

Red clover, *Trifolium pratense* L, is a perennial herb in the beam family, and is also called Beebread, Cow clover, Cow grass, Meadow clover, or Purple clover. Red clover is a plant with an erect growth habit that has its origin in the Caribbean Territories and Southeast Asia, and is cultivated and grows widely all over the world. Red clover is used for forage, and young leaves can be eaten cooked in the spring. Red clover is known as having effectiveness in treating cough or asthma because of expectorating action.

Red clover can be divided into aerial parts and root, and the present disclosure may preferably use an aerial part extract of red clover, but is not limited thereto.

In another embodiment, preferably the red clover extract may be obtained by extraction using water, lower alcohol with 1-4 carbons, or mixtures thereof as a solvent.

The red clover extract according to the present disclosure may be prepared by the following method. For example, the red clover extract may be prepared by cleaning red clover first, then separating red clover aerial parts, and extracting at 60° C.-90° C. and 0.01-0.5 MPa for 1-4 hours 1-5 times with an addition of, preferably, water, lower alcohol with 1-4 carbons, or mixtures thereof as a solvent, but the present disclosure is not limited thereto.

In another embodiment, the composition of the present disclosure may preferably provide a composition including 50-150 mg/g of isoflavone in relation to the total red clover extract, but is not limited thereto.

Pomegranate, *Punica granatum* L, is a plant that grows naturally in Southwest Asia, India's northwest province and California, U.S.A, and is now widely cultivated in subtropical and tropical regions. From ancient times, pomegranate, in particular, red pomegranate, has been known as a tonic medicinal material, and particularly, are known to be very effective in preventing hypertension and arteriosclerosis. Also, pomegranate includes water-soluble carbohydrates in amounts as large as 38 to 47% and various types of vitamins and minerals.

Pomegranate used in the present disclosure is not limited to a particular type, but red pomegranate is preferred. Specific examples of red pomegranate include those from Iran, California, Taiwan, Uzbekistan, Turkey and Korea. The pomegranate extract according to the present disclosure may vary depending on production areas and harvest times of pomegranates used.

The present disclosure provides an extract using pomegranate pulps alone without containing pomegranate pericarps and seeds. The pomegranate pericarps and seeds may cause adverse effects, and for example, a particular alkaloid contained in the pomegranate pericarps degrades the physical functions and negatively affects the respiratory system and muscles, and addiction to alkaloid induces seizures, convulsion, and narcosis. Also, an extract from the pomegranate seeds has adverse effects, and for example, an allergic reaction such as tongue swelling may appear in some people after intake.

The pomegranate extract according to the present disclosure may be prepared by the following method. For example, first, after cleaning pomegranates, pericarps and seeds are completely removed from the pomegranates, and enzyme such as pectinase, proteinase, amylase, and cellulase is added to degrade polysaccharides, such as starch, present in the pomegranates. Subsequently, optionally, an additive such as gelatin, silicon dioxide, bentonite, silicasol, tannin, cellulose, and potassium caseinate is added to control the turbidity, color, and viscosity of the pomegranate extract, followed by concentration by heating, to produce a pomegranate extract, but the present disclosure is not limited thereto.

In another embodiment, the pomegranate extract of the present disclosure may preferably include 0.5-1 mg/g of ellagic acid in relation to the total pomegranate extract, but is not limited thereto.

The composition for reducing a menopausal disorder including the composite extract of pomegranate and red clover of the present disclosure as an active ingredient shows a superior effect to a menopausal disorder reduction effect of a pomegranate extract alone or a red clover extract alone, and thus, it shows an outstanding effect even in a small dose. The present disclosure is not limited in this regard, but preferably, a weight ratio of the red clover extract to the pomegranate extract may be 1:1-4, and more preferably, the weight ratio of the red clover extract to the pomegranate extract may be 1:1.5-2.5. Even more preferably, the weight ratio of the red clover extract to the pomegranate extract may be 1:2.

In another embodiment, the present disclosure preferably contains 50-150 mg of the composite extract of pomegranate and red clover per 100 ml of the composition.

In another embodiment, preferably the composite extract of pomegranate and red clover may include 30-100 mg/g of isoflavone and 0.15-0.4 mg/g of ellagic acid, and more preferably, the composite extract of pomegranate and red clover may include 50-70 mg/g of isoflavone and 0.2-0.3 mg/g of ellagic acid.

In another embodiment, preferably, the composition is provided wherein the menopausal disorder shows at least one menopausal symptom selected from the group consisting of facial flushing, sweating, insomnia, nervousness, depression, dizziness, poor concentration, arthralgia, headache, tachycardia, vaginal dryness, fatigue, excitement, sleeplessness, memory loss, anxiety and atherosclerosis.

In the present disclosure, the menopausal disorder refers to facial flushing, sweating, insomnia, nervousness, depression, dizziness, poor concentration, arthralgia, headache, tachycardia, vaginal dryness, fatigue, excitement, sleeplessness, memory loss, anxiety or atherosclerosis, but is not limited thereto.

In another embodiment, preferably, the menopausal disorder reduction may show at least one effect selected from the group consisting of menopausal symptom relief, anti-obesity, hyperlipidemia inhibition, fatty liver inhibition, osteoporosis inhibition, liver protection and uterus protection.

In another embodiment, the present disclosure provides a pharmaceutical composition including any one of the compositions.

The pharmaceutical composition according to the present disclosure may include a pharmaceutically effect amount of the composite extract of pomegranate and red clover alone, or additionally include at least one pharmaceutically acceptable carrier, excipient or diluent. The "pharmaceutically acceptable" refers to a non-toxic composition that is physiologically acceptable, and when administered to humans, does not inhibit the action of an active ingredient, and generally does not cause any allergic response such as stomach disorders and dizziness or similar responses.

Examples of the carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methylcellulose, polyvinylpyrrolidone, water, methylhydroxybenzoate, propylhydroxybenzoate, talc, magnesium stearate and mineral oil. Also, the pharmaceutical composition may additionally include fillers, anticoagulants, lubricants, wetting agents, flavorings, emulsifiers or preservatives.

The term "pharmaceutically effective amount" as used herein refers to an amount that shows greater responses than negative control, and preferably an amount sufficient to show an effect on the prevention and/or treatment of menopausal disorders.

Furthermore, the pharmaceutical composition of the present disclosure may be formulated by known methods in the art to provide rapid, sustained or delayed releases of the active ingredient after it is administered to mammals. The formulation may be in the form of powders, granules, tablets, emulsions, syrups, aerosols, soft or hard gelatin capsules, sterile solutions for injection, and sterile powders.

The pharmaceutical composition of the present disclosure is not limited to a particular administration route, but may be orally or non-orally administered. The non-oral administration route may include many routes such as, for example, percutaneous, nasal, intraperitoneal, intramuscular, subcutaneous or intravenous routes.

Furthermore, the pharmaceutical composition of the present disclosure may be administered in conjunction with known compounds having an effect on the prevention and/or treatment of menopausal disorders.

In another embodiment, the present disclosure provides a food composition including any one of the compositions.

The food composition of the present disclosure includes all processing types of natural materials such as foods, functional foods, nutritional supplements, health foods and food additives. Such type of food composition may be prepared in various types by common methods known in the art.

For example, the health food can be eaten by preparing the composite extract of pomegranate and red clover itself in the form of teas, juices and drinks, or by granulating, capsulating or pulverizing it. Also, in addition to the composite extract of pomegranate and red clover of the present disclosure, the health food may additionally include *Paeonia japonica*, *Cornus oficinalis*, *Acanthopanax senticosus*, *Ganoderma lucidium*, the stem bark of *Fraxinus rhynchophylla*, *Eucommia ulmoides*, *Angelica giga*, *Gardenia jasminoides*, *Astragalus membranaceus*, malt, trifoliate orange, vitamin C, fructooligosaccharides, stevioside, purified water, and maltodextrin singly or in combination without detracting from the purpose of the present disclosure, but other medicinal ingredients and/or additives that may be additionally included in the food composition of the present disclosure are not limited to the examples.

For example, the food composition according to the present disclosure may include water-soluble vitamins such as thiamine (vitamin BI), riboflavin, ascorbic acid, niacin, and vitamin B6, fatty acids such as myristic acid, palmitic acid, stearic acid, oleic acid, and linoleic acid, weak acids such as glycolic acid and acetic acid, and amino acids such as eight essential amino acids including threonine, valine, methionine, isoleucine, leucine, phenylalanine, tryptophan and lysine, as well as aspartic acid, serine, glutamic acid, proline, glycine, alanine, cysteine, tyrosine, histidine, and arginine.

In another embodiment, the present disclosure provides a cosmetic composition including any one of the compositions.

Ingredients included in the cosmetic composition of the present disclosure include not only the composite extract of pomegranate and red clover but also ingredients commonly used for cosmetic compositions as active ingredients, and for example, include general adjuvants such as antioxidants, stabilizers, solubilizers, vitamins, pigments and flavorings, and carriers.

The cosmetic composition according to the present disclosure may be prepared in any formulation commonly prepared in the art. For example, the cosmetic composition may be formulated as solutions, suspensions, emulsions, pastes, gels, creams, lotions, powders, soaps, surfactant-containing cleansings, oils, powdery foundations, emulsion foundations, wax foundations and sprays, but is not limited thereto.

More specifically, the cosmetic composition may be prepared in formulation of softening toner, nourishing toner, nourishing cream, massage cream, essence, eye cream, cleansing cream, cleansing foam, cleansing water, pack, spray or powder.

In case that the formulation of the present disclosure is a solution or an emulsion, the carrier substance is a solvent, a solubilizer or a suspending agent, and for example, is water, ethanol, isopropanol, ethyl carbonate, ethyl acetate, benzyl alcohol, benzyl benzoate, propyleneglycol, 1,3-butylglycol oil, glycerol aliphatic ester, polyethylene glycol or sorbitan fatty acid ester.

In case that the formulation of the present disclosure is a suspension, the carrier substance may be a liquid diluent such as water, ethanol or propylene glycol, a suspending agent such as isostearyl alcohol ethoxylated, polyoxyethylene sorbitol ester and polyoxyethylene sorbitan ester, microcrystalline cellulose, aluminum metahydroxide, bentonite, agar or tragacanth.

In case that the formulation of the present disclosure is a surfactant-containing cleansing, the carrier substance may be aliphatic alcohol sulfate, aliphatic alcohol ether sulfate, sulfosuccinate monoester, isethionate, imidazolium derivatives, methyltaurate, sarcosinate, fatty acid amide ether sulfate, alkylamidobetaine, aliphatic alcohol, fatty acid glyceride, fatty acid diethanolamide, vegetable oil, lanolin derivatives or glycerol fatty acid ester ethoxylated.

In case that the formulation of the present disclosure is a powder or a spray, the carrier substance may be lactose, talc, silica, aluminum hydroxide, calcium silicate, or polyamide powder, and particularly, in the case of a spray, the carrier substance may additionally include a propellant such as chloro fluorohydrocarbon, propane/butane or dimethyl ether.

In case that the formulation of the present disclosure is a paste, a cream or a gel, the carrier substance may be animal oil, vegetable oil, wax, paraffin, starch, tragacanth, cellulose derivatives, polyethylene glycol, silicone, bentonite, silica, talc or zinc oxide.

In another embodiment, preferably the red clover extract may be a red clover extract powder.

In another embodiment, preferably the pomegranate extract may be a pomegranate extract powder.

The term "powder" as used herein refers to, for example, freeze dried powder or dehydrated powder, but is not limited thereto.

In another embodiment, the present disclosure provides a method for improving a menopausal disorder reduction effect, including mixing a red clover extract with a pomegranate extract at a weight ratio of the red clover extract to the pomegranate extract of 1:1-4, preferably mixing a red clover extract with a pomegranate extract at a weight ratio of the red clover extract to the pomegranate extract of 1:1.5-2.5, and more preferably mixing a red clover extract with a pomegranate extract at a weight ratio of the red clover extract to the pomegranate extract of 1:2.

In another embodiment, the present disclosure provides a method for preparing a composite extract of pomegranate and red clover for relieving menopausal symptoms, including the steps of S1) adding starch degrading enzymes to pomegranate pulps, followed by concentration by heating, to prepare a pomegranate pulp extract; (S2) adding water, lower alcohol with 1-4 carbons, or mixtures thereof as a solvent to red clover aerial parts, to prepare a red clover aerial part extract; and (S3) mixing the pomegranate pulp extract with the red clover aerial part extract and stirring.

In the present disclosure, the starch degrading enzymes at the step S1) may include, but are not limited to, for example, enzymes such as pectinase, proteinase, amylase and cellulase.

In another embodiment, preferably, the method for preparing a composite extract of pomegranate and red clover for relieving menopausal symptoms is provided wherein the method further includes heating the red clover aerial part extract to bring it to a concentrate, drying with the addition of polysaccharides, and mixing as a red clover aerial part extract powder at the step (S3).

In another embodiment, preferably, the method for preparing a composite extract of pomegranate and red clover for relieving menopausal symptoms is provided wherein the method further includes drying the pomegranate pulp extract with the addition of polysaccharides and mixing as a pomegranate pulp extract powder at the step (S3).

Advantageous Effects

According to the present disclosure, there is provided a natural composition including a composite extract of pomegranate and red clover that exerts a synergistic menopausal symptom relief effect showing at least one effect selected from the group consisting of menopausal symptom relief, anti-obesity, hyperlipidemia inhibition, fatty liver inhibition, osteoporosis inhibition, liver protection and uterus protection, without any adverse effect.

BEST MODE FOR CARRYING OUT THE INVENTION

Figure 1:
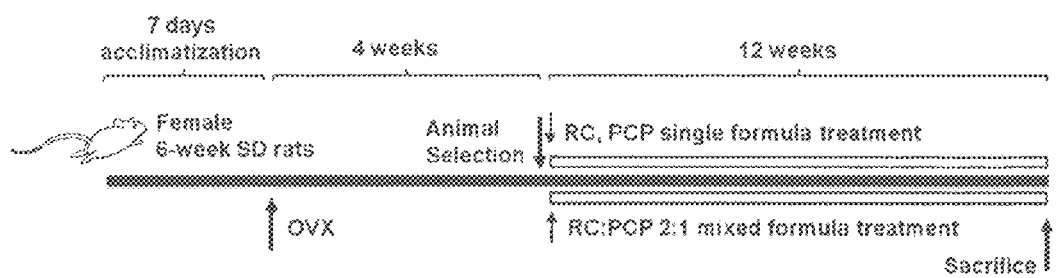
FIG. 1 shows a test schedule for testing a synergistic effect of a mixture including a red clover extract and a pomegranate extract using OVX rats.
Figure 2:
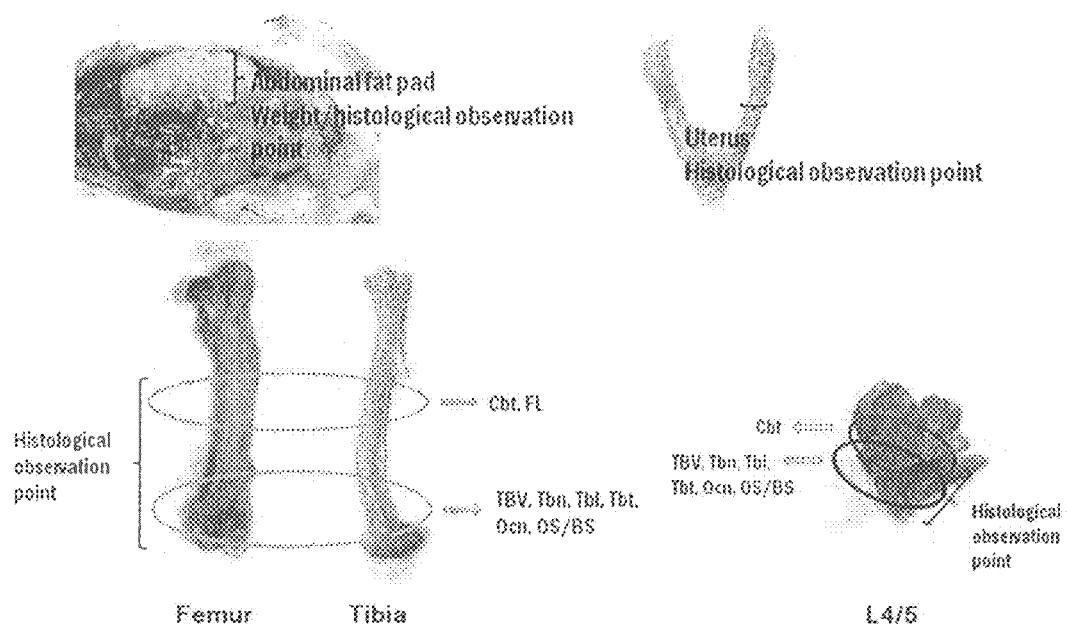
FIG. 2 shows rat regions in which histopathological changes are observed.

Hereinafter, the present disclosure will be explained in detail with reference to preparation examples and working examples to help the understanding of the present disclosure. However, the preparation examples and working examples according to the present disclosure may be modified in a variety of different forms and should not be construed as limiting the scope of the present disclosure. The preparation examples and working examples of the present disclosure are provided to explain the present disclosure more fully to those having ordinary knowledge in the art to which the present disclosure pertains.

0. Method for Preparing a Mixture Including a Red Clover Extract and a Pomegranate Extract (1) Preparation of a Red Clover Extract Red clover was cleaned first. Aerial parts were only separated from red clover and 80-120 kg red clover aerial parts in total weight were prepared. 70% ethanol was added in weight about 3 times larger than the weight of red clover, and extraction was performed at 75° C.-80° C. and 0.05 MPa for 2.5 hrs 2~3 times, yielding 300 kg red clover extract. 100 mesh filtration followed separation through a solid/liquid separation process. The filtered red clover extract was heated at 70° C. and 0.06 Mpa for 6 hours to bring it to a concentrate, yielding 25 kg red clover concentrate extract. The concentrate was spray dried with the addition of 0-1 kg maltodextrin and passed through 8 mesh, yielding 10 kg red clover extract powder containing 10% isoflavone.

(2) Preparation of a Pomegranate Extract

After removing stains from 1000 kg pomegranates, spoiled fruits were sorted out, followed by cleaning. The pomegranate fruits left after sorting were cut to remove pericarps and pressed to deseed, yielding 450 kg pomegranate pulp. After filtration, sterilization at 100-105° C. for 60 seconds, and cooling at 48-55° C. was performed. Amylolysis was performed at 48-55° C. for 30 minutes with the addition of 70~100 ml pectinase per 1000 L pomegranate juice. Subsequently, for good eating viscosity with maintaining turbidity and color, 900 g bentonite per 10000 L pomegranate juice was fed, and stirred at 48-55° C. for 10 minutes. Subsequently, 1.5 mm and 1 mm vacuum filtration and concentration by heating (at 80° C. under 475 mbar to 12 brix, at 87° C. under 626 mbar to 17 brix, at 95° C. under 847 mbar to 31 Brix, at 70° C. under 312 mbar to 43 Brix and at 49° C. under 118 mbar to 65 Brix in a sequential order) was performed, followed by 0.15 mm filtration, yielding a liquid pomegranate concentrate containing 1.8~3.0 mg/g ellagic acid. Subsequently, the liquid pomegranate concentrate was mixed with dextrin and gone through a spray drying process to produce pomegranate concentrate powder containing 0.5~1.0 mg/g ellagic acid.

(3) Preparation of a Composite Extract of Red Clover and Pomegranate 40 kg the prepared red clover extract powder (containing 10% isoflavone) and 20 kg the prepared pomegranate extract powder (containing 0.8 mg/g ellagic acid) were mixed and stirred, yielding 60 kg a final composite extract of red clover and pomegranate (containing 66.7 mg/g isoflavone and 0.26 mg/g ellagic acid).

1. Effect of a Combination of a Red Clover Extract and a Pomegranate Extract

An experiment was designed with expectation of a remarkable synergistic effect of diversity of isoflavonoid content at a particular mixture ratio of a red clover extract and a pomegranate extract.

In the study, with the addition of a pomegranate extract, an effect of magnified biological activity of a red clover extract on menopausal disorders was evaluated using ovariectomy (OVX) rat model. That is, from 28 days after OVX, red clover extract:pomegranate extract 2:1 (g/g) mixture 120 mg/kg and 60 mg/kg were dissolved in or diluted with sterile distilled water and orally administered at a dose of 5 ml/kg once daily for 84 days (12 weeks; 3 months), and evaluation was conducted based on 5 pharmacological effects including an estrogen-like effect, an anti-obesity effect, a hyperlipidemia inhibitory effect, a protective effect against fatty liver and an osteoporosis inhibitory effect.

Figure 3:
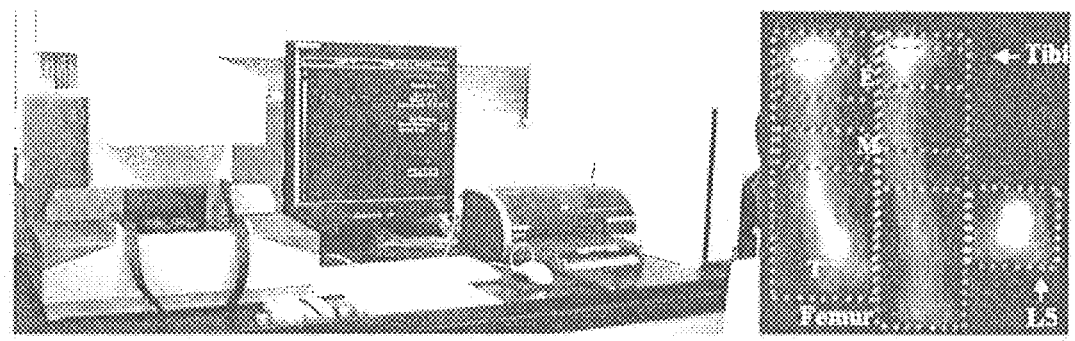
FIG. 3 shows a bone mineral density (BMD) measuring apparatus (left side), and total (T), epiphyseal (E) and diaphyseal (mid-shaft; M) regions of right femur, tibia and L5 total region detected by dual-energy x-ray absorptiometry (Norland pDEXA; Fort Atkinson, Wis., USA) (right side).
Figure 4:
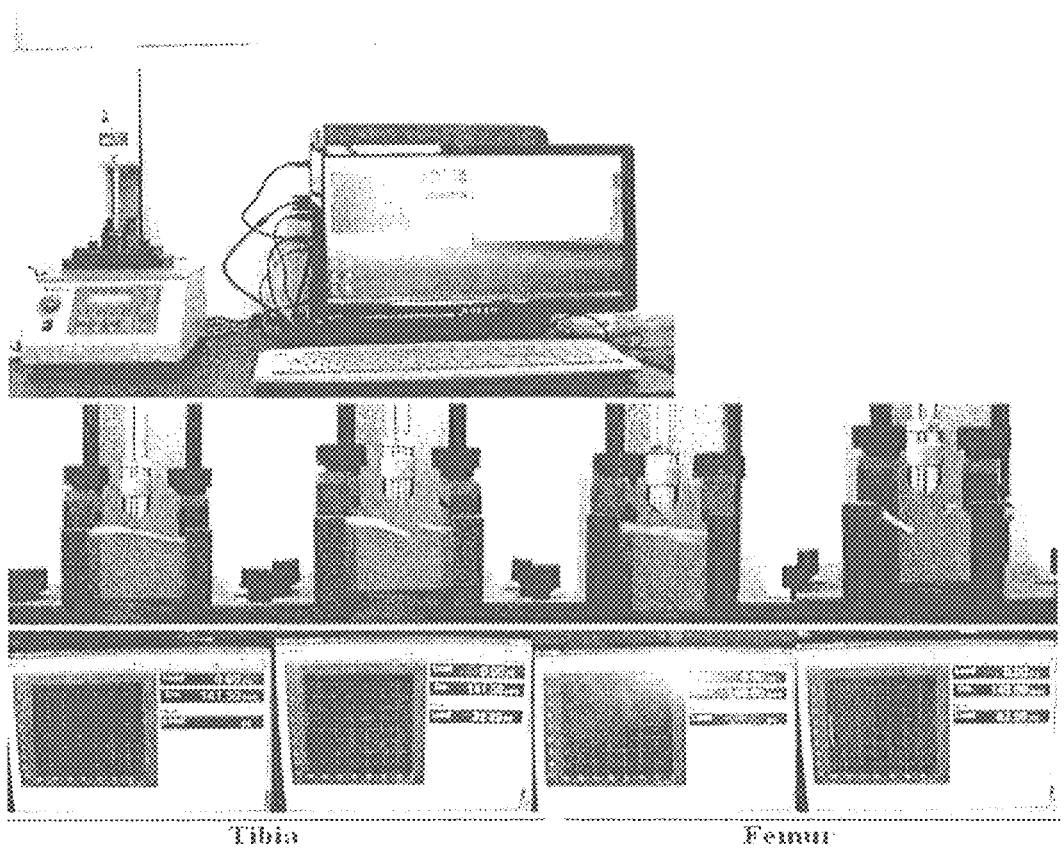
FIG. 4 shows a bone strength measuring apparatus. Bone strength is measured through failure load (FL).

To evaluate the estrogen-like effect and the anti-obesity effect, changes in body weight and body weight gain, water and food consumption, urine volume and fecal excretion, serum estradiol level, and weight of abdominal fat pad and uterus, and changes in abdominal fat pad thickness and mean adipocyte diameter, thickness of uterus total, epithelium and mucosa, and percentage of uterine glands in the mucosa were each evaluated. Furthermore, the liver protective effect against fatty liver was evaluated by measuring changes in liver weight, serum Aspartate aminotransferase (AST) and Alanine aminotransferase (ALT) levels, mean hepatocyte diameter and region with hepatic degeneration showing fatty change, and the hyperlipidemia reduction effect was evaluated using changes in serum total cholesterol (TC), low-density lipoprotein (LDL), high-density lipoprotein (HDL) and triglyceride (TG) levels, and to evaluate the osteoporosis reduction effect, namely, the bone protective effect, histological changes in wet, dry and ash weights of femur, tibia and lumbar vertebrae, bone mineral density (BMD) (FIG. 3), bone strength (FIG. 4), serum osteocalcin level and bone specific alkaline phosphatase (bALP) levels, bone mass and structure, and bone resorption were each measured. In the experiment, evaluation was conducted by comparing the results of red clover:pomegranate extract 2:1 (g/g) mixture to the results in rats administered with each of red clover extract 40 mg/kg and pomegranate extract 20 mg/kg.

Example 1-1. Experimental Animal and Experimental Method (1) Experimental Animal Female virgin Sprague-Dawley Rats (6 weeks old, OrientBio, Seungnam, Korea) were used, and in the experiment, all experimental animals were handled according to the guidelines for animal ethics approved by the Animal Care and Ethics Committee of Daegu Haany University, and the experiment was performed with prior approval [Approval No. DHU2013-042].

(2) Experimental Method

The experiment was performed after dividing the experimental animals into groups (total 7 groups; 8 mice per group) (Table 1, FIG. 1).

That is, the experiment was performed after dividing into sham control, OVX control, red clover dry extract single formula 40 mg/kg administered group after OVX surgery, pomegranate extract single formula 20 mg/kg administered group after OVX surgery, red clover:pomegranate extract 2:1 (g/g) mixed formula 120 mg/kg administered group after OVX surgery, and red clover:pomegranate extract 2:1 (g/g) mixed formula 60 mg/kg administered group after OVX surgery.

Optimal amounts of red clover extract, pomegranate extract or red clover:pomegranate extract 2:1 (g/g) mixture were suspended or dissolved in sterile distilled water, and orally administered at a dose of 5 ml/kg once daily for 84 days from 28 days after OVX. That is, red clover extract 40 mg/kg, pomegranate extract 20 mg/kg, red clover:pomegranate extract 2:1 (g/g) mixture 120 and 60 mg/kg were each orally administered for 84 days, and in sham control and OVX control, only sterile distilled water as a vehicle was orally administered at the same dose for the same duration, instead of the test material (Table 1).

TABLE 1

| Group | Operation | Dose (mg/kg/day) | Animal No. |
|---|---|---|---|
| Anti-climacterium Effect of RC:PCP 2:1 Mixtures (g/g) | | | |
| Control | Sham operate | Vehicle, distilled water 5 ml/kg | R01~R08 |
| Control | OVX operate | Vehicle, distilled water 5 ml/kg | R09~R16 |
| Reference | OVX operate | RC 40 mg/kg | R17~R24 |
| Reference | OVX operate | PCP 20 mg/kg | R25~R32 |
| Active | OVX operate | RC:PCP 2:1 mixtures (g/g) 120 mg/kg | R33~R40 |
| Active | OVX operate | RC:PCP 2:1 mixtures (g/g) 60 mg/kg | R41~R48 |

OVX = Bilateral ovariectomy
PCP = Pomegranate Concentrate Powder
RC = Red clover dry extracts For induction of menopausal disorders by OVX, an experiment was performed as follows.

That is, all experimental animals except sham control were randomly selected and underwent bilateral ovariectomy to induce osteoporosis. On the other hand, in sham operated group, both ovaries were detected by the same method but incisions were not made, and abdominal cavities were closed again. At 28 days after surgery, based on body weights (OVX rats: 323.81±4.77 g, 304-354 g; sham operated rats: 253.25±9.08 g, 240-265 g), 8 mice per group were selected from all the experimental animals including shame operated group and used for experiments.

The effect on menopausal disorders was evaluated based on 5 pharmacological effects including an estrogen-like effect, an anti-obesity effect, a hyperlipidemia inhibitory effect, a protective effect against fatty live and an osteoporosis inhibitory effect.

More specifically, the anti-obesity and estrogen-like effects were tested as follows. The body weights on the date of OVX surgery, 1 day before administration (27 days after OVX), the date of start of administration, and at least once a week from 1 day after start of administration to the date of final sacrifice were each recorded, and change amounts of body weight, i.e., body weight gains for the recovery period after OVX (menopausal disorder induction period) and 12 weeks after start of administration were measured. The water and food consumption, urine volume and fecal excretion (28, 49 and 83 days after start of administration), serum estradiol level, weight of abdominal fat pad and uterus, and histopathological changes in uterus and abdominal fat pad (changes in abdominal fat pad thickness and mean adipocyte diameter, thickness of uterus total, epithelium and mucosa, and percentage of uterine glands in the mucosa) were observed.

Furthermore, to ascertain the protective effect against fatty liver, an experiment was performed as follows. Liver weight, serum AST and ALT levels, and histological changes of liver (changes in mean hepatocyte diameter and region with hepatic degeneration showing fatty change) were observed.

The hyperlipidemia inhibitory effect was ascertained through changes in serum TC, LDL, HDL and TG levels.

The osteoporosis reduction effect was ascertained through histological changes in wet, dry and ash weights of femur, tibia and lumbar vertebrae, BMD (FIG. 3), bone strength, serum osteocalcin and bALP levels, bone mass and structure (trabecular bone mass, trabecular bone number, thickness and length, and cortical bone thickness) and bone resorption (osteoclast cell number and osteoclast cell surface (OS/BS)).

Example 1-2. Change in Body Weight and Body Weight Gain

At 28 days after OVX surgery, as compared to sham control, only experimental animals showing remarkable increases in body weight were selected and used (OVX rats: 323.81±14.77 g, 304-354 g; sham operated rats: 253.25±9.08 g, 240-265 g), and significant ($p<0.01$) increases in body weight and body weight gain for a 4 week-induction period after OVX were found in all OVX operated groups as compared to sham control, but red clover:pomegranate extract 2:1 (g/g) mixture 120 mg/kg administered group started to show significant ($p<0.01$ or $p<0.05$) decreases in body weight 49 days after start of administration as compared to OVX control, and red clover:pomegranate extract 2:1 (g/g) mixture 60 mg/kg administered group started to show significant ($p<0.01$ or $p<0.05$) decreases in body weight 56, 63 and 70 days after start of administration respectively as compared to OVX control. Furthermore, all test substance administered groups also showed significant ($p<0.01$) decreases in body weight gain for the duration of administration of 84 days as compared to OVX control. Particularly, red clover:pomegranate extract 2:1 (g/g) mixture 120 mg/kg administered group showed significant ($p<0.01$ or $p<0.05$) decreases in body weight 77 days after start of administration as compared to each of red clover extract 40 mg/kg and pomegranate extract 20 mg/kg administered group, and red clover:pomegranate extract 2:1 (g/g) mixture 120 and 60 mg/kg administered group also showed significant ($p<0.01$) decreases in body weight gain for the duration of administration of 84 days as compared to each of red clover extract 40 mg/kg and pomegranate extract 20 mg/kg administered group (Table 2).

TABLE 2

| | Body weights (g) | | | | Body weight gains (g) | |
|---|---|---|---|---|---|---|
| Groups | At OVX [A]* | At 27 days after OVX [B] | At first treatment [C]* | At sacrifice [D]* | OVX recovery [B − A] | Treatment [D − C] |
| Controls | | | | | | |
| Sham | 157.88 ± 4.73 | 253.25 ± 9.08 | 234.88 ± 8.41 | 314.50 ± 23.63 | 95.83 ± 9.04 | 79.63 ± 20.98 |
| OVX | 159.13 ± 8.01 | 323.88 ± 17.13$^a$ | 298.75 ± 13.33$^a$ | 455.25 ± 20.95$^a$ | 164.75 ± 15.68$^a$ | 156.50 ± 16.27$^e$ |
| RC 40 mg/kg | 158.38 ± 7.80 | 320.75 ± 8.88$^a$ | 296.00 ± 11.31$^a$ | 415.50 ± 13.56$^{ab}$ | 162.38 ± 7.07$^a$ | 119.50 ± 6.50$^{ef}$ |
| PCP 20 mg/kg | 156.38 ± 4.41 | 324.13 ± 15.99$^a$ | 298.38 ± 13.26$^a$ | 418.88 ± 15.12$^{ab}$ | 167.75 ± 14.61$^a$ | 120.50 ± 8.47$^{ef}$ |

TABLE 2-continued

| | Body weights (g) | | | | Body weight gains (g) | |
|---|---|---|---|---|---|---|
| Groups | At OVX [A]* | At 27 days after OVX [B] | At first treatment [C]* | At sacrifice [D]* | OVX recovery [B − A] | Treatment [D − C] |
| | | | RC:PCP 2:1 mixture (g/g) | | | |
| 120 mg/kg | 157.88 ± 6.83 | 323.50 ± 15.69$^a$ | 299.38 ± 14.68$^a$ | 395.00 ± 9.07$^{abcd}$ | 165.63 ± 12.33$^a$ | 95.63 ± 9.27$^{efgh}$ |
| 60 mg/kg | 157.25 ± 7.30 | 327.63 ± 17.94$^a$ | 301.00 ± 16.78$^a$ | 407.63 ± 18.05$^{ab}$ | 170.38 ± 14.32$^a$ | 106.63 ± 8.75$^{efgh}$ |

*All animals were fasted overnight.
$^a$p < 0.01: comparison with sham control according to LSD test
$^b$p < 0.01: comparison with OVX control according to LSD test
$^c$p < 0.05: comparison with red clover extract 40 mg/kg administered group according to LSD test
$^d$p < 0.01: comparison with pomegranate extract 20 mg/kg administered group according to LSD test
$^e$p < 0.01: comparison with sham control according to MW test
$^f$p < 0.01: comparison with OVX control according to MW test
$^g$p < 0.01: comparison with red clover extract 40 mg/kg administered group according to MW test
$^h$p < 0.01: comparison with pomegranate extract 20 mg/kg administered group according to MW test In the case of OVX control, the body weight gain for the duration of administration changed by 96.55% as compared to sham control, and red clover extract 40 mg/kg, pomegranate extract 20 mg/kg, red clover:pomegranate extract 2:1 (g/g) mixture 120, 60/kg administered groups had changes by −5.60, −6.48, −8.86, −3.17% respectively 28 days after start of administration, by 0.68, −7.11, −8.95, 5.94% respectively 49 days after start of administration, and by −1.40, −0.98, −1.77, 4.57% respectively 83 days after start of administration, as compared to OVX control.

TABLE 3

| | Food consumption (g/24 hrs/rat): Days after initial treatment | | | Water consumption (ml/24 hrs/rat): Days after initial treatment | | |
|---|---|---|---|---|---|---|
| Groups | 28 | 49 | 83 | 28 | 49 | 83 |
| | | | Controls | | | |
| Sham | 15.55 ± 1.42 | 14.19 ± 1.70 | 12.47 ± 1.56 | 26.75 ± 3.49 | 37.00 ± 3.55 | 32.25 ± 4.77 |
| OVX | 20.29 ± 2.61$^a$ | 18.80 ± 2.61$^a$ | 17.13 ± 1.62$^a$ | 33.38 ± 5.13$^b$ | 48.88 ± 5.25$^d$ | 45.25 ± 5.97$^a$ |
| RC 40 mg/kg | 19.16 ± 3.54$^b$ | 18.93 ± 4.06$^a$ | 16.89 ± 2.82$^a$ | 34.75 ± 7.25$^b$ | 46.13 ± 4.73$^d$ | 44.75 ± 12.34$^b$ |
| PCP 20 mg/kg | 18.98 ± 3.06$^b$ | 17.47 ± 2.07$^b$ | 16.96 ± 2.40$^a$ | 36.13 ± 7.70$^a$ | 47.25 ± 10.43$^e$ | 52.00 ± 13.91$^a$ |
| | | | RC:PCP 2:1 mixture (g/g) | | | |
| 120 mg/kg | 18.49 ± 1.94$^b$ | 17.12 ± 2.97$^b$ | 16.83 ± 2.30$^a$ | 35.38 ± 4.78$^a$ | 46.00 ± 4.54$^d$ | 41.38 ± 5.95$^c$ |
| 60 mg/kg | 19.65 ± 3.50$^a$ | 19.92 ± 1.74$^a$ | 17.92 ± 4.40$^a$ | 38.38 ± 8.60$^d$ | 51.13 ± 8.82$^d$ | 50.50 ± 9.30$^a$ |

$^a$p < 0.01 and $^b$p < 0.05: comparison with sham control according to LSD test
$^c$p < 0.05: comparison with pomegranate extract 20 mg/kg administered group according to LSD test
$^d$p < 0.01 and $^e$p < 0.05: comparison with sham control according to MW test

Example 1-3. Change in Food Consumption

Significant (p<0.01) increases in food consumption were found in OVX control respectively 28, 49 and 83 days after start of administration as compared to sham control, changes in food consumption related to administration of red clover extract, pomegranate extract and red clover:pomegranate extract 2:1 (g/g) mixture compared to OVX control were not found at each of 28, 49 and 83 days when measured, and significant changes in food consumption were not found in all groups administered with all doses of red clover:pomegranate extract 2:1 (g/g) mixture as compared to each of red clover extract 40 mg/kg and pomegranate extract 20 mg/kg administered groups (Table 3).

In the case of OVX control, the food consumption at 28, 49 and 83 days after start of administration changed by 30.53, 32.50 and 37.35% as compared to sham control, and red clover extract 40 mg/kg, pomegranate extract 20 mg/kg, red clover:pomegranate extract 2:1 (g/g) mixture 120, 60 mg/kg administered groups changed in food consumption by changes by −23.64, −23.00, −38.90, and −31.87% respectively as compared to OVX control.

Example 1-4. Change in Water Consumption

Significant (p<0.01 or p<0.05) increases in water consumption were found in OVX control respectively 28, 49 and 83 days after start of administration as compared to sham control, changes in water consumption related to administration of red clover extract, pomegranate extract and red clover:pomegranate extract 2:1 (g/g) mixture compared to OVX control were not found at each of 28, 49 and 83 days when measured, and significant (p<0.05) decreases in water consumption were found in red clover:pomegranate extract 2:1 (g/g) mixture 120 mg/kg administered group merely 83 days after start of administration as compared to pomegranate extract 20 mg/kg administered group, and significant changes in water consumption were not found in all groups administered with all doses of red clover:pomegranate extract 2:1 (g/g) mixture as compared to each of red clover extract 40 mg/kg and pomegranate extract 20 mg/kg administered groups (Table 3).

In the case of OVX control, the water consumption at 28, 49 and 83 days after start of administration changed by 24.77, 32.09 and 40.31% respectively as compared to sham control, and red clover extract 40 mg/kg, pomegranate extract 20 mg/kg, red clover:pomegranate extract 2:1 (g/g)

mixture 120, 60 mg/kg administered groups changed in water consumption by 4.12, 8.24, 5.99, 14.98% respectively 28 days after start of administration, by −5.63, −3.32, −5.88, 4.60% respectively 49 days after start of administration, and by −1.10, 14.92, −8.56, 11.60% respectively 83 days after start of administration, as compared to OVX control.

Example 1-5. Change in Urine Volume

When respectively measured 28, 49 and 83 days after start of administration, significant changes in urine volume were not found in OVX control as compared to sham control, while red clover:pomegranate extract 2:1 (g/g) mixture 120 and 60 mg/kg administered group showed significant ($p<0.01$) increases in urine volume as compared to OVX control when respectively measured 28, 49 and 83 days after start of administration, and particularly, significant ($p<0.01$ or $p<0.05$) increases in urine volume were found at all the measurement dates as compared to red clover extract 40 mg/kg and pomegranate extract 20 mg/kg administered group (Table 4).

In the case of OVX control, the urine volume at 28, 49 and 83 days after start of administration changed by 1.61, 4.35 and 11.99% respectively as compared to sham control, and red clover extract 40 mg/kg, pomegranate extract 20 mg/kg, red clover:pomegranate extract 2:1 (g/g) mixture 120, 60 mg/kg administered groups had changes in urine volume by 5.82, −1.59, 80.95, 65.08%, respectively, 28 days after start of administration, by 53.33, 33.33, 115.83, 82.08%, respectively, 49 days after start of administration, and by 36.70, 34.25, 163.00, 115.29%, respectively, 83 days after start of administration, as compared to OVX control.

Example 1-6. Change in Fecal Excretion

OVX control showed insignificantly slight increases in in fecal excretion respectively 28, 49 and 83 days after start of administration when measured as compared to sham control, while red clover:pomegranate extract 2:1 (g/g) mixture 120 mg/kg administered group showed significant ($p<0.01$ or $p<0.05$) increases in fecal excretion respectively 49 and 83 days after start of administration as compared to OVX control, and red clover:pomegranate extract 2:1 (g/g) mixture 60 mg/kg administered group showed significant ($p<0.01$ or $p<0.05$) increases in fecal excretion respectively 28, 49 and 83 days after start of administration when measured as compared to OVX control, and particularly, significant ($p<0.01$ or $p<0.05$) increases in fecal excretion were found in red clover:pomegranate extract 2:1 (g/g) mixture 120 and 60 mg/kg administered group respectively 49 and 83 days after start of administration as compared to red clover extract 40 mg/kg and pomegranate extract 20 mg/kg administered group. In the case of OVX control, the fecal excretion at 28, 49 and 83 days after start of administration changed by 13.29, 26.96 and 25.76% respectively as compared to sham control, and red clover extract 40 mg/kg, pomegranate extract 20 mg/kg, red clover:pomegranate extract 2:1 (g/g) mixture 120, 60 mg/kg administered groups changed in fecal excretion by 28.46, 7.87, 25.15, 33.63% respectively 28 days after start of administration, by 42.80, 39.56, 90.16, 77.55% respectively 49 days after start of administration 49, and by 35.89, 32.54, 60.58, 57.03% respectively 83 days after start of administration, as compared to OVX control. (Table 4)

Example 1-7. Change in Abdominal Fat Pad Weight

Figure 5:
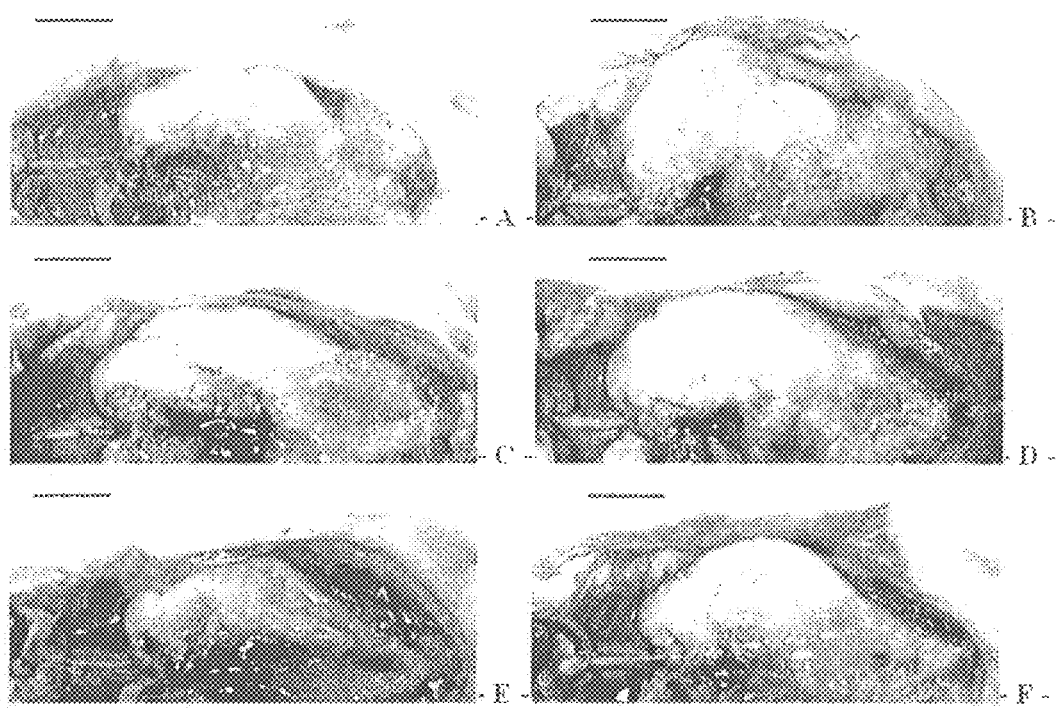
FIG. 5 shows fat accumulated in left abdominal walls taken from sham control or OVX rats. A shows sham control, B shows OVX control, C shows red clover extract 40 mg/kg administered group, D shows pomegranate extract 20 mg/kg administered group, E shows red clover:pomegranate extract 2:1 mixture (g/g) 120 mg/kg administered group, F shows red clover:pomegranate extract 2:1 mixture (g/g) 60 mg/kg administered group.

Significant ($p<0.01$) increases in absolute weight of fat deposited in left abdominal wall and relative weight to body weight were each found in OVX control as compared to sham control, while significant ($p<0.01$) decreases in abdominal fat pad weight were found in each of red clover:pomegranate extract 2:1 (g/g) mixture 120, 60 mg/kg administered groups as compared to OVX control. Particularly, significant ($p<0.01$) decreases in abdominal fat pad weight were found in red clover:pomegranate extract 2:1 (g/g) mixture 120 and 60 mg/kg administered groups as compared to each of red clover extract 40 mg/kg and pomegranate extract 20 mg/kg administered groups (Table 5, FIG. 5).

In the case of OVX control, the absolute weight of fat deposited in left abdominal wall and relative weight to body weight changed by 307.47 and 183.68% respectively as compared to sham control, and red clover extract 40 mg/kg, pomegranate extract 20 mg/kg, red clover:pomegranate extract 2:1 (g/g) mixture 120, 60 mg/kg administered groups had changes in absolute weight by −40.94, −36.38, −64.82, −55.77% respectively, and changes in abdominal fat pad relative weight by −35.49, −30.82, −59.59, −50.86% respectively, as compared to OVX control.

TABLE 4

| Groups | Urine volume (ml/24 hrs/rat): Days after initial treatment | | | Fecal excretion (g/24 hrs/rat): Days after initial treatment | | |
|---|---|---|---|---|---|---|
| | 28 | 49 | 83 | 28 | 49 | 83 |
| Controls | | | | | | |
| Sham | 2.33 ± 0.81 | 2.88 ± 0.50 | 3.65 ± 1.00 | 8.80 ± 2.53 | 8.23 ± 2.12 | 9.61 ± 3.33 |
| OVX | 2.36 ± 0.75 | 3.00 ± 0.50 | 4.09 ± 0.77 | 9.97 ± 3.13 | 10.44 ± 4.14 | 12.09 ± 2.47 |
| RC 40 mg/kg | 2.50 ± 0.90 | 4.60 ± 1.06$^{ab}$ | 5.59 ± 0.77$^{ac}$ | 12.81 ± 4.31$^i$ | 14.91 ± 3.07$^{ab}$ | 16.43 ± 1.73$^{hj}$ |
| PCP 20 mg/kg | 2.33 ± 0.71 | 4.00 ± 0.98$^{ac}$ | 5.49 ± 0.81$^{ac}$ | 10.76 ± 4.50 | 14.58 ± 2.76$^{ab}$ | 16.02 ± 1.03$^{hk}$ |
| RC:PCP 2:1 mixture (g/g) | | | | | | |
| 120 mg/kg | 4.28 ± 0.93$^{abdf}$ | 6.48 ± 1.10$^{abdf}$ | 10.75 ± 1.88$^{abdf}$ | 12.48 ± 4.38 | 19.86 ± 3.31$^{abdf}$ | 19.41 ± 1.33$^{hjlm}$ |
| 60 mg/kg | 3.90 ± 1.02$^{abdf}$ | 5.46 ± 0.60$^{abef}$ | 8.80 ± 1.69$^{abdf}$ | 13.33 ± 2.04$^{hk}$ | 18.54 ± 2.05$^{abeg}$ | 18.98 ± 1.64$^{hjlm}$ |

$^a$p < 0.01: comparison with sham control according to LSD test
$^b$p < 0.01 and $^c$p < 0.05: comparison with OVX control according to LSD test
$^d$p < 0.01 and $^e$p < 0.05: comparison with red clover extract 40 mg/kg administered group according to LSD test
$^f$p < 0.01 and $^g$p < 0.05: comparison with pomegranate extract 20 mg/kg administered group according to LSD test
$^m$p < 0.01: comparison with pomegranate extract 20 mg/kg administered group according to MW test
$^h$p < 0.01 and $^i$p < 0.05: comparison with sham control according to MW test
$^j$p < 0.01 and $^k$p < 0.05: comparison with OVX control according to MW test
$^l$p < 0.01: comparison with red clover extract 40 mg/kg administered group according to MW test

TABLE 5

| Groups | Absolute wet-weight (g) | | | Relative wet-weight (% of body weight) | | |
|---|---|---|---|---|---|---|
| | Abodminal fat pad | Uterus | Liver | Abodminal fat pad | Uterus | Liver |
| Controls | | | | | | |
| Sham | 3.608 ± 1.146 | 0.648 ± 0.148 | 7.374 ± 0.837 | 1.140 ± 0.351 | 0.209 ± 0.055 | 2.349 ± 0.245 |
| OVX | 14.703 ± 2.682$^f$ | 0.082 ± 0.007$^f$ | 7.372 ± 0.351 | 3.235 ± 0.604$^f$ | 0.018 ± 0.002$^f$ | 1.623 ± 0.118$^f$ |
| RC 40 mg/kg | 8.683 ± 1.261$^{fh}$ | 0.104 ± 0.014$^{fh}$ | 7.680 ± 0.606 | 2.087 ± 0.270$^{fh}$ | 0.025 ± 0.004$^{fh}$ | 1.849 ± 0.147$^{fi}$ |
| PCP 20 mg/kg | 9.355 ± 1.279$^{fh}$ | 0.101 ± 0.014$^{fh}$ | 7.663 ± 0.351 | 2.238 ± 0.329$^{fh}$ | 0.024 ± 0.004$^{fh}$ | 1.830 ± 0.066$^{fh}$ |
| RC:PCP 2:1 mixture (g/g) | | | | | | |
| 120 mg/kg | 5.173 ± 1.220$^{ghjl}$ | 0.136 ± 0.023$^{fhjl}$ | 8.477 ± 0.444$^{abde}$ | 1.307 ± 0.296$^{hjl}$ | 0.034 ± 0.006$^{fhjl}$ | 2.146 ± 0.096$^{hjl}$ |
| 60 mg/kg | 6.504 ± 0.979$^{fhjl}$ | 0.125 ± 0.011$^{fhjl}$ | 8.514 ± 0.736$^{abce}$ | 1.590 ± 0.181$^{fhjl}$ | 0.031 ± 0.003$^{fhjl}$ | 2.091 ± 0.188$^{ghkl}$ |

$^a$p < 0.01: comparison with sham control according to LSD test
$^b$p < 0.01: comparison with OVX control according to LSD test
$^c$p < 0.01 and $^d$p < 0.05: comparison with red clover extract 40 mg/kg administered group according to LSD test
$^e$p < 0.01: comparison with pomegranate extract 20 mg/kg administered group according to LSD test
$^f$p < 0.01 and $^g$p < 0.05: comparison with sham control according to MW test
$^h$p < 0.01 and $^i$p < 0.05: comparison with OVX control according to MW test
$^j$p < 0.01 and $^k$p < 0.05: comparison with red clover extract 40 mg/kg administered group according to MW test
$^l$p < 0.01: comparison with pomegranate extract 20 mg/kg administered group according to MW test

Example 1-8. Change in Uterus Weight

Figure 6:
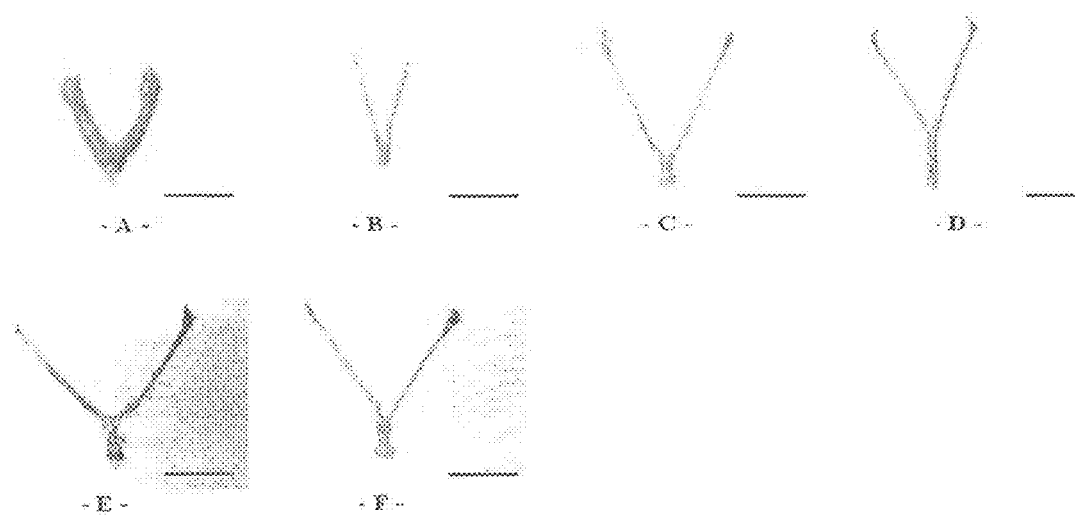
FIG. 6 shows uteri taken from sham control or OVX rats. A to G are arranged, starting from upper left; A shows sham control, B shows OVX control, C shows red clover extract 40 mg/kg administered group, D shows pomegranate extract 20 mg/kg administered group, E shows red clover:pomegranate extract 2:1 mixture (g/g) 120 mg/kg administered group, F shows red clover:pomegranate extract 2:1 mixture (g/g) 60 mg/kg administered group.

Significant (p<0.01) decreases in absolute uterus weight and relative uterus weight to body weight were each found in OVX control as compared to sham control, while significant (p<0.01) increases in uterus weight were each found in all test substance administered groups including red clover:pomegranate extract 2:1 (g/g) mixture administered groups as compared to OVX control. Particularly, significant (p<0.01) increases in uterus weight were found in each of red clover:pomegranate extract 2:1 (g/g) mixture 120 and 60 mg/kg administered groups as compared to each of red clover extract 40 mg/kg and pomegranate extract 20 mg/kg administered groups (Table 5, FIG. 6).

In the case of OVX control, the absolute uterus weight and relative uterus weight to body weight changed by −87.37 and −91.35% respectively as compared to sham control, and red clover extract 40 mg/kg, pomegranate extract 20 mg/kg, red clover:pomegranate extract 2:1 (g/g) mixture 120, 60 mg/kg administered groups had changes in absolute weight by 26.76, 23.39, 66.36, 52.75% respectively, and changes in relative uterus weight by 38.78, 33.80, 91.02, 70.17% respectively, as compared to OVX control.

Example 1-9. Change in Liver Weight

Significant (p<0.01) decreases in relative liver weight to body weight were found in OVX control as compared to sham control, while significant (p<0.01 or p<0.05) increases in relative liver weight were each found in all candidate substance administered groups including red clover:pomegranate extract 2:1 (g/g) mixture administered groups as compared to OVX control. Particularly, red clover:pomegranate extract 2:1 (g/g) mixture 120 and 60 mg/kg administered groups showed significant (p<0.01) increases in absolute liver weight as compared to OVX control, and significant (p<0.01 or p<0.05) increases in absolute and relative liver weights were each found as compared to each of red clover extract 40 mg/kg and pomegranate extract 20 mg/kg administered groups (Table 5).

In the case of OVX control, absolute liver weight and relative liver weight to body weight changed by −0.03 and −30.91% respectively as compared to sham control, and red clover extract 40 mg/kg, pomegranate extract 20 mg/kg, red clover:pomegranate extract 2:1 (g/g) mixture 120, 60 mg/kg administered groups had changes in absolute weight by 4.18, 3.96, 14.99, 15.49% respectively, and changes in relative liver weight by 13.95, 12.75, 32.21, 28.83% respectively, as compared to OVX control.

Example 1-10. Change in Bone Weight

Significant (p<0.01) decreases in wet/dry relative weights of femur, tibia and lumbar vertebrae (L5) to body weight as well as significant decreases in ash absolute and relative weights of femur, tibia and L5 were found in OVX control as compared to sham control, while remarkable increases in bone wet/dry relative weights were found in all test substance administered groups including pomegranate extract 20 mg/kg administered groups as compared to OVX control, and significant (p<0.01 or p<0.05) increases in relative and absolute bone ash weights were each found. Particularly, red clover:pomegranate extract 2:1 (g/g) mixture 120 and 60 mg/kg administered group showed remarkable increases in bone wet weight as compared to each of red clover extract 40 mg/kg and pomegranate extract 20 mg/kg administered groups, and significant (p<0.01 or p<0.05) increases in bone dry/ash absolute and relative weights were each found (Tables 6-8).

In the case of OVX control, the relative weight of wet, dry and ash bone of femur to body weight changed by −29.34, −31.02 and −42.92% respectively as compared to sham control, and red clover extract 40 mg/kg, pomegranate extract 20 mg/kg, red clover:pomegranate extract 2:1 (g/g) mixture 120, 60 mg/kg administered groups had changes in wet relative weight by 7.81, 12.49, 17.16, 14.78% respectively, changes in dry bone relative weight by 12.82, 11.11, 29.59, 24.58% respectively, and changes in ash femur relative weight by 25.36, 29.70, 53.23, 42.77% respectively, as compared to OVX control.

In the case of OVX control, the relative weights of wet, dry and ash bone of tibia to body weight changed by −27.38, −32.82 and −44.13% respectively as compared to sham control, and red clover extract 40 mg/kg, pomegranate extract 20 mg/kg, red clover:pomegranate extract 2:1 (g/g) mixture 120, 60 mg/kg administered groups had changes in wet relative weight by 7.22, 9.78, 22.73, 18.15% respectively, changes in dry bone relative weight by 13.83, 19.44, 36.30, 29.55% respectively, and changes in ash tibia relative weight by 30.03, 32.77, 62.18, 50.77% respectively, as compared to OVX control.

In the case of OVX control, the relative weights of wet, dry and ash bone of L5 to body weight changed by −29.62, −34.86 and −44.49% respectively as compared to sham control, and red clover extract 40 mg/kg, pomegranate extract 20 mg/kg, red clover:pomegranate extract 2:1 (g/g) mixture 120, 60 mg/kg administered groups had changes in wet relative weight by 6.91, 10.84, 34.79, 27.46% respectively, changes in dry bone relative weight by 15.82, 15.44, 42.68, 31.84% respectively, and changes in ash L5 relative weight by 26.19, 18.74, 48.36, 39.84% respectively, as compared to OVX control.

TABLE 6

| Groups | Absolute weight (g) | | | Relative weight (% of body weight) | | |
|---|---|---|---|---|---|---|
| | Wet | Dry | Ash | Wet | Dry | Ash |
| Controls | | | | | | |
| Sham | 0.996 ± 0.106 | 0.688 ± 0.073 | 0.432 ± 0.050 | 0.317 ± 0.026 | 0.219 ± 0.013 | 0.137 ± 0.009 |
| OVX | 1.020 ± 0.082 | 0.685 ± 0.043 | 0.356 ± 0.040$^a$ | 0.224 ± 0.012$^a$ | 0.151 ± 0.012$^a$ | 0.078 ± 0.009$^a$ |
| RC 40 mg/kg | 1.003 ± 0.107 | 0.706 ± 0.061 | 0.407 ± 0.034$^c$ | 0.241 ± 0.027$^a$ | 0.170 ± 0.016$^{ac}$ | 0.098 ± 0.009$^{ac}$ |
| PCP 20 mg/kg | 1.055 ± 0.058 | 0.702 ± 0.082 | 0.425 ± 0.021$^c$ | 0.252 ± 0.014$^{ac}$ | 0.168 ± 0.017$^{ad}$ | 0.102 ± 0.004$^{ac}$ |
| RC:PCP 2:1 mixture (g/g) | | | | | | |
| 120 mg/kg | 1.036 ± 0.083 | 0.772 ± 0.033$^{aceg}$ | 0.474 ± 0.029$^{bceg}$ | 0.262 ± 0.014$^{ace}$ | 0.195 ± 0.008$^{aceg}$ | 0.120 ± 0.007$^{aceg}$ |
| 60 mg/kg | 1.048 ± 0.096 | 0.765 ± 0.039$^{aceg}$ | 0.455 ± 0.030$^{ce}$ | 0.257 ± 0.021$^{ac}$ | 0.188 ± 0.012$^{aceg}$ | 0.112 ± 0.009$^{aceh}$ |

$^a$p < 0.01 and $^b$p < 0.05: comparison with sham control according to LSD test
$^c$p < 0.01 and $^d$p < 0.05: comparison with OVX control according to LSD test
$^e$p < 0.01 and $^f$p < 0.05: comparison with red clover extract 40 mg/kg administered group according to LSD test
$^g$p < 0.01 and $^h$p < 0.05: comparison with pomegranate extract 20 mg/kg administered group according to LSD test

TABLE 7

| Groups | Absolute weight (g) | | | Relative weight (% of body weight) | | |
|---|---|---|---|---|---|---|
| | Wet | Dry | Ash | Wet | Dry | Ash |
| Controls | | | | | | |
| Sham | 0.717 ± 0.065 | 0.520 ± 0.056 | 0.343 ± 0.037 | 0.228 ± 0.012 | 0.165 ± 0.009 | 0.110 ± 0.016 |
| OVX | 0.754 ± 0.047 | 0.504 ± 0.016 | 0.278 ± 0.037$^a$ | 0.166 ± 0.007$^a$ | 0.111 ± 0.005$^a$ | 0.061 ± 0.010$^a$ |
| RC 40 mg/kg | 0.737 ± 0.058 | 0.524 ± 0.039 | 0.331 ± 0.025$^c$ | 0.178 ± 0.015$^{ad}$ | 0.126 ± 0.011$^{ac}$ | 0.080 ± 0.006$^{ac}$ |
| PCP 20 mg/kg | 0.760 ± 0.037 | 0.554 ± 0.029$^d$ | 0.341 ± 0.025$^c$ | 0.182 ± 0.013$^{ac}$ | 0.132 ± 0.009$^{ac}$ | 0.081 ± 0.006$^{ac}$ |
| RC:PCP 2:1 mixture (g/g) | | | | | | |
| 120 mg/kg | 0.803 ± 0.041$^{ade}$ | 0.597 ± 0.032$^{aceg}$ | 0.393 ± 0.030$^{aceg}$ | 0.203 ± 0.010$^{aceg}$ | 0.151 ± 0.007$^{aceg}$ | 0.099 ± 0.008$^{bceg}$ |
| 60 mg/kg | 0.796 ± 0.019$^{adf}$ | 0.585 ± 0.042$^{ace}$ | 0.376 ± 0.031$^{bceh}$ | 0.196 ± 0.010$^{aceh}$ | 0.144 ± 0.009$^{aceh}$ | 0.092 ± 0.010$^{acfh}$ |

$^a$p < 0.01 and $^b$p < 0.05: comparison with sham control according to LSD test
$^c$p < 0.01 and $^d$p < 0.05: comparison with OVX control according to LSD test
$^e$p < 0.01 and $^f$p < 0.05: comparison with red clover extract 40 mg/kg administered group according to LSD test
$^g$p < 0.01 and $^h$p < 0.05: comparison with pomegranate extract 20 mg/kg administered group according to LSD test

TABLE 8

| Groups | Absolute weight (g) | | | Relative weight (% of body weight) | | |
|---|---|---|---|---|---|---|
| | Wet | Dry | Ash | Wet | Dry | Ash |
| Controls | | | | | | |
| Sham | 0.388 ± 0.046 | 0.249 ± 0.039 | 0.144 ± 0.013 | 0.123 ± 0.014 | 0.079 ± 0.010 | 0.046 ± 0.002 |
| OVX | 0.396 ± 0.051 | 0.234 ± 0.027 | 0.115 ± 0.009$^a$ | 0.087 ± 0.010$^a$ | 0.051 ± 0.005$^i$ | 0.025 ± 0.003$^a$ |
| RC 40 mg/kg | 0.386 ± 0.073 | 0.248 ± 0.022 | 0.133 ± 0.009$^{bc}$ | 0.093 ± 0.016$^a$ | 0.060 ± 0.006$^{il}$ | 0.032 ± 0.003$^{ac}$ |
| PCP 20 mg/kg | 0.404 ± 0.033 | 0.249 ± 0.022 | 0.126 ± 0.007$^{ac}$ | 0.096 ± 0.007$^a$ | 0.059 ± 0.006$^{il}$ | 0.030 ± 0.002$^{ac}$ |
| RC:PCP 2:1 mixture (g/g) | | | | | | |
| 120 mg/kg | 0.463 ± 0.043$^{adeh}$ | 0.290 ± 0.018$^{aceg}$ | 0.149 ± 0.009$^{ceg}$ | 0.117 ± 0.010$^{ceg}$ | 0.073 ± 0.004$^{kmo}$ | 0.038 ± 0.003$^{aceg}$ |
| 60 mg/kg | 0.451 ± 0.051$^{bdh}$ | 0.277 ± 0.033$^{bcfh}$ | 0.145 ± 0.007$^{cfg}$ | 0.111 ± 0.013$^{bceh}$ | 0.068 ± 0.007$^{jknp}$ | 0.036 ± 0.002$^{aceg}$ |

$^a$p < 0.01 and $^b$p < 0.05: comparison with sham control according to LSD test
$^c$p < 0.01 and $^d$p < 0.05: comparison with OVX control according to LSD test
$^e$p < 0.01 and $^f$p < 0.05: comparison with red clover extract 40 mg/kg administered group according to LSD test
$^g$p < 0.01 and $^h$p < 0.05: comparison with pomegranate extract 20 mg/kg administered group according to LSD test
$^i$p < 0.01 and $^j$p < 0.05: comparison with sham control according to MW test
$^k$p < 0.01 and $^l$p < 0.05: comparison with OVX control according to MW test
$^m$p < 0.01 and $^n$p < 0.05: comparison with red clover extract 40 mg/kg administered group according to MW test
$^o$p < 0.01 and $^p$p < 0.05: comparison with pomegranate extract 20 mg/kg administered group according to MW test

Example 1-11. Serum Biochemical Change (1): AST, ALT, TC, LDL, HDL and TG

Significant (p<0.01) increases in serum Aspartate aminotransferase (AST), Alanine aminotransferase (ALT), Total cholesterol (TC), Low density lipoprotein (LDL) and Triglyceride (TG) levels as well as significant (p<0.05) decreases in High density lipoprotein (HDL) level were found in OVX control as compared to sham control, while significant (p<0.01 or p<0.05) decreases in serum AST, ALT, TC, LDL and TG levels and significant increases in serum HDL level were each found in of all test substance administered groups as compared to OVX control. Particularly, red clover:pomegranate extract 2:1 (g/g) mixture 120 and 60 mg/kg administered groups showed significant (p<0.01) increases in serum HDL level as compared to OVX control, and significant (p<0.01 or p<0.05) decreases in serum AST, ALT, TC, LDL and TG levels and significant increases in HDL level were each found as compared to each of red clover extract 40 mg/kg and pomegranate extract 20 mg/kg administered groups (Table 9).

In the case of OVX control, the serum AST and ALT levels changed by 77.03 and 72.53% respectively as compared to sham control, and red clover extract 40 mg/kg, pomegranate extract 20 mg/kg, red clover:pomegranate extract 2:1 (g/g) mixture 120, 60 mg/kg administered groups had changes in AST level by −14.50, −12.10, −31.63, −25.80% respectively, and changes in serum ALT level by −20.70, −16.77, −34.93, −29.30% respectively, as compared to OVX control.

In the case of OVX control, the serum TC and LDL levels changed by 105.00 and 163.08% respectively as compared to sham control, and red clover extract 40 mg/kg, pomegranate extract 20 mg/kg, red clover:pomegranate extract 2:1 (g/g) mixture 120, 60 mg/kg administered groups had changes in TC level by −24.00, −20.98, −40.39, −36.78% respectively, and changes in serum DL level by −22.37, −24.56, −44.30, −39.62% respectively, as compared to OVX control.

Figure 7:
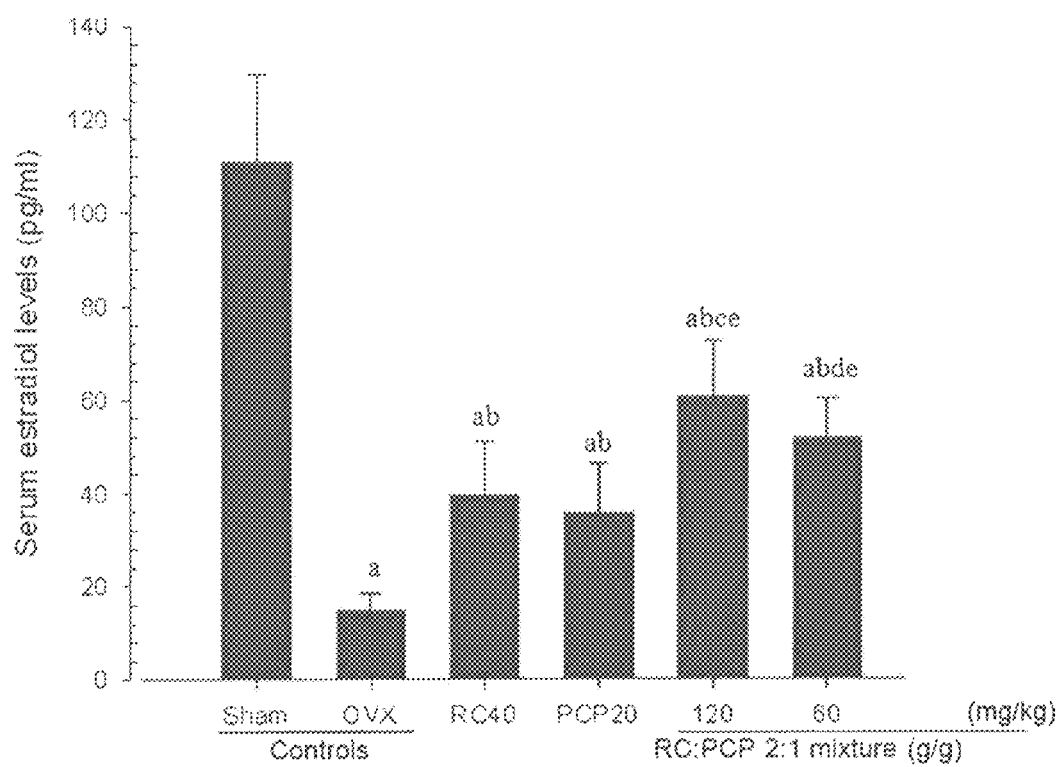
FIG. 7 shows serum estradiol levels of OVX rats. a $p<0.01$: comparison with sham control according to MW test, b $p<0.01$: comparison with OVX control according to MW test, c $p<0.01$ and d $p<0.05$: comparison with red clover extract 40 mg/kg administered group according to MW test, e $p<0.01$: comparison with pomegranate extract 20 mg/kg administered group according to MW test.

In the case of OVX control, the serum HDL and TG levels changed by −18.62 and 121.81% respectively as compared to sham control, and red clover extract 40 mg/kg, pomegranate extract 20 mg/kg, red clover:pomegranate extract 2:1 (g/g) mixture 120, 60 mg/kg administered groups had changes in HDL level by 5.88, 13.73, 52.92, 41.83% respectively, and changes in serum TG level by −27.51, −24.69, −42.68, −36.92% respectively, as compared to OVX control.

estradiol level were found in each of red clover:pomegranate extract 2:1 (g/g) mixture 120, 60 mg/kg administered groups as compared to OVX control. Particularly, significant (p<0.01 or p<0.05) increases in serum estradiol level were found in each of red clover:pomegranate extract 2:1 (g/g) mixture 120 and 60 mg/kg administered groups as compared to each of red clover extract 40 mg/kg and pomegranate extract 20 mg/kg administered groups (FIG. 7).

In the case of OVX control, the serum estradiol level changed by −86.58% as compared to sham control, and red clover extract 40 mg/kg, pomegranate extract 20 mg/kg, red clover:pomegranate extract 2:1 (g/g) mixture 120, 60 mg/kg administered groups had changes in serum estradiol level by 165.55, 141.18, 307.56, 247.90% respectively as compared to OVX control.

Example 1-13. Serum Biochemical Change (3): Osteocalcin and bALP

Figure 8:
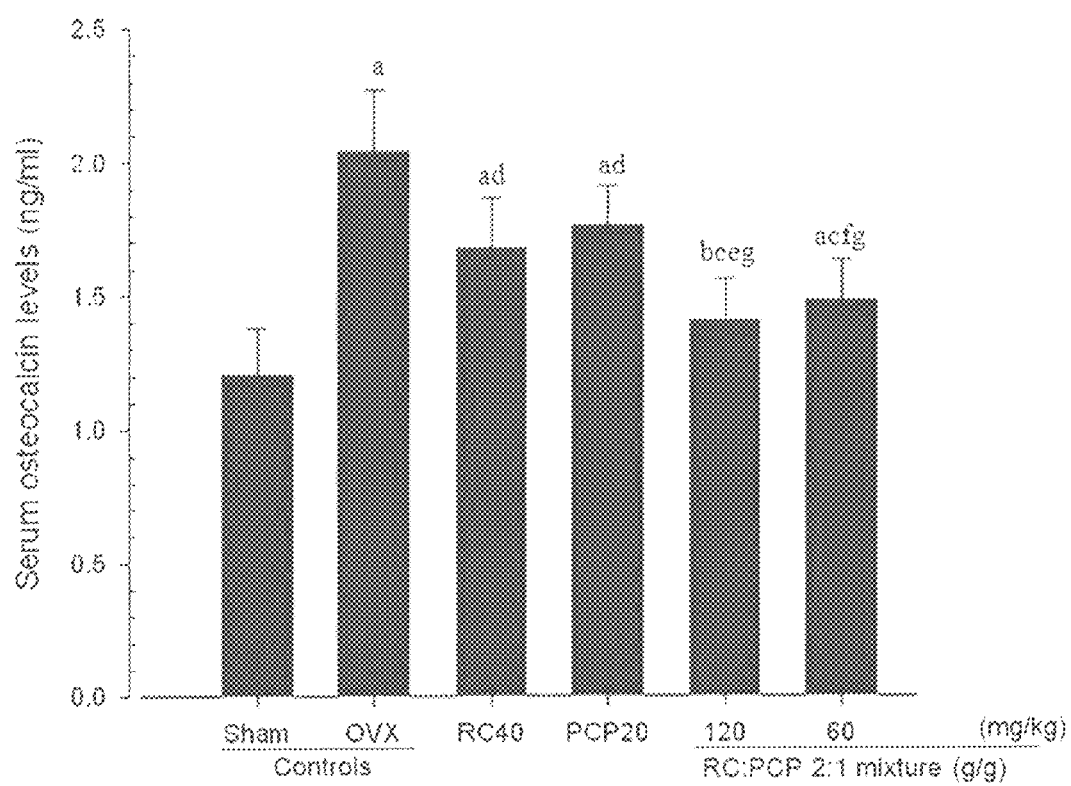
FIG. 8 shows serum osteocalcin levels of OVX rats. a $p<0.01$ and b $p<0.05$: comparison with sham control according to LSD test, c $p<0.01$ and d $p<0.05$: comparison with OVX control according to LSD test, e $p<0.01$ and f $p<0.05$: comparison with red clover extract 40 mg/kg administered group according to LSD test, g $p<0.01$: comparison with pomegranate extract 20 mg/kg administered group according to LSD test.
Figure 9:
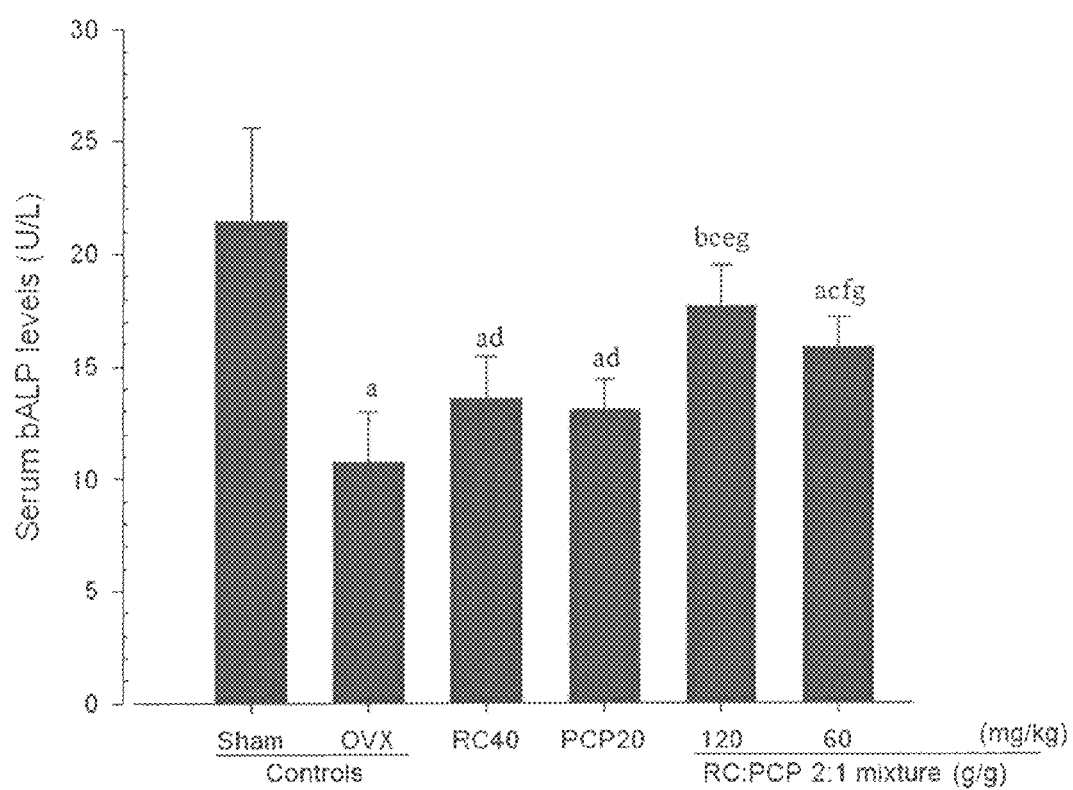
FIG. 9 shows serum bALP levels of OVX rats. a $p<0.01$ and b $p<0.05$: comparison with sham control according to MW test, c $p<0.01$ and d $p<0.05$: comparison with OVX control according to MW test, e $p<0.01$ and f $p<0.05$: comparison with red clover extract 40 mg/kg administered group according to MW test, g $p<0.01$: comparison with pomegranate extract 20 mg/kg administered group according to MW test.

Significant (p<0.01) increases in serum osteocalcin level as well as significant (p<0.01) decreases in bALP level were found in OVX control as compared to sham control, while significant (p<0.01 or p<0.05) decreases in serum osteocalcin level as well as significant increases in serum bALP level were each found in all candidate substance administered groups as compared to OVX control. Particularly, significant (p<0.01 or p<0.05) decreases in serum osteocalcin level and significant increases in bALP level were each found in red clover:pomegranate extract 2:1 (g/g) mixture 120 and 60 mg/kg administered groups as compared to each of red clover extract 40 mg/kg and pomegranate extract 20 mg/kg administered groups (FIGS. 8 and 9).

In the case of OVX control, the serum osteocalcin and bALP levels changed by 69.33 and −49.94% respectively as compared to sham control, and red clover extract 40 mg/kg, pomegranate extract 20 mg/kg, red clover:pomegranate extract 2:1 (g/g) mixture 120, 60 mg/kg administered groups had changes in osteocalcin level by −17.75, −13.83, −31.27, −27.36% respectively, and changes in serum bALP level 26.37, 21.16, 64.38, 47.53% respectively, as compared to OVX control.

Example 1-14. Change in Bone Mineral Density

OVX control significantly (p<0.01) decreased in bone mineral density of total, neck and mid-shaft region of femur

TABLE 9

| Groups | Serum biochemistrical values | | | | | |
|---|---|---|---|---|---|---|
| | AST (U/L) | ALT (U/L) | TC (mg/dl) | LDL (mg/dl) | HDL (mg/dl) | TG (mg/dl) |
| Controls | | | | | | |
| Sham | 96.86 ± 12.54 | 68.25 ± 14.62 | 62.50 ± 13.48 | 32.50 ± 10.94 | 23.50 ± 4.81 | 53.88 ± 13.15 |
| OVX | 171.50 ± 21.79$^a$ | 117.75 ± 19.56$^h$ | 128.13 ± 19.70$^a$ | 85.50 ± 15.92$^a$ | 19.13 ± 3.23$^b$ | 119.50 ± 29.00$^h$ |
| RC 40 mg/kg | 146.63 ± 6.80$^{ac}$ | 93.38 ± 7.93$^{hj}$ | 97.38 ± 10.01$^{ac}$ | 66.38 ± 11.61$^{ac}$ | 20.25 ± 2.19 | 86.63 ± 10.84$^{hj}$ |
| PCP 20 mg/kg | 150.75 ± 7.81$^{ac}$ | 98.00 ± 7.58$^{hk}$ | 101.25 ± 14.36$^{ac}$ | 64.50 ± 11.07$^{ac}$ | 21.75 ± 3.96 | 90.00 ± 12.06$^{hk}$ |
| RC:PCP 2:1 mixture (g/g) | | | | | | |
| 120 mg/kg | 117.25 ± 13.33$^{acdf}$ | 76.63 ± 9.16$^{jln}$ | 76.38 ± 9.13$^{cdf}$ | 47.63 ± 9.83$^{bcdf}$ | 29.13 ± 4.09$^{bcdf}$ | 68.50 ± 10.69$^{ijln}$ |
| 60 mg/kg | 127.25 ± 15.98$^{acef}$ | 83.25 ± 7.59$^{ijmn}$ | 81.00 ± 14.01$^{bcef}$ | 51.63 ± 7.67$^{aceg}$ | 27.13 ± 4.05$^{cdg}$ | 75.38 ± 7.61$^{hjmo}$ |

Example 1.12. Serum Biochemical Change (2): Estradiol

Significant (p<0.01) decreases in serum estradiol level were found in OVX control as compared to sham control, while significant (p<0.01 or p<0.05) increases in serum and tibia as well as total bone mineral density of fourth lumbar vertebrae (L4) as compared to sham control, while significant (p<0.01 or p<0.05) increases in bone mineral density were each found in all test substance administered groups all over the measured regions as compared to OVX control. Particularly, remarkable increases in bone mineral density were found in each of red clover:pomegranate extract 2:1 (g/g) mixture 120 and 60 mg/kg administered groups all over the measured regions as compared to each of red clover extract 40 mg/kg and pomegranate extract 20 mg/kg administered groups (Table 10).

OVX control had changes in bone mineral density of femur total, neck and mid-shaft region by −18.42, −20.06 and −16.44% as compared to normal control, and red clover extract 40 mg/kg, pomegranate extract 20 mg/kg, red clover:pomegranate extract 2:1 (g/g) mixture 120, 60 mg/kg administered groups had changes in total bone mineral density by 5.67, 5.46, 14.64, 11.13% respectively, changes in neck bone mineral density by 9.33, 6.65, 22.12, 16.77% respectively, and changes in mid-shaft bone mineral density by 7.94, 5.81, 16.47, 13.51% respectively, as compared to OVX control.

OVX control had changes in bone mineral density of tibia total, neck and mid-shaft region by −22.65, −20.24 and −28.62% respectively as compared to normal control, and red clover extract 40 mg/kg, pomegranate extract 20 mg/kg, red clover:pomegranate extract 2:1 (g/g) mixture 120, 60 mg/kg administered groups had changes in total bone mineral density by 8.92, 6.75, 19.28, 16.75% respectively, changes in neck bone mineral density by 8.39, 6.45, 18.71, 14.95% respectively, and changes in mid-shaft bone mineral density by 13.22, 11.01, 30.21, 19.38% respectively, as compared to OVX control.

Figure 10:
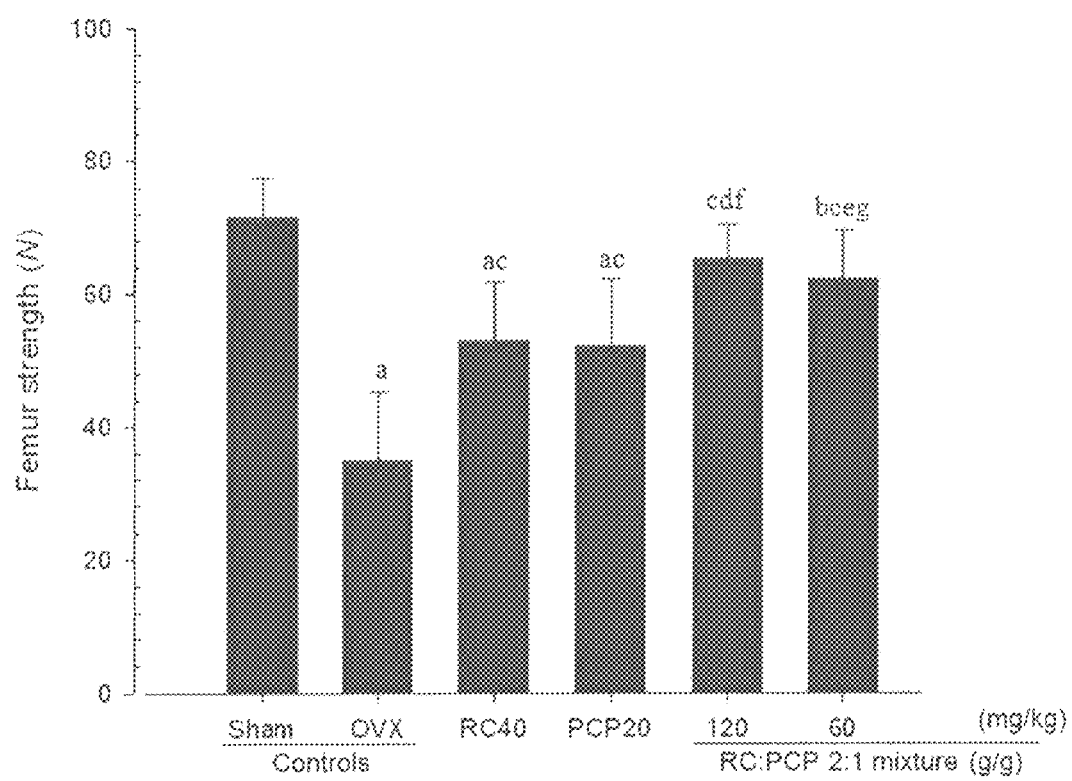
FIG. 10 shows femur strength of OVX rats. a $p<0.01$ and b $p<0.05$: comparison with sham control according to LSD test, c $p<0.01$: comparison with OVX control according to LSD test, d $p<0.01$ and e $p<0.05$: comparison with red clover extract 40 mg/kg administered group according to LSD test, f $p<0.01$ and g $p<0.05$: comparison with pomegranate extract 20 mg/kg administered group according to LSD test.
Figure 11:
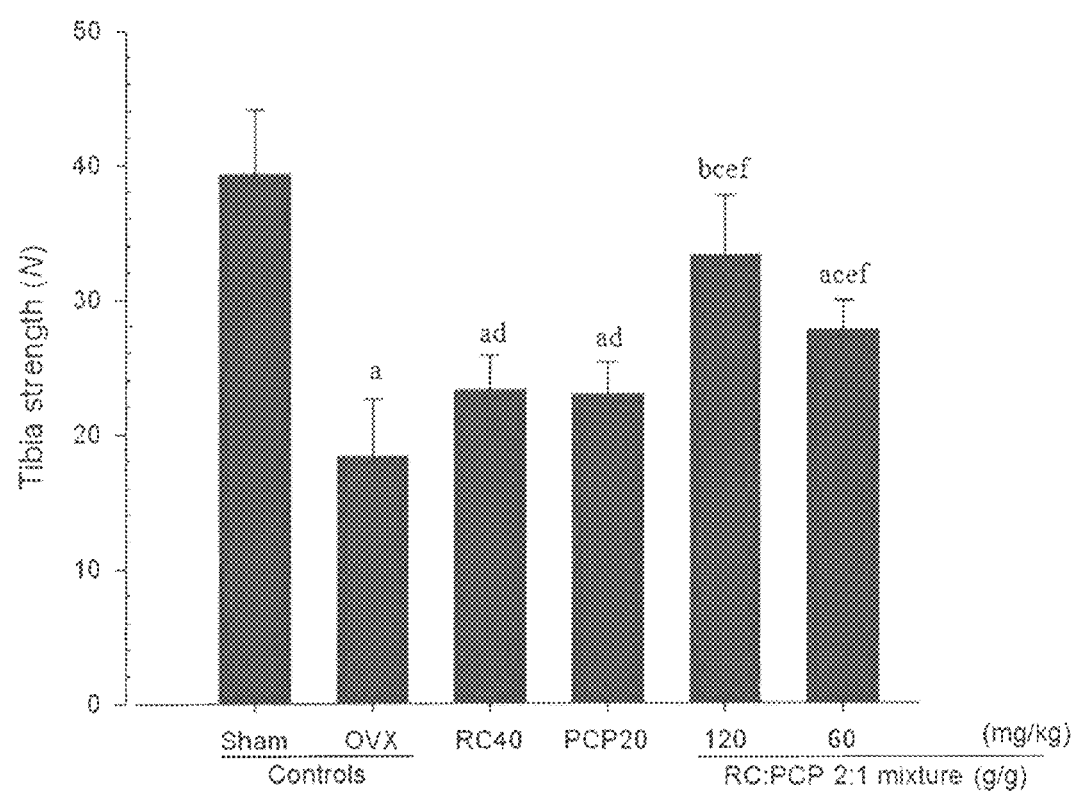
FIG. 11 shows tibia strength. a $p<0.01$ and b $p<0.05$: comparison with sham control according to MW test, c $p<0.01$ and d $p<0.05$: comparison with OVX control according to MW test, e $p<0.01$: comparison with red clover extract 40 mg/kg administered group according to MW test, f $p<0.01$: comparison with pomegranate extract 20 mg/kg administered group according to MW test.

OVX control had changes in L4 total bone mineral density by −21.38% as compared to normal control, and red clover extract 40 mg/kg, pomegranate extract 20 mg/kg, red clover:pomegranate extract 2:1 (g/g) mixture 120, 60 mg/kg administered groups had changes in L4 total bone mineral density by 9.60, 7.43, 18.74, 15.20% respectively as compared to OVX control.

found in each of red clover:pomegranate extract 2:1 (g/g) mixture 120 and 60 mg/kg administered groups as compared to each of red clover extract 40 mg/kg and pomegranate extract 20 mg/kg administered groups (FIGS. 10 and 11).

In the case of OVX control, the bone strength of femur and tibia mid-shaft regions changed by −51.06 and −53.22% respectively as compared to sham control, and red clover extract 40 mg/kg, pomegranate extract 20 mg/kg, red clover:pomegranate extract 2:1 (g/g) mixture 120, 60 mg/kg administered groups had changes in femur mid-shaft region bone strength by 51.66, 48.93, 87.20, 78.09% respectively, and changes in bone strength of tibia mid-shaft region by 26.38, 24.75, 80.90, 50.49% respectively, as compared to OVX control.

Example 1-16. Histological Change (1): Abdominal Wall Fat Pad, Uterus and Liver (1) Abdominal Wall Fat Pad Significant ($p<0.01$) increases in abdominal wall fat pad thickness caused by remarkable increases in abdominal wall fat deposition and significant ($p<0.01$) increases in mean adipocyte diameter were each found in OVX control as compared to sham control, while significant ($p<0.01$) decreases in abdominal wall fat pad and adipocyte diameter were each found in all test substance administered groups as compared to OVX control. Particularly, red clover:pomegranate extract 2:1 (g/g) mixture 120 and 60 mg/kg administered groups showed presumably significant ($p<0.01$ or $p<0.05$) inhibition of abdominal wall fat deposition and adipocyte hypertrophy as compared to each of red clover

TABLE 10

| Groups | Control | | References | | RC:PCP 2:1 mixture(g/g) | |
|---|---|---|---|---|---|---|
| | Sham | OVX | RC 40 mg/kg | PCP 20 mg/kg | 120 mg/kg | 60 mg/kg |
| Femur | | | | | | |
| Total | 0.149 ± 0.010 | 0.121 ± 0.006$^a$ | 0.128 ± 0.004$^{ac}$ | 0.128 ± 0.005$^{ac}$ | 0.139 ± 0.005$^{aceg}$ | 0.135 ± 0.004$^{acfh}$ |
| Neck | 0.158 ± 0.012 | 0.126 ± 0.003$^i$ | 0.138 ± 0.010$^{ik}$ | 0.134 ± 0.004$^{ik}$ | 0.154 ± 0.008$^{kmo}$ | 0.147 ± 0.004$^{jko}$ |
| Mid-shaft | 0.126 ± 0.005 | 0.106 ± 0.004$^a$ | 0.114 ± 0.004$^{ac}$ | 0.112 ± 0.004$^{ac}$ | 0.123 ± 0.003$^{ceg}$ | 0.120 ± 0.003$^{aceg}$ |
| Tibia | | | | | | |
| Total | 0.134 ± 0.010 | 0.104 ± 0.003$^a$ | 0.113 ± 0.007$^{ac}$ | 0.111 ± 0.003$^{ad}$ | 0.124 ± 0.004$^{aceg}$ | 0.121 ± 0.005$^{aceg}$ |
| Neck | 0.146 ± 0.007 | 0.116 ± 0.006$^a$ | 0.126 ± 0.005$^{ad}$ | 0.124 ± 0.004$^{ad}$ | 0.138 ± 0.005$^{bceg}$ | 0.134 ± 0.006$^{aceg}$ |
| Mid-shaft | 0.119 ± 0.012 | 0.085 ± 0.007$^i$ | 0.096 ± 0.005$^{ik}$ | 0.095 ± 0.005$^{il}$ | 0.111 ± 0.008$^{kmo}$ | 0.102 ± 0.004$^{iknp}$ |
| L4-Total | 0.139 ± 0.009 | 0.109 ± 0.005$^a$ | 0.120 ± 0.005$^{ac}$ | 0.118 ± 0.006$^{ad}$ | 0.130 ± 0.008$^{bceg}$ | 0.126 ± 0.004$^{ach}$ |

Figure 12:
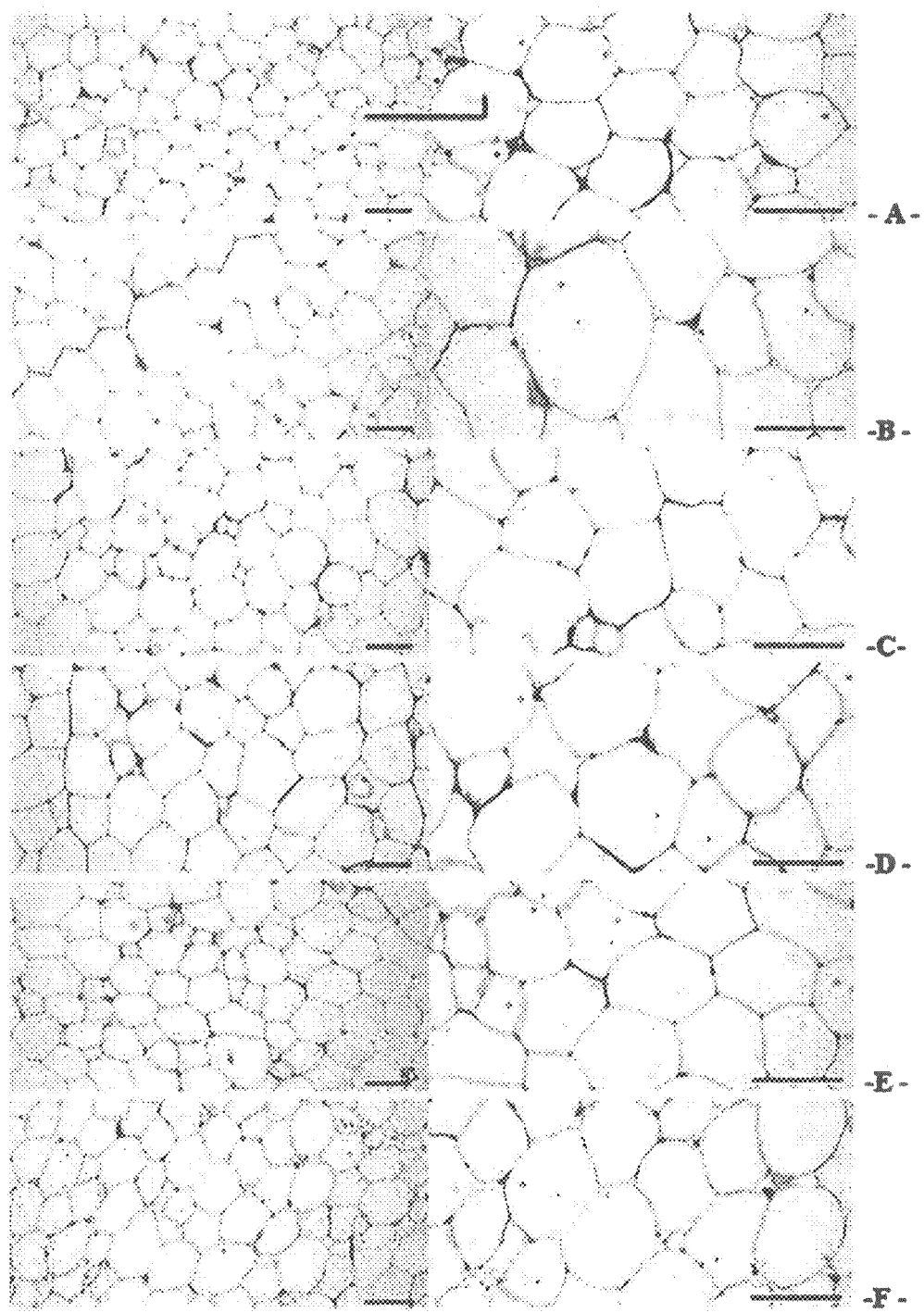
FIG. 12 shows a histological image of adipocytes taken from abdominal fat in the dorsal abdominal muscles of sham control or OVX rats. A shows sham control, B shows OVX control, C shows red clover extract 40 mg/kg administered group, D shows pomegranate extract 20 mg/kg administered group, E shows red clover:pomegranate extract 2:1 mixture (g/g) 120 mg/kg administered group, F shows red clover:pomegranate extract 2:1 mixture (g/g) 60 mg/kg administered group.

$^a p < 0.01$ and $^b p < 0.05$: comparison with sham control according to LSD test
$^c p < 0.01$ and $^d p < 0.05$: comparison with OVX control according to LSD test
$^e p < 0.01$ and $^f p < 0.05$: comparison with red clover extract 40 mg/kg administered group according to LSD test
$^g p < 0.01$ and $^h p < 0.05$: comparison with pomegranate extract 20 mg/kg administered group according to LSD test
$^i p < 0.01$ and $^j p < 0.05$: comparison with sham control according to MW test
$^k p < 0.01$ and $^l p < 0.05$: comparison with OVX control according to MW test
$^m p < 0.01$ and $^n p < 0.05$: comparison with red clover extract 40 mg/kg administered group according to MW test
$^o p < 0.01$ and $^p p < 0.05$: comparison with pomegranate extract 20 mg/kg administered group according to MW test Example 1-15. Change in Bone Strength OVX control significantly ($p<0.01$) decreased in bone strength of mid-shaft region of femur and tibia as compared to sham control, while significant ($p<0.01$ or $p<0.05$) increases in bone strength of femur and tibia were each found in all candidate substance administered groups including three doses of red clover:pomegranate extract 2:1 (g/g) mixture administered groups as compared to OVX control. Particularly, significant ($p<0.01$ or $p<0.05$) increases in bone mineral density in mid-shaft regions of femur and tibia were extract 40 mg/kg and pomegranate extract 20 mg/kg administered groups (Table 11, FIG. 12).

The abdominal wall fat pad thickness and mean adipocyte diameter changed by 122.59 and 92.42% respectively in OVX control as compared to normal control, and red clover extract 40 mg/kg, pomegranate extract 20 mg/kg, red clover:pomegranate extract 2:1 (g/g) mixture 120, 60 mg/kg administered groups had changes in abdominal wall fat pad thickness by −21.81, −18.61, −43.66, −35.33% respectively, and changes in mean adipocyte diameter by −25.72, −19.19, −37.39, −35.67% respectively, as compared to OVX control.

(2) Uterus

Figure 13:
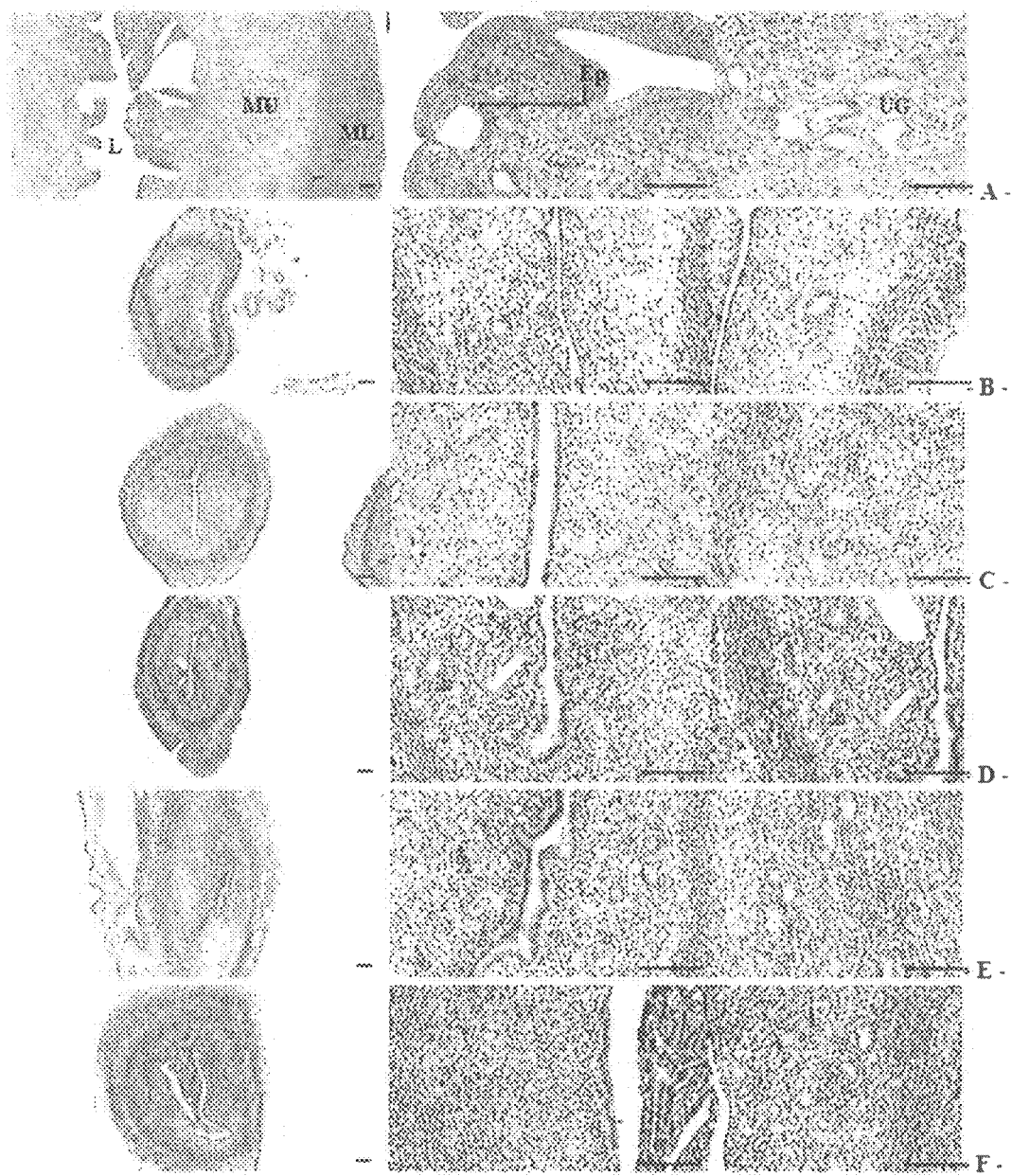
FIG. 13 shows a histological image of left uterine horns taken from sham control or OVX rats. A shows sham control, B shows OVX control, C shows red clover extract 40 mg/kg administered group, D shows pomegranate extract 20 mg/kg administered group, E shows red clover:pomegranate extract 2:1 mixture (g/g) 120 mg/kg administered group, F shows red clover:pomegranate extract 2:1 mixture (g/g) 60 mg/kg administered group. L represents Lumen; MU represents Mucosa; ML represents Muscular layer; Ep represents Epithelium; UG represents Uterine gland.

Disuse atrophy contributing to remarkable decreases in uterine mucosa occurred in OVX control, and significant (p<0.01) decreases in total, epithelium and mucosa thickness of uterus and percentage of uterine glands in the mucosa were each found in OVX control as compared to sham control, while significant (p<0.01) increases in total, epithelium and mucosa thickness of uterus and percentage of uterine glands in the mucosa were each found in all candidate substance administered groups as compared to OVX control, and particularly, red clover:pomegranate extract 2:1 (g/g) mixture 120 and 60 mg/kg administered groups showed presumably significant (p<0.01 or p<0.05) histological inhibition of disuse atrophy of uterus as compared to each of red clover extract 40 mg/kg and pomegranate extract 20 mg/kg administered groups (Table 11, FIG. 13).

The mean thickness of total and epithelium of uterus changed by −83.08 and −74.62% respectively in OVX control as compared to normal control, and red clover extract 40 mg/kg, pomegranate extract 20 mg/kg, red clover:pomegranate extract 2:1 (g/g) mixture 120, 60 mg/kg administered groups had changes in mean total uterus thickness 62.99, 34.94, 167.13, 102.53% respectively, and changes in uterine epithelium mean thickness by 73.09, 96.22, 148.66, 133.62% respectively, as compared to OVX control.

The mucosa mean thickness of uterus and percentage of uterine glands in the mucosa changed by −81.70 and −83.16% respectively in OVX control as compared to normal control, and red clover extract 40 mg/kg, pomegranate extract 20 mg/kg, red clover:pomegranate extract 2:1 (g/g) mixture 120, 60 mg/kg administered groups had changes in uterine mucosa mean thickness by 56.88, 47.96, 174.02, 137.75% respectively, and changes in percentage of uterine glands in the mucosa by 91.41, 127.57, 314.70, 264.53% respectively, as compared to OVX control.

(3) Liver

Figure 14:
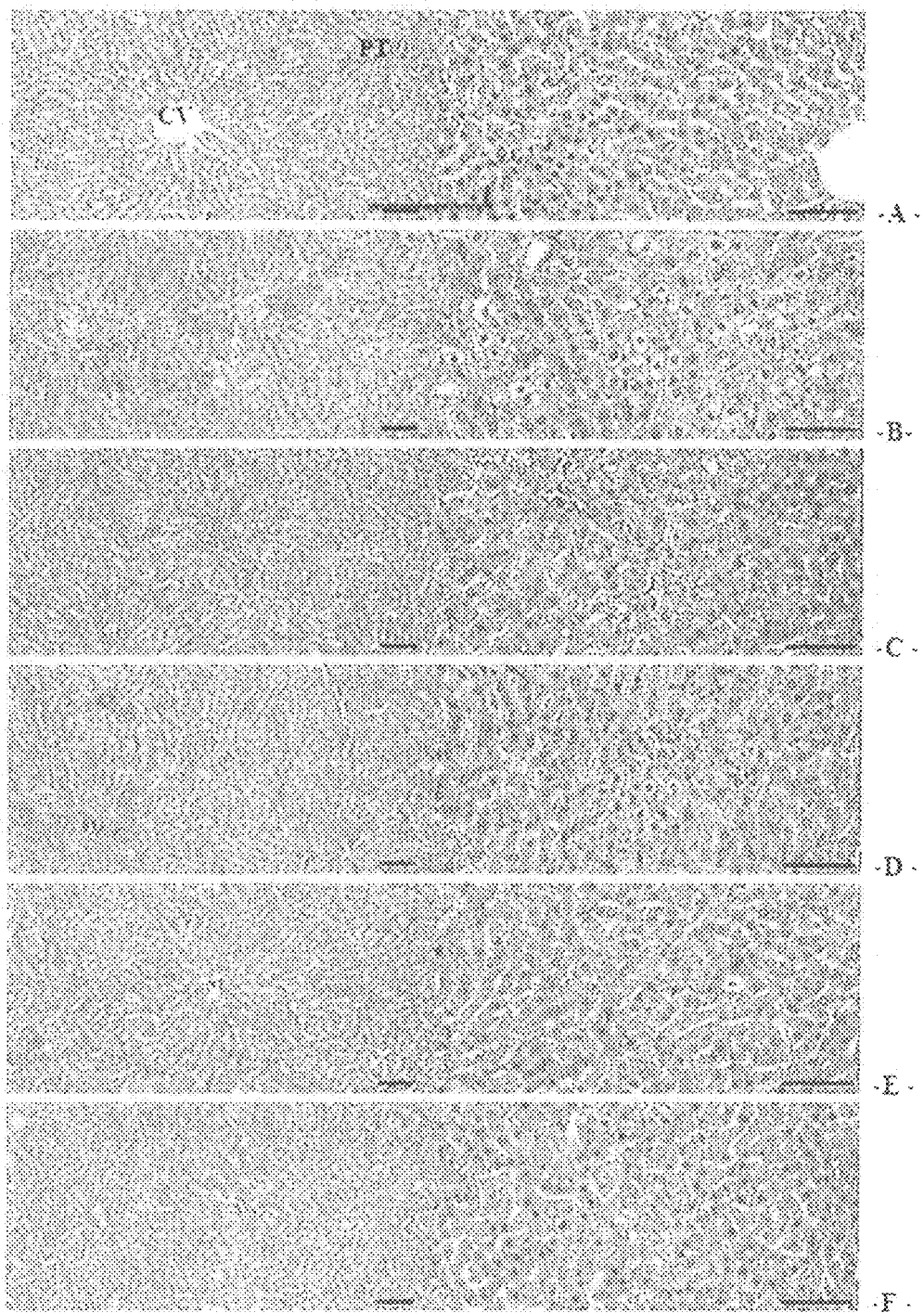
FIG. 14 shows a histological profile of left lateral lobes of livers taken from sham control or OVX rats. A shows sham control, B shows OVX control, C shows red clover extract 40 mg/kg administered group, D shows pomegranate extract 20 mg/kg administered group, E shows red clover:pomegranate extract 2:1 mixture (g/g) 120 mg/kg administered group, F shows red clover:pomegranate extract 2:1 mixture (g/g) 60 mg/kg administered group. CV represents Central vein; PT represents Portal Triad.

Hepatic steatosis characterized by hypertrophy caused by remarkable fat deposition in hepatocytes occurred in OVX control, and significant (p<0.01) increases in region with hepatic fatty degeneration and mean hepatocyte diameter were each found in OVX control as compared to sham control, while significant (p<0.01 or p<0.05) decreases in hepatic steatosis were each found in all test substance administered groups including red clover extract 40 mg/kg administered groups as compared to OVX control, and particularly, significant (p<0.01) decreases in region with hepatic fatty degeneration and mean hepatocyte diameter were found in red clover:pomegranate extract 2:1 (g/g) mixture 120 and 60 mg/kg administered groups as compared to each of red clover extract 40 mg/kg and pomegranate extract 20 mg/kg administered groups (Table 11, FIG. 14).

The region with hepatic fatty degeneration and mean hepatocyte diameter changed by 1001.19 and 152.94% respectively in OVX control as compared to normal control, and red clover extract 40 mg/kg, pomegranate extract 20 mg/kg, red clover:pomegranate extract 2:1 (g/g) mixture 120, 60 mg/kg administered groups had changes in region with hepatic fatty degeneration by −38.93, −29.44, −65.97, −59.16% respectively, and changes in mean hepatocyte diameter by −20.83, −19.11, −45.46, −35.65% respectively, as compared to OVX control.

TABLE 11

| Groups | Control | | References | | RC:PCP 2:1 mixture(g/g) | |
|---|---|---|---|---|---|---|
| | Sham | OVX | RC 40 mg/kg | PCP 20 mg/kg | 120 mg/kg | 60 mg/kg |
| Fat pads | | | | | | |
| Total Th (mm) | 4.43 ± 0.92 | 9.85 ± 1.60$^a$ | 7.70 ± 1.01$^{ac}$ | 8.02 ± 0.54$^{ac}$ | 5.55 ± 0.71$^{bcdf}$ | 6.37 ± 0.57$^{acef}$ |
| Adipocyte DM (μm) | 82.20 ± 12.37 | 158.17 ± 19.42$^a$ | 117.50 ± 14.07$^{ac}$ | 127.82 ± 15.14$^{ac}$ | 99.03 ± 10.07$^{bcef}$ | 101.74 ± 11.48$^{acef}$ |
| Uterus | | | | | | |
| Total Th (mm) | 3.21 ± 0.65 | 0.54 ± 0.11$^h$ | 0.89 ± 0.10$^{hi}$ | 0.73 ± 0.09$^{hi}$ | 1.45 ± 0.36$^{hikl}$ | 1.10 ± 0.10$^{hikl}$ |
| Epl Th (μm) | 38.47 ± 5.18 | 9.76 ± 2.26$^a$ | 16.90 ± 1.51$^{ac}$ | 19.16 ± 1.72$^{ac}$ | 24.28 ± 2.31$^{acdf}$ | 22.81 ± 2.02$^{acdg}$ |
| Mucosa Th (μm) | 967.28 ± 220.32 | 176.98 ± 21.58$^h$ | 227.65 ± 31.82$^{hi}$ | 261.87 ± 32.06$^{hi}$ | 484.97 ± 56.84$^{hikl}$ | 420.77 ± 94.19$^{hikl}$ |
| UG percentage (%) | 28.78 ± 4.83 | 4.85 ± 2.17$^a$ | 9.28 ± 1.53$^{ac}$ | 11.03 ± 3.19$^{ac}$ | 20.10 ± 3.13$^{acdf}$ | 17.67 ± 2.71$^{acdf}$ |
| Liver | | | | | | |
| FC region (%) | 4.74 ± 3.02 | 52.14 ± 11.22$^a$ | 31.84 ± 4.83$^{ac}$ | 39.79 ± 7.25$^{ac}$ | 17.74 ± 4.16$^{acdf}$ | 21.29 ± 4.91$^{acdf}$ |
| Hepatocyte DM (μm) | 12.81 ± 1.30 | 32.39 ± 5.08$^h$ | 25.65 ± 2.24$^{hi}$ | 26.20 ± 2.16$^{hj}$ | 17.67 ± 3.20$^{hikl}$ | 20.85 ± 2.27$^{hikl}$ |

$^a$p < 0.01 and $^b$p < 0.05: comparison with sham control according to LSD test
$^c$p < 0.01: comparison with OVX control according to LSD test
$^d$p < 0.01 and $^e$p < 0.05: comparison with red clover extract 40 mg/kg administered group according to LSD test
$^f$p < 0.01 and $^g$p < 0.05: comparison with pomegranate extract 20 mg/kg administered group according to LSD test
$^h$p < 0.01: comparison with sham control according to MW test
$^i$p < 0.01 and $^j$p < 0.05: comparison with OVX control according to MW test
$^k$p < 0.01: comparison with red clover extract 40 mg/kg administered group according to MW test
$^l$p < 0.01: comparison with pomegranate extract 20 mg/kg administered group according to MW test Abbreviations in Table 11 are as follows:
Th=thickness,
DM=diameter,
Epi=epithelium,
UG=uterine gland,
FC=fatty change.

Example 1-17. Histological Change (2): Femur, Tibia and Lumbar Vertebrae (L4)

Figure 15:
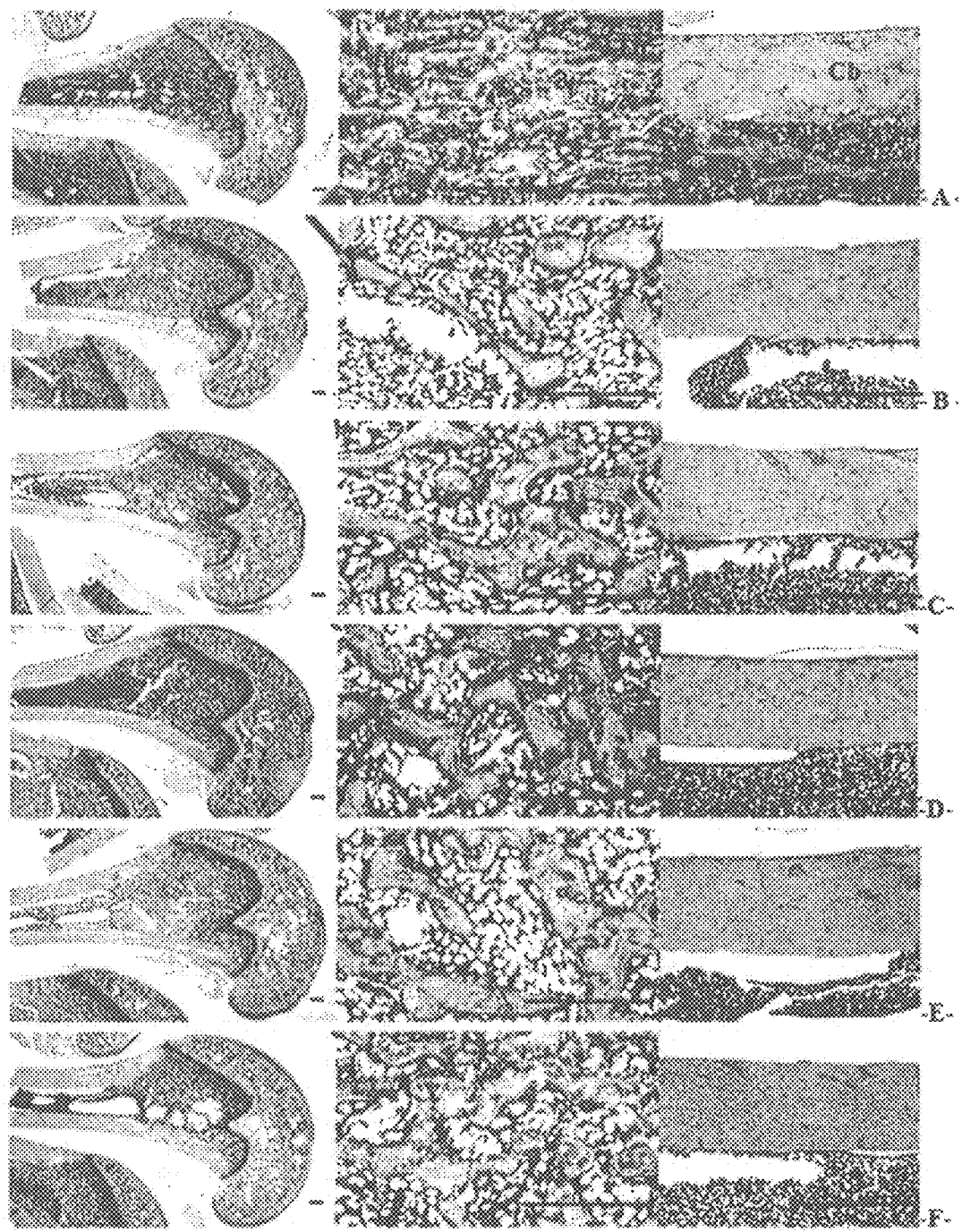
FIG. 15 shows a histological profile of femurs taken from sham control or OVX rats. A shows sham control, B shows OVX control, C shows red clover extract 40 mg/kg administered group, D shows pomegranate extract 20 mg/kg administered group, E shows red clover:pomegranate extract 2:1 mixture (g/g) 120 mg/kg administered group, F shows red clover:pomegranate extract 2:1 mixture (g/g) 60 mg/kg administered group. Cb represents cortical bone; Tb represents trabecular bone; Bm represents bone marrow; Gp represents growth plate.
Figure 16:
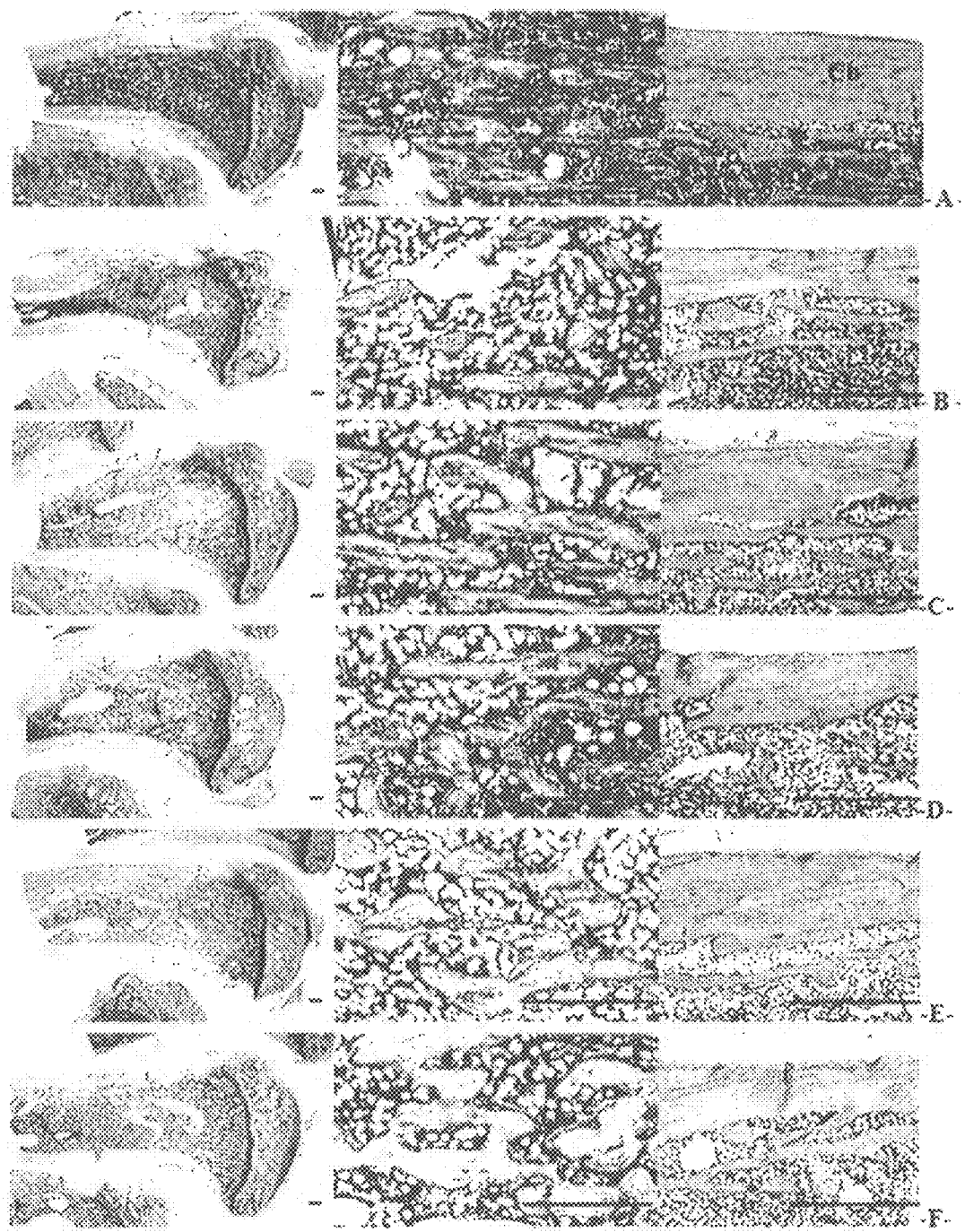
FIG. 16 shows a histological profile of tibiae taken from sham control or OVX rats. A shows sham control, B shows OVX control, C shows red clover extract 40 mg/kg administered group, D shows pomegranate extract 20 mg/kg administered group, E shows red clover:pomegranate extract 2:1 mixture (g/g) 120 mg/kg administered group, F shows red clover:pomegranate extract 2:1 mixture (g/g) 60 mg/kg administered group. Cb represents cortical bone; Tb represents trabecular bonem; Bm represents bone marrow; Gp represents growth plate.
Figure 17:
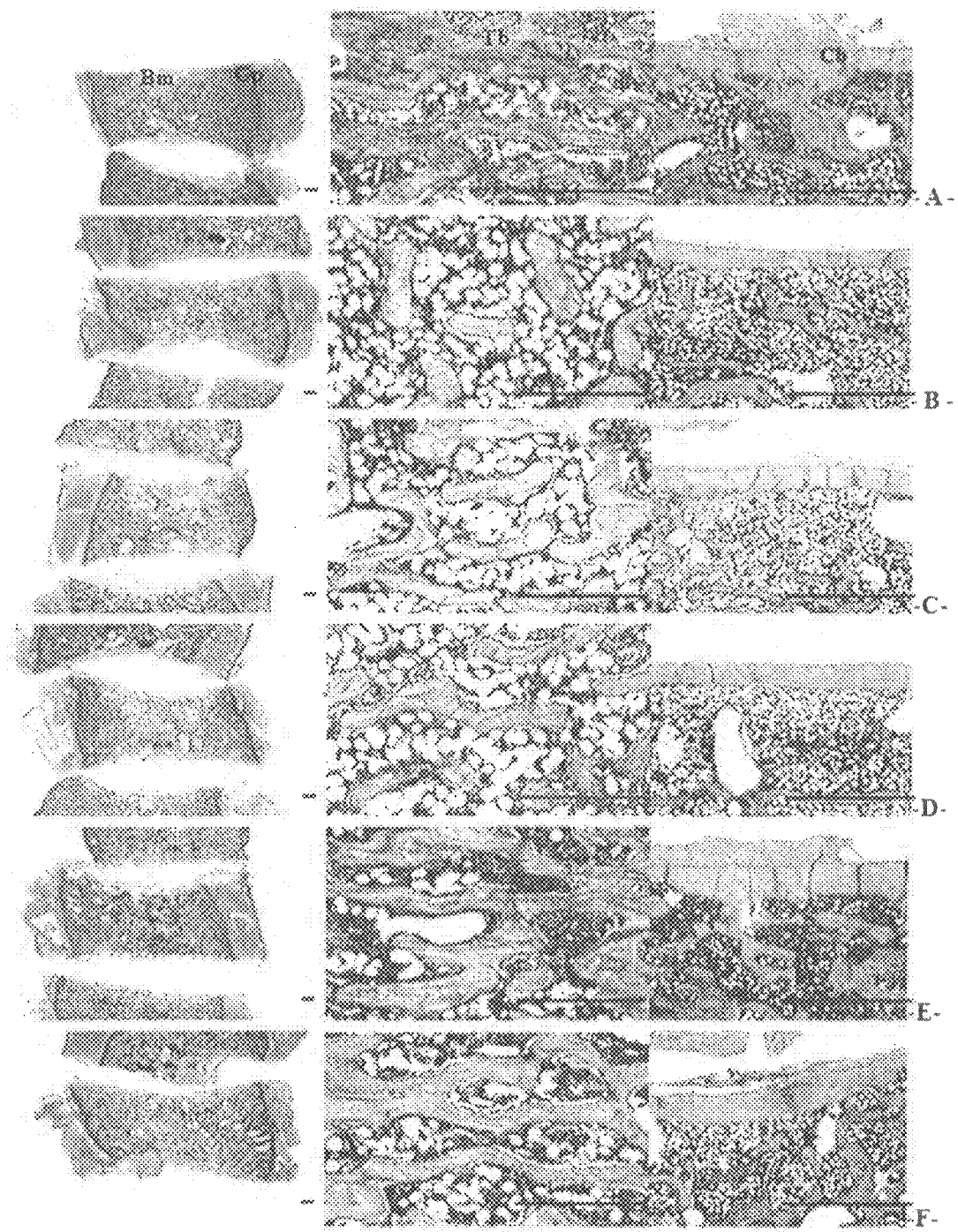
FIG. 17 shows a histological profile of L4 taken from sham control or OVX rats. A shows sham control, B shows OVX control, C shows red clover extract 40 mg/kg administered group, D shows pomegranate extract 20 mg/kg administered group, E shows red clover:pomegranate extract 2:1 mixture (g/g) 120 mg/kg administered group, F shows red clover:pomegranate extract 2:1 mixture (g/g) 60 mg/kg administered group. Cb represents cortical bone; Tb represents trabecular bonem; Bm represents bone marrow; Gp represents growth plate.

Trabecular bone and cortical bone developed relatively well were observed in femur, tibia and L4 of sham operated group, while remarkable histological decreases of trabecular bone and cortical bone caused by remarkable increases in number and activity of osteoclast cells were found in OVX control, but remarkable increases in bone mass and thickness of trabecular bone and cortical bone caused by osteoclast cell activity inhibition of femur, tibia and L4 were found in all test substance administered groups including pomegranate extract 20 mg/kg administered groups, and particularly, red clover:pomegranate extract 2:1 (g/g) mixture 120 and 60 mg/kg administered groups had remarkable osteoclast cell activity inhibition and bone mass preservation effects as compared to each of red clover extract 40 mg/kg and pomegranate extract 20 mg/kg administered groups (Tables 12-14, FIGS. 15-17).

(1) Bone Mass and Structure

In the case of OVX control, each of the trabecular bone mass, mean trabecular bone length, thickness and number, and mid-shaft region conical bone thickness of femur, tibia and L4 significantly ($p<0.01$) decreased as compared to sham control, while significant ($p<0.01$ or $p<0.05$) increases in trabecular bone mass, mean trabecular bone length, thickness and number, and conical bone thickness of femur, tibia and L4 were found in all candidate substance administered groups including red clover:pomegranate extract 2:1 (g/g) mixture administered groups as compared to OVX control, and particularly, red clover:pomegranate extract 2:1 (g/g) mixture 120 and 60 mg/kg administered group had a remarkable effect on inhibition of reduction in histological markers of bone mass and structure as compared to each of red clover extract 40 mg/kg and pomegranate extract 20 mg/kg administered groups.

In the case of OVX control, the trabecular bone mass and mid-shaft cortical bone thickness of femur changed by −66.40% and −25.69% respectively as compared to sham control, and red clover extract 40 mg/kg, pomegranate extract 20 mg/kg, red clover:pomegranate extract 2:1 (g/g) mixture 120, 60 mg/kg administered groups had changes in trabecular bone mass by 43.75, 20.91, 111.04, 82.21% respectively, and changes in cortical bone thickness by 17.00, 14.54, 27.73, 24.76% respectively, as compared to OVX control.

In the case of OVX control, the trabecular bone mass and mid-shaft cortical bone thickness of tibia changed by −63.65 and −46.83% respectively as compared to sham control, and red clover extract 40 mg/kg, pomegranate extract 20 mg/kg, red clover:pomegranate extract 2:1 (g/g) mixture 120, 60 mg/kg administered groups had changes in trabecular bone mass by 35.78, 23.25, 101.87, 72.78% respectively, and changes in cortical bone thickness by 16.05, 11.62, 58.61, 29.80% respectively as compared to OVX control.

In the case of OVX control, the trabecular bone mass and mid-shaft cortical bone thickness of L4 changed by −44.84 and −38.59% respectively as compared to sham control, and red clover extract 40 mg/kg, pomegranate extract 20 mg/kg, red clover:pomegranate extract 2:1 (g/g) mixture 120, 60 mg/kg administered groups had changes in trabecular bone mass by 30.88, 24.90, 56.05, 44.72% respectively, and changes in cortical bone thickness by 23.16, 17.86, 40.78, 39.53% respectively, as compared to OVX control.

(2) Bone Resorption

In the case of OVX control, each of the osteoclast cell number and ratio (OS/BS) of femur, tibia and L4 significantly ($p<0.01$) increased as compared to sham control, while remarkable decreases in osteoclast cell number and OS/BS of femur, tibia and L4 were found in all candidate substance administered groups as compared to OVX control, and particularly, red clover:pomegranate extract 2:1 (g/g) mixture 120 and 60 mg/kg administered groups had a remarkable effect on inhibition of bone resorption increase as compared to each of red clover extract 40 mg/kg and pomegranate extract 20 mg/kg administered groups (Tables 12-14).

In the case of OVX control, the osteoclast cell number and OS/BS of femur changed by 280.30 and 229.41% respectively as compared to case sham control, and red clover extract 40 mg/kg, pomegranate extract 20 mg/kg, red clover:pomegranate extract 2:1 (g/g) mixture 120, 60 mg/kg administered groups had changes in osteoclast cell number by −37.05, −30.28, −60.16, −52.59% respectively, and changes in OS/BS by −21.94, −10.44, −44.78, −35.85% respectively, as compared to OVX control.

In the case of OVX control, the osteoclast cell number and OS/BS of tibia changed by 145.69 and 351.02% respectively as compared to sham control, and red clover extract 40 mg/kg, pomegranate extract 20 mg/kg, red clover:pomegranate extract 2:1 (g/g) mixture 120, 60 mg/kg administered groups had changes in osteoclast cell number by −29.82, −23.86, −44.21, −37.89% respectively, and changes in OS/BS −24.34, −17.04, −68.83, −51.81% respectively, as compared to OVX control.

In the case of OVX control, the osteoclast cell number and OS/BS of L4 changed by 188.89 and 254.62% respectively as compared to sham control, and red clover extract 40 mg/kg, pomegranate extract 20 mg/kg, red clover:pomegranate extract 2:1 (g/g) mixture 120, 60 mg/kg administered groups had changes in osteoclast cell number by −18.68, −13.19, −52.75, −45.60% respectively, and changes in OS/BS by −21.41, −16.01, −62.69, −54.16% respectively, as compared to OVX control.

TABLE 12

| Groups | Control | | References | | RC:PCP 2:1 mixture (g/g) | |
|---|---|---|---|---|---|---|
| | Sham | OVX | RC 40 mg/kg | PCP 20 mg/kg | 120 mg/kg | 60 mg/kg |
| Bone mass and structure | | | | | | |
| TBV, BV/TV | 47.27 ± 11.66 | 15.88 ± 2.97$^h$ | 22.83 ± 2.96$^{hj}$ | 19.20 ± 1.70$^{hj}$ | 33.52 ± 6.51$^{hjlm}$ | 28.94 ± 2.85$^{hjlm}$ |
| Tbn | 23.00 ± 3.07 | 11.38 ± 1.92$^a$ | 16.00 ± 2.27$^{ac}$ | 15.63 ± 1.69$^{ac}$ | 20.50 ± 0.93$^{bcdf}$ | 18.38 ± 1.30$^{acef}$ |
| Tbl | 6.81 ± 1.68 | 1.99 ± 0.21$^h$ | 3.42 ± 0.49$^{hj}$ | 3.08 ± 0.90$^{hj}$ | 5.78 ± 0.42$^{jlm}$ | 5.08 ± 0.25$^{hjlm}$ |
| Tbt | 144.33 ± 11.68 | 90.54 ± 15.24$^a$ | 112.08 ± 11.01$^{ac}$ | 104.83 ± 7.23$^{ac}$ | 133.80 ± 8.50$^{bcdf}$ | 124.82 ± 6.89$^{acef}$ |
| Cbt-shaft | 848.67 ± 91.46 | 630.65 ± 103.16$^h$ | 737.86 ± 49.96$^{hj}$ | 722.33 ± 20.24$^{hj}$ | 805.56 ± 37.42$^{jlm}$ | 786.77 ± 22.00$^{jlm}$ |

TABLE 12-continued

| Groups | Control | | References | | RC:PCP 2:1 mixture (g/g) | |
|---|---|---|---|---|---|---|
| | Sham | OVX | RC 40 mg/kg | PCP 20 mg/kg | 120 mg/kg | 60 mg/kg |
| Bone resorption | | | | | | |
| Ocn | 8.35 ± 2.38 | 31.38 ± 6.02$^h$ | 19.75 ± 2.31$^{hj}$ | 21.88 ± 3.00$^{hj}$ | 12.50 ± 2.62$^{hjlm}$ | 14.88 ± 2.23$^{hjlm}$ |
| OS/BS | 4.28 ± 1.58 | 14.09 ± 1.96$^a$ | 11.00 ± 0.95$^{ac}$ | 12.62 ± 1.69$^a$ | 7.78 ± 1.32$^{acdf}$ | 9.04 ± 1.35$^{acef}$ |

$^a$p < 0.01 and $^b$p < 0.05: comparison with sham control according to LSD test
$^c$p < 0.01: comparison with OVX control according to LSD test
$^d$p < 0.01 and $^e$p < 0.05: comparison with red clover extract 40 mg/kg administered group according to LSD test
$^f$p < 0.01 and $^g$p < 0.05: comparison with pomegranate extract 20 mg/kg administered group according to LSD test
$^m$p < 0.01: comparison with pomegranate extract 20 mg/kg administered group according to MW test
$^h$p < 0.01 and $^i$p < 0.05: comparison with sham control according to MW test
$^j$p < 0.01 and $^k$p < 0.05: comparison with OVX control according to MW test
$^l$p < 0.01: comparison with red clover extract 40 mg/kg administered group according to MW test

TABLE 13

| Groups | Control | | References | | RC:PCP 2:1 mixture (g/g) | |
|---|---|---|---|---|---|---|
| | Sham | OVX | RC 40 mg/kg | PCP 20 mg/kg | 120 mg/kg | 60 mg/kg |
| Bone mass and structure | | | | | | |
| TBV, BV/TV | 52.14 ± 5.29 | 18.95 ± 2.79$^g$ | 25.73 ± 2.74$^{gi}$ | 23.36 ± 2.47$^{gi}$ | 38.26 ± 8.22$^{gikm}$ | 32.75 ± 5.50$^{gikm}$ |
| Tbn | 36.13 ± 6.47 | 11.13 ± 1.36$^g$ | 14.63 ± 1.60$^{gi}$ | 14.38 ± 2.26$^{gi}$ | 23.13 ± 2.53$^{gikm}$ | 22.00 ± 2.00$^{gikm}$ |
| Tbl | 7.41 ± 0.74 | 2.34 ± 0.52$^a$ | 3.28 ± 0.49$^{ac}$ | 2.98 ± 0.19$^{ad}$ | 5.23 ± 0.76$^{bcef}$ | 4.36 ± 0.63$^{acef}$ |
| Tbt | 124.58 ± 12.32 | 77.05 ± 5.96$^a$ | 94.69 ± 13.44$^{ac}$ | 91.32 ± 14.36$^{ad}$ | 115.76 ± 14.42$^{cef}$ | 112.71 ± 12.97$^{bcef}$ |
| Cbt-shaft | 813.67 ± 87.66 | 432.65 ± 32.47$^g$ | 502.08 ± 53.06$^{gi}$ | 482.92 ± 31.92$^{gi}$ | 686.23 ± 66.91$^{hikm}$ | 561.55 ± 37.01$^{gilm}$ |
| Bone resorption | | | | | | |
| Ocn | 14.50 ± 2.20 | 35.63 ± 5.68$^a$ | 25.00 ± 2.00$^{ac}$ | 27.13 ± 3.40$^a$ | 19.88 ± 3.64$^{acef}$ | 22.13 ± 2.53$^{acf}$ |
| OS/BS | 6.49 ± 1.31 | 29.28 ± 3.21$^g$ | 22.16 ± 1.62$^{gi}$ | 24.29 ± 3.70$^{gi}$ | 9.31 ± 1.34$^{gikm}$ | 14.11 ± 4.38$^{gikm}$ |

$^a$p < 0.01 and $^b$p < 0.05: comparison with sham control according to LSD test
$^c$p < 0.01 and $^d$p < 0.05: comparison with OVX control according to LSD test
$^e$p < 0.01: comparison with red clover extract 40 mg/kg administered group according to LSD test
$^f$p < 0.01: comparison with pomegranate extract 20 mg/kg administered group according to LSD test
$^g$p < 0.01 and $^h$p < 0.05: comparison with sham control according to MW test
$^i$p < 0.01 and $^j$p < 0.05: comparison with OVX control according to MW test
$^k$p < 0.01 and $^l$p < 0.05: comparison with red clover extract 40 mg/kg administered group according to MW test
$^m$p < 0.01: comparison with pomegranate extract 20 mg/kg administered group according to MW test

TABLE 14

| Groups | Control | | References | | RC:PCP 2:1 mixture (g/g) | |
|---|---|---|---|---|---|---|
| | Sham | OVX | RC 40 mg/kg | PCP 20 mg/kg | 120 mg/kg | 60 mg/kg |
| Bone mass and structure | | | | | | |
| TBV, BV/TV | 56.33 ± 5.80 | 31.07 ± 2.17$^a$ | 40.67 ± 2.21$^{ac}$ | 38.81 ± 3.14$^{ad}$ | 48.49 ± 5.58$^{aceg}$ | 44.97 ± 3.01$^{acfg}$ |
| Tbn | 24.50 ± 4.00 | 10.88 ± 2.10$^i$ | 14.88 ± 1.55$^{ik}$ | 13.38 ± 1.51$^{il}$ | 19.88 ± 2.17$^{jkmo}$ | 17.25 ± 1.49$^{ikmo}$ |
| Tbl | 4.45 ± 0.47 | 2.32 ± 0.33$^i$ | 2.89 ± 0.33$^{ik}$ | 2.82 ± 0.17$^{il}$ | 3.89 ± 0.23$^{jkmo}$ | 3.66 ± 0.44$^{ikmo}$ |
| Tbt | 148.78 ± 14.67 | 109.21 ± 12.86$^i$ | 125.25 ± 6.43$^{il}$ | 124.18 ± 6.91$^{il}$ | 136.42 ± 6.01$^{ikmo}$ | 132.19 ± 2.27$^{ikp}$ |
| Cbt-shaft | 233.01 ± 32.31 | 143.10 ± 19.90$^a$ | 176.25 ± 15.35$^{ac}$ | 168.67 ± 9.71$^{ad}$ | 201.46 ± 11.24$^{acfg}$ | 199.67 ± 15.11$^{acfg}$ |
| Bone resorption | | | | | | |
| Ocn | 7.88 ± 1.89 | 22.75 ± 2.76$^a$ | 18.50 ± 3.07$^{ac}$ | 19.75 ± 1.49$^{ad}$ | 10.75 ± 1.67$^{bceg}$ | 12.38 ± 1.30$^{aceg}$ |
| OS/BS | 5.75 ± 0.93 | 20.40 ± 2.67$^a$ | 16.03 ± 2.06$^{ac}$ | 17.13 ± 1.55$^{ac}$ | 7.61 ± 1.54$^{ceg}$ | 9.35 ± 1.26$^{aceg}$ |

$^a$p < 0.01 and $^b$p < 0.05: comparison with sham control according to LSD test
$^c$p < 0.01 and $^d$p < 0.05: comparison with OVX control according to LSD test
$^e$p < 0.01 and $^f$p < 0.05: comparison with red clover extract 40 mg/kg administered group according to LSD test
$^g$p < 0.01 and $^h$p < 0.05: comparison with pomegranate extract 20 mg/kg administered group according to LSD test
$^i$p < 0.01 and $^j$p < 0.05: comparison with sham control according to MW test
$^k$p < 0.01 and $^l$p < 0.05: comparison with OVX control according to MW test
$^m$p < 0.01 and $^n$p < 0.05: comparison with red clover extract 40 mg/kg administered group according to MW test
$^o$p < 0.01 and $^p$p < 0.05: comparison with pomegranate extract 20 mg/kg administered group according to MW test For reference, what is meant by abbreviations in Tables 12-14 is as follows:

Cbt=Cortical bone thickness (Cross thickness; μm),
Tbl=Trabecular bone length (Longitudinal thickness; mm),
Tbn=Trabecular bone number (N/epiphyseal),
Tbt=Trabecular bone thickness (Cross thickness; μm),
TV/BV=Trabecular bone mass (%),
OS/BS=Osteoclast cell surface/bone surface (%),
Ocn=Osteoclast cell number (N/epiphyseal).

Summary of Example 1

In the study, the effect of the mixture including the composite extract of pomegranate and red clover in enhancing bioactivity against menopausal disorders was evaluated using OVX Rat model that is known to be similar to menopausal disorders after human menopause [Tominaga et al., 2001, 2002; Iwamoto et al., 2005; Cheng and Tian, 2012].

That is, from 28 days after OVX, red clover extract 40 mg/kg, pomegranate extract 20 mg/kg, and red clover:pomegranate extract 2:1 (g/g) mixture 120, 60 mg/kg were dissolved in or diluted with sterile distilled water and orally administered at a dose of 5 ml/kg once daily for 84 days (12 weeks; 3 months), and evaluation was conducted based on 5 pharmacological effects including an estrogen-like effect, an anti-obesity effect, a hyperlipidemia inhibitory effect, a protective effect against fatty liver, and an osteoporosis inhibitory effect.

To evaluate the estrogen-like effect and anti-obesity effect, changes in body weight and body weight gain, water and food consumption, urine volume and fecal excretion, serum estradiol level, and weights of abdominal fat pad and uterus, and changes in abdominal fat pad thickness and mean adipocyte diameter, thickness of uterus total, epithelium and mucosa, and percentage of uterine glands in the mucosa were each evaluated. Furthermore, the liver protective effect against fatty liver was evaluated by measuring changes in liver weight, serum AST and ALT levels, mean hepatocyte diameter and region with hepatic degeneration showing fatty change, the hyperlipidemia reduction effect was evaluated using changes in serum total cholesterol (TC), low-density lipoprotein (LDL), high-density lipoprotein (HDL) and triglyceride (TG) levels, and to evaluate the osteoporosis reduction effect, namely, the bone protective effect, histological changes in wet, dry and ash weights, bone mineral density (BMD), bone strength, serum osteocalcin and bone specific alkaline phosphatase (bALP) levels, bone mass and structure and bone resorption of femur, tibia and lumbar vertebrae were each measured. In the experiment, evaluation was conducted by comparing the results of red clover:pomegranate extract 2:1 (g/g) mixture to the results in rats administered with each of red clover extract 40 mg/kg and pomegranate extract 20 mg/kg.

As a result of the experiment, remarkable increases in body weight and body weight gain, food and water consumption, abdominal fat pad weight, and serum AST, ALT, TC, LDL, TG and osteocalcin levels as well as remarkable decreases in uterus, liver, femur, tibia and L5 weights, serum bALP, and estradiol levels were found in OVX control as compared to sham vehicle control, and indication of remarkable increases in abdominal wall fat pad thickness, hypertrophy of adipocytes, hepatic steatosis, disuse atrophy of uterus, and reductions in bone mass and structure of femur, tibia and L4 was each histologically and histomorphometrically detected together with remarkable increases of bone resorption marker (Ocn and OS/BS). That is, a variety of disorders such as obesity, hyperlipidemia, hepatic steatosis and osteoporosis were induced by OVX. On the other hand, signs of disorders induced by OVX were remarkably inhibited by continuous oral administration of red clover:pomegranate extract 2:1 (g/g) mixture 120, 60 mg/kg for 84 days. Particularly, red clover:pomegranate extract 2:1 (g/g) mixture 120 and 60 mg/kg administered groups had a significant effect on reduction of disorders induced by OVX such as obesity, hyperlipidemia, hepatic steatosis and osteoporosis as compared to each of red clover extract 40 mg/kg and pomegranate extract 20 mg/kg administered groups. Accordingly, the addition of the pomegranate extract (red clover:pomegranate extract 2:1 (g/g) mixture) at an optimal ratio is expected to synergistically increase an effect of red clover extract on reduction of OVX induced menopausal disorders through the increased diversity of isoflavonoid contained, but the present disclosure is not limited thereto.

In the study, food and water consumption remarkably increased without any significant change in urine and fecal excretion due to OVX, resulting in remarkable increases in body weight and deposition of abdominal wall fat and hypertrophy of adipocytes. On the other hand, signs of obesity induced by OVX were remarkably inhibited by continuous oral administration of each of red clover extract 40 mg/kg, pomegranate extract 20 mg/kg, red clover:pomegranate extract 2:1 (g/g) mixture 120, 60 mg/kg for 84 days, and particularly, red clover:pomegranate extract 2:1 (g/g) mixture 120 and 60 mg/kg administered groups had presumably significant inhibition of increases in body fat deposition and body weight as compared to each of red clover extract 40 mg/kg and pomegranate extract 20 mg/kg administered groups. Furthermore, remarkable increases in urine volume and fecal excretion (28, 49 and 83 days after start of administration) when measured were each found in red clover:pomegranate extract 2:1 (g/g) mixture 120 and 60 mg/kg administered rats as compared to each of red clover extract 40 mg/kg and pomegranate extract 20 mg/kg administered rats. These results serve as an evidence demonstrating that the addition of pomegranate extract at an optimal ratio (red clover:pomegranate extract 2:1 (g/g) mixture) synergistically increases an effect of red clover extract on reduction of obesity, and red clover:pomegranate extract 2:1 (g/g) mixture 120 and 60 mg/kg is thought to have very effective activities on obesity through increased peristalsis of a digestive tract and a diuretic effect together with an estrogenic effect through regulation of CCK [Asarian and Geary, 2007; Thammacharoen et al., 2008] and glucagon [Geary and Asarian, 2001] generally known as digestive hormones related to satiety of isoflavonoid, but the present disclosure is not limited thereto. Generally, it is known that as peristalsis of the digestive tract increases, fecal excretion increases, leading to an anti-obesity effect such as body weight decrease [Hyland et al., 2010; Bertrand et al., 2011; Snedeker and Hay, 2012], and a diuretic effect also produces a similar body weight decrease effect [Dagnault et al., 1996; Verlander et al., 1998].

In the experiment results, due to OVX, significant decreases in uterus weight occurred, and histopathologically remarkable decreases in not only uterus total, mucosa and epithelium thickness but also uterine glands in the mucosa occurred. On the other hand, indication of endometrial atrophy was remarkably inhibited by oral administration of each of red clover extract 40 mg/kg, pomegranate extract 20 mg/kg, red clover:pomegranate extract 2:1 (g/g) mixture 120, 60 mg/kg, and particularly, red clover:pomegranate extract 2:1 (g/g) mixture 120 and 60 mg/kg administered groups showed presumably significant inhibition of endometrial atrophy as compared to each of red clover extract 40 mg/kg and pomegranate extract 20 mg/kg administered groups.

In the study results, the serum TC, LDL and TG levels were remarkably decreased and the HDL level was remarkably increased by oral administration of red clover extract 40 mg/kg, pomegranate extract 20 mg/kg, red clover:pomegranate extract 2:1 (g/g) mixture 120, 60 mg/kg, and particularly, red clover:pomegranate extract 2:1 (g/g) mixture 120 and 60 mg/kg administered groups had a significant anti-hyperlipidemia effect as compared to each of red clover extract 40 mg/kg and pomegranate extract 20 mg/kg administered group, and it is determined that the addition of pomegranate extract at a ratio according to the present disclosure synergistically increases an anti-hyperlipidemia effect of red clover extract at least under the experimental conditions, and the anti-hyperlipidemia effect will be transferred via HMG-CoA, the enzyme involved in cholesterol synthesis [Di Croce et al., 1996].

In the study, remarkable hepatic steatosis in OVX control was each bio-chemically and histologically ascertained. On the other hand, signs of fatty liver induced by OVX were remarkably inhibited by oral administration of each of red clover extract 40 mg/kg, pomegranate extract 20 mg/kg, red clover:pomegranate extract 2:1 (g/g) mixture 120, 60 mg/kg, and particularly, red clover:pomegranate extract 2:1 (g/g) mixture 120 and 60 mg/kg administered groups had a significant liver protective effect as compared to each of red clover extract 40 mg/kg and pomegranate extract 20 mg/kg administered groups. These results also serve as an evidence demonstrating that a liver protective effect of a mixture of pomegranate extract and red clover extract at an optimal ratio synergistically increases. As a result of the experiment, remarkable increases in serum osteocalcin level as well as decreases in femur, tibia and L5 weights and serum bALP level were found in OVX control as compared to sham vehicle control, and indication of decreases in bone mass and structure of femur, tibia and L4 as well as remarkable increases of bone resorption marker (Ocn and OS/BS) was each histologically and histomorphometrically ascertained, so it was observed that osteoporosis was induced by OVX. On the other hand, signs of osteoporosis were remarkably inhibited by continuous oral administration of each of red clover extract 40 mg/kg, pomegranate extract 20 mg/kg, red clover:pomegranate extract 2:1 (g/g) mixture 120, 60 mg/kg for 84 days, and particularly, red clover:pomegranate extract 2:1 (g/g) mixture 120 and 60 mg/kg administered groups had a significant osteoporosis reduction effect as compared to each of red clover extract 40 mg/kg and pomegranate extract 20 mg/kg administered groups. Accordingly, it was observed that a mixture of pomegranate extract and red clover extract at a ratio according to the present disclosure synergistically increased an osteoporosis reduction effect.

2. Study about Setting of a Mixture Ratio of a Pomegranate Extract and a Red Clover Extract Example 2-1. Experimental Animal and Experimental Method (1) Experimental Animal Female virgin Sprague-Dawley Rats (6 weeks old) were purchased, all experimental animals except sham control were randomly selected and underwent bilateral ovariectomy to induce menopause. On the other hand, in sham group, both ovaries were detected by the same method but incisions were not made, and abdominal cavities were closed again. At 28 days after surgery, based on body weights (OVX rats: 312.21±12.3 g, sham operated rats: 255.12±12.11 g), 4 mice per group were selected from all experimental animals and used for experiments.

(2) Experimental Method

The effect on menopausal disorders was evaluated based on 3 pharmacological effects including an anti-obesity effect, a hyperlipidemia inhibitory effect and an osteoporosis inhibitory effect.

The test material was suspended or dissolved in sterile distilled water, and orally administered at a dose of 5 ml/kg once daily for 56 days from the 28th day after OVX. Sham and OVX controls were orally administered with the vehicle, sterile distilled water alone instead of the test material at the same dose for the same period.

Changes in body weight were measured and recorded on the date of OVX surgery, 12 days before administration (27 days after OVX), the start date of administration, and the date of final sacrifice. The hyperlipidemia inhibitory effect was ascertained by measuring serum TC in blood taken at the time of final sacrifice, and the osteoporosis reduction effect was ascertained through BMD measurements of femur.

Example 2-2. Estrogen Activity Result in Proportion to Setting of a Mixture Ratio of a Pomegranate Extract and a Red Clover Extract To ascertain a synergistic effect of a mixture of red clover extract and pomegranate extract on a menopausal symptom relief effect in menopause induced model, 40 mg/kg of red clover extract intake was mixed with a pomegranate extract as in Table 1, and a synergistic effect of the added pomegranate extract on menopausal symptom relief was measured through an anti-obesity effect, a hyperlipidemia inhibitory effect and an osteoporosis inhibitory effect in menopause induced animal model.

As a result, the extent of menopausal symptom relief in menopause induced model through OVX was determined by oral administration of with a mixture of red clover extract (RC) 40 mg/kg and pomegranate extract (PCP) for 8 weeks.

In menopause induced model through OVX, changes in body weight increased by about 146 g, and when compared to red clover alone treated group, improvements were detected in the case in which a mixture including 10 mg/kg or higher of pomegranate extract was prescribed, and significant improvements were detected in 20 mg/kg or higher of pomegranate extract, but dose dependent improvements were not detected in a mixture including 40 mg/kg or higher of pomegranate extract.

Similar to changes in body weight, there was a significant improvement in BMD changes at 20 mg/kg or higher, but there was no dose dependent improvement.

As a result of measuring serum TC, there was a significant improvement at 10 mg/kg, but there was no dose dependent change between 80 mg/kg and 160 mg/kg.

It was seen from these results that significant improvements in menopause induced model were achieved by pomegranate extract (PCP) mixture administration than red clover extract (RC) alone administration, and dose dependent results were obtained at an optimal concentration of administration of 10~80 mg/kg.

Accordingly, in the case of preparing a mixture of 40~80 mg/kg of red clover extract with 10~80 mg/kg of pomegranate extract as formula for preparing a mixture of red clover extract (RC) and pomegranate extract (PCP), a synergistic effect was obtained.

3. Verification of a Synergistic Effect in Proportion to a Mixture Ratio of a Pomegranate Extract and a Red Clover Extract

Example 3-1. Experimental Animal and Experimental Method (1) Experimental Animal Female virgin ddY mice (6 weeks old, Kiwa Laboratory Animal, Wakayama, Japan) were used, and in the experiment, all experimental animals were handled according to the guidelines for animal ethics approved by the Animal Care and Ethics Committee of Daegu Haany University, and the experiment was done with prior approval. [Approval No. DHU2014-020]

(2) Experimental Method

Figure 18:
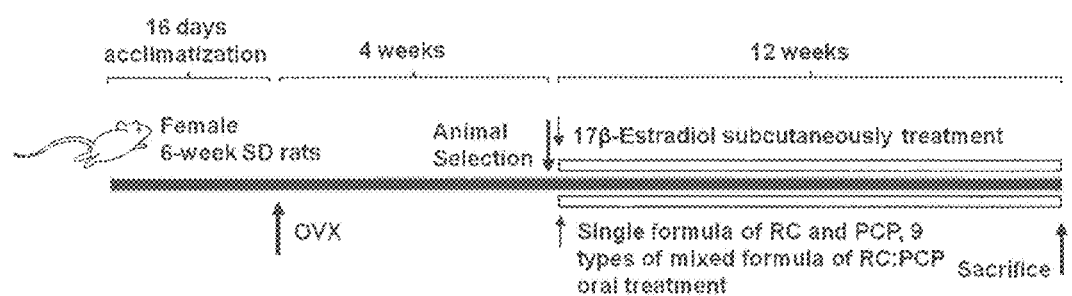
FIG. 18 shows a test schedule for testing a synergistic effect vs mixture ratio of a red clover extract and a pomegranate extract using OVX mice.

The experiment was performed after dividing the experimental animals into groups (total 14 groups; 8 mice per group). (Table 15, FIG. 18)

That is, the experiment was performed after dividing into sterile distilled water 10 ml/kg administered vehicle control after sham surgery (hereinafter sham control), sterile distilled water 10 ml/kg administered vehicle control after OVX surgery (hereinafter OVX control), pomegranate extract single formula 120 mg/kg administered group (PCP) after OVX, and 9 types of red clover:pomegranate extract mixed formula (g/g) administered groups after OVX surgery including red clover:pomegranate extract 1:1 (g/g) mixed formula 120 mg/kg administered group after OVX surgery (1-1), red clover:pomegranate extract 1:2 (g/g) mixed formula 120 mg/kg administered group after OVX surgery (1-2), red clover:pomegranate extract 1:4 (g/g) mixed formula 120 mg/kg administered group after OVX surgery (1-4), red clover:pomegranate extract 1:6 (g/g) mixed formula 120 mg/kg administered group after OVX surgery (1-6), red clover:pomegranate extract 1:8 (g/g) mixed formula 120 mg/kg administered group after OVX surgery (1-8), red clover:pomegranate extract 2:1 (g/g) mixed formula 120 mg/kg administered group after OVX surgery (2-1), red clover:pomegranate extract 4:1 (g/g) mixed formula 120 mg/kg administered group after OVX surgery (4-1), red clover:pomegranate extract 6:1 (g/g) mixed formula 120 mg/kg administered group after OVX surgery (6-1), and red clover:pomegranate extract 8:1 (g/g) mixed formula 120 mg/kg administered group after OVX surgery (8-1).

Optimal amounts of red clover extract or pomegranate extract were suspended or dissolved in sterile distilled water, and orally administered at a dose of 10 ml/kg once daily for 84 days from 28 days after OVX. That is, red clover extract and pomegranate extract single formula, and red clover:pomegranate extract 1:1, 1:2, 1:4, 1:6, 1:8, 2:1, 4:1, 6:1 and 8:1 (g/g) mixture 120 mg/kg were each orally administered for 84 days, and sham control and OVX control were orally administered with only sterile distilled water as a vehicle at the same dose for the same period instead of the test material, and according to earlier researchers' method [Chiba et al., 2003; Murakami et al., 2007; Tousen et al., 2011], 0.03 ug of 17β-estradiol (Sigma-Aldrich, St. Louise, Mo., USA) was dissolved in 0.2 ml of sterile saline, and subcutaneously administered to back skin at a dose of 0.2 ml/mouse (0.03 µg/head/day) once daily for 84 days from 28 days after OVX surgery (Table 15, FIG. 18). The administration dose of mixed formula was set higher 12 times than a human clinical dose of 600 mg, i.e., 600 mg/60 kg)× 12=120 mg/kg, in consideration of a body surface area of mouse, and the dose of each of red clover extract and pomegranate extract single formula was also set as 120 mg/kg for direct comparative evaluation of efficacy.

TABLE 15

| Group | Operation | Dose (mg/kg/day) | Animal No. |
|---|---|---|---|
| Selection of the Fittest Anti-climacterium Herbal Compositions on OVX Mice | | | |
| Control | Sham operate | Distilled water 10 ml/kg; once a day for 84 days | M01~M08 |
| Control | OVX operate | Distilled water 10 ml/kg; once a day for 84 days | M09~M16 |
| Reference | OVX operate | 17β-estradiol (0.03 µg/head); once a day for 84 days | M17~M24 |
| Reference | OVX operate | RC (120 mg/kg); once a day for 84 days | M25~M32 |
| Reference | OVX operate | PCP (120 mg/kg); once a day for 84 days | M33~M40 |
| Active | OVX operate | RC:PCP 1:1 (60:60 mg/kg); once a day for 84 days | M41~M48 |
| Active | OVX operate | RC:PCP 1:2 (40:80 mg/kg); once a day for 84 days | M49~M56 |
| Active | OVX operate | RC:PCP 1:4 (24:96 mg/kg); once a day for 84 days | M57~M64 |
| Active | OVX operate | RC:PCP 1:6 (17:103 mg/kg); once a day for 84 days | M65~M72 |
| Active | OVX operate | RC:PCP 1:8 (13:107 mg/kg); once a day for 84 days | M73~M80 |
| Active | OVX operate | RC:PCP 2:1 (80:40 mg/kg); once a day for 84 days | M81~M88 |
| Active | OVX operate | RC:PCP 4:1 (96:24 mg/kg); once a day for 84 days | M89~M96 |
| Active | OVX operate | RC:PCP 6:1 (103:17 mg/kg); once a day for 84 days | M97~M104 |
| Active | OVX operate | RC:PCP 8:1 (107:13 mg/kg); once a day for 84 days | M105~M112 |

OVX = Bilateral ovariectomy
PCP = Pomegranate Concentrate Powder
RC = Red clover dry extracts
RC:PCP = RC and PCP mixed formula (g/g)

For induction of menopausal disorders by OVX, an experiment was performed as follows.

That is, all experimental animals except sham control were randomly selected and underwent bilateral ovariectomy to induce estrogen deficient menopausal disorder. On the other hand, in sham operated group, both ovaries were detected by the same method but incisions were not made, and abdominal cavities were closed again. At 27 days after surgery, based on body weights (OVX mice: 30.71±1.65 g, 28.0-35.1 g; sham operated mice: 26.99±1.46 g, 24.4-28.7 g), 8 mice per group were selected from all experimental animals including sham operated group, and used for experiments.

The effect on menopausal disorders was evaluated based on 5 pharmacological effects including an estrogen-like effect, an anti-obesity effect, a hyperlipidemia inhibitory effect, a protective effect against fatty liver and an osteoporosis inhibitory effect, and an optimal mixture ratio was determined by comparing to each of red clover extract and pomegranate extract single formula, and using mixed formula showing statistically significant (p<0.01 or p<0.05) increase in efficacy at the same time as red clover:pomegranate extract mixed formula showing a synergistic effect.

Figure 19:
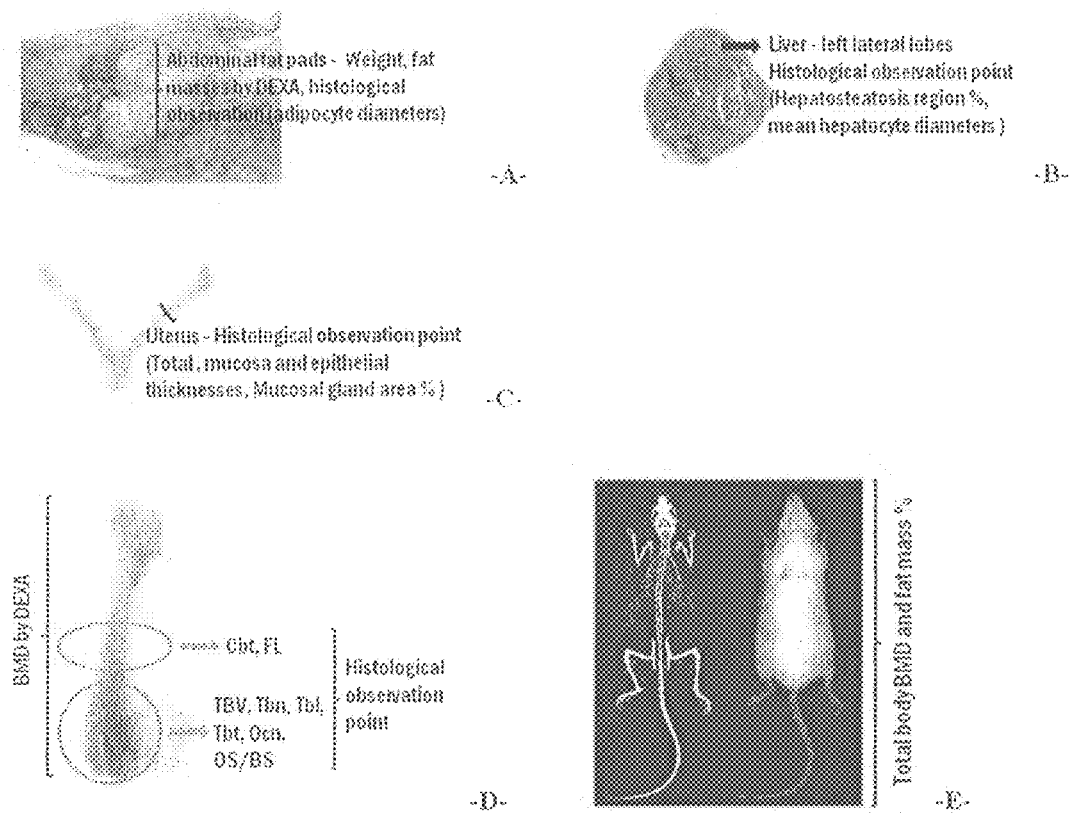
FIG. 19 shows regions of a mouse in which histological changes are observed.

More specifically, the anti-obesity and estrogen-like effects were tested as follows. The body weights on OVX surgery date, 1 day before administration (27 days after OVX), the start date of administration, and from the first day after start of administration up to the time of final sacrifice at least once a week were each recorded, and change amounts of body weights, i.e., body weight gains, for the recovery period after OVX (menopausal disorder induction period) and 12 weeks after start of administration were measured. Food consumption (1, 3, 7, 28, 56 and 83 days after start of administration), serum estradiol levels, amounts of body fat and abdominal fat, weights of abdominal fat pad and uterus, histological changes of uterus and abdominal fat pads (changes in abdominal fat pad thickness and mean adipocyte diameter, thickness of uterus total, epithelium and mucosa, and percentage of uterine glands in the mucosa (FIG. 19) were observed.

Furthermore, to ascertain the protective effect against fatty liver, testing was conducted as follows. Liver weight, serum AST and ALT levels, and histological changes of liver (changes in mean hepatocyte diameter and region with hepatic degeneration showing fatty change) were observed.

The hyperlipidemia inhibitory effect was ascertained through changes in serum TC, LDL, HDL and TG levels.

Figure 20:
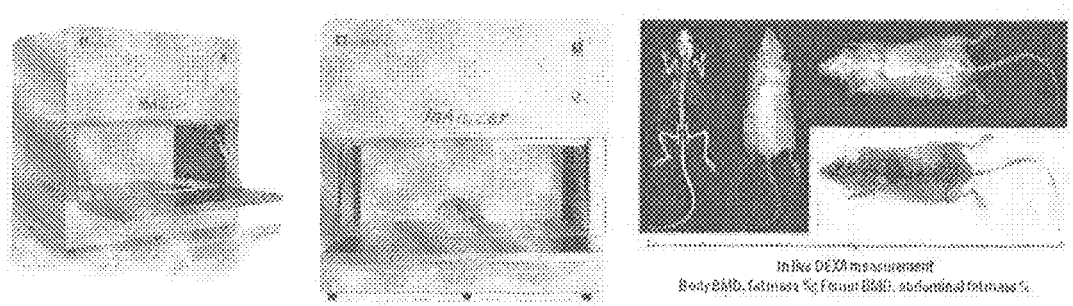
FIG. 20 shows a bone mineral density (BMD) measuring apparatus (left and center, nAlyzer, Medikors, Seungnam, Korea) and a photographic image (right) captured using it.
Figure 21:
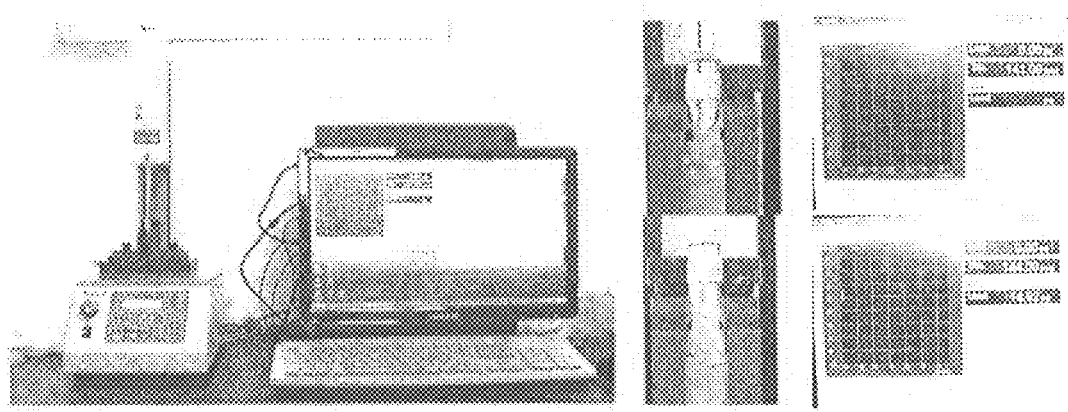
FIG. 21 shows a bone strength measuring apparatus (SV-H1000, Japan Instrumentation System Co., Japan). Bone strength is measured through failure load (FL).

The osteoporosis reduction effect was ascertained through histological changes in wet, dry and ash weights of femurs, BMD (FIG. 20), bone strength (FIG. 21), serum osteocalcin and bALP levels, bone mass and structure (trabecular bone mass, trabecular bone number, thickness and length, and cortical bone thickness), and bone resorption (osteoclast cell number and osteoclast cell surface (OS/BS)).

Example 3-2. Change in Body Weight and Body Weight Gain

Figure 22:
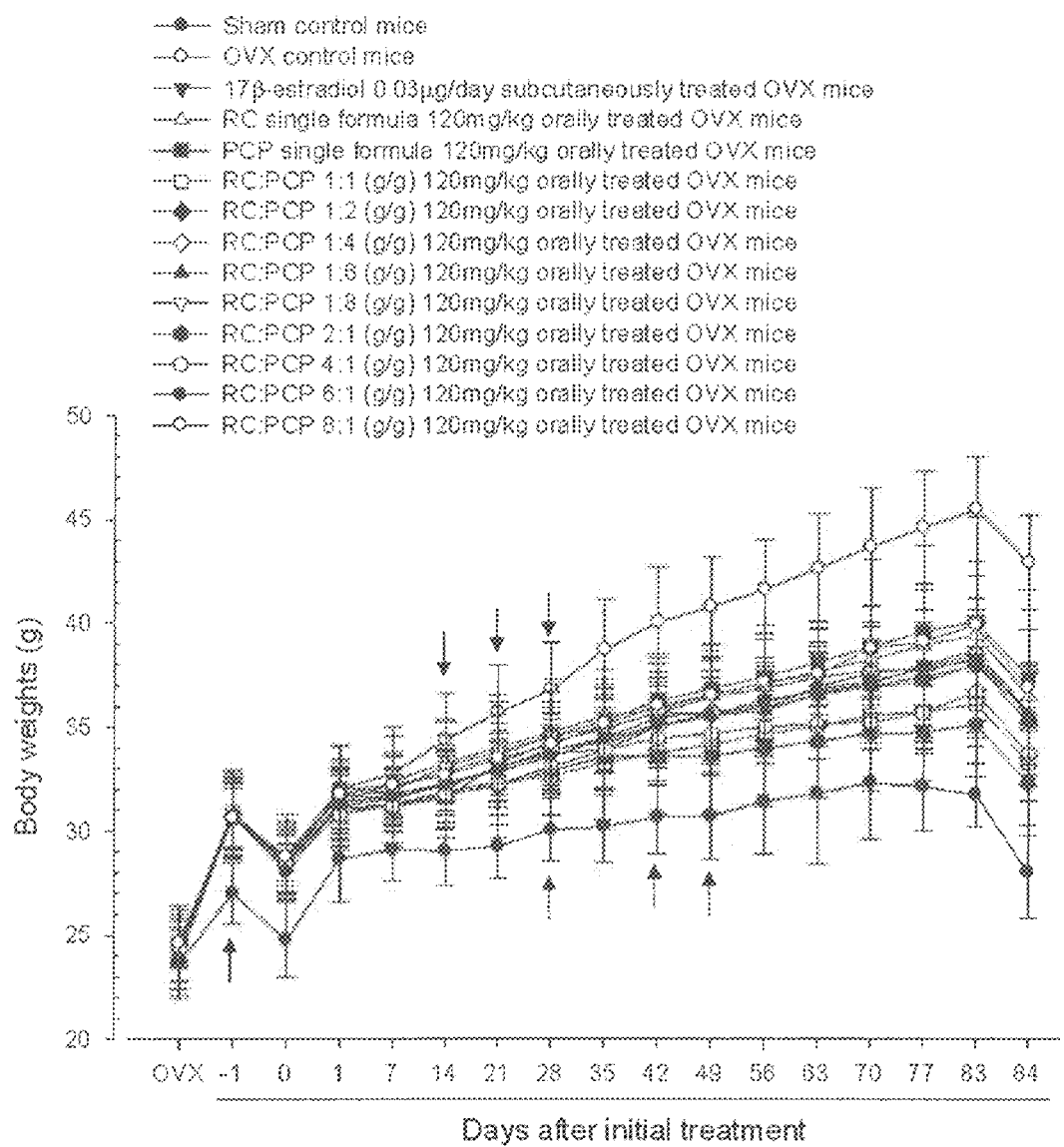
FIG. 22 is a graph showing body weight changes in sham control or OVX ddY mouse model.

At 28 days after OVX surgery, as compared to sham control, only experimental animals showing remarkable increases in body weight were selected and used (OVX mice: 30.71±1.65 g, 28.0-35.1 g; sham operated mice: 26.99±1.46 g, 24.4-28.7 g), so significant (p<0.01) increases in body weight and body weight gain for a 4 week-induction period after OVX were found in all OVX operated groups as compared to sham control, but estradiol, pomegranate extract and red clover extract single formula administered groups started to show significant (p<0.01 or p<0.05) decreases in body weight from 14, 21 and 28 days after start of administration as compared to OVX control, all 9 types of red clover:pomegranate extract mixture administered groups each started to show significant (p<0.01 or p<0.05) decreases in body weight 14, 21 or 28 days after start of administration as compared to OVX control, and all test substance administered groups also showed significant (p<0.01 or p<0.05) decreases in body weight gain for the duration of administration of 84 days as compared to OVX control. Particularly, red clover:pomegranate extract 1:1, 2:1 and 4:1 mixture administered groups started to show significant (p<0.01 or p<0.05) decreases in body weight from 28, 42 and 49 days after start of administration as compared to each of red clover extract and pomegranate extract single formula administered groups, and significant (p<0.01) decreases in body weight gain for the duration of administration were found in the order of red clover:pomegranate extract 2:1, 1:1 and 4:1 as compared to each of red clover extract and pomegranate extract single formula administered groups (Table 16, FIG. 22).

In the case of OVX control, the body weight gain for the duration of administration changed by 351.54% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by −52.56, −44.46, −41.91, −67.72, −54.51, −51.28, −53.33, −52.30, −74.19, −64.40, −48.89 and −44.55% respectively as compared to OVX control.

TABLE 16

| | Periods | | | | |
|---|---|---|---|---|---|
| | Body weights (g) | | | Body weight gains (g) | |
| Groups | At OVX [A]* | At initial treatment [C]* | At sacrifice [D]* | OVX recovery [B-A] | Treatment [D-C] |
| Controls | | | | | |
| Sham | 23.61 ± 1.64 | 24.75 ± 1.81 | 28.00 ± 2.23 | 1.14 ± 1.58 | 3.25 ± 1.92 |
| OVX | 24.21 ± 1.47 | 30.78 ± 2.12$^a$ | 42.90 ± 2.28$^a$ | 4.01 ± 1.23$^a$ | 14.68 ± 2.88$^f$ |
| Estradiol | 24.65 ± 0.99 | 28.71 ± 1.61$^a$ | 35.68 ± 2.19$^{ab}$ | 4.06 ± 1.18$^a$ | 6.96 ± 1.21$^{fg}$ |
| RC | 23.93 ± 1.47 | 28.98 ± 1.73$^a$ | 36.44 ± 1.52$^{ab}$ | 4.36 ± 0.95$^a$ | 8.15 ± 0.95$^{fg}$ |
| PCP | 24.60 ± 1.19 | 28.78 ± 2.02$^a$ | 37.30 ± 2.38$^{ab}$ | 4.18 ± 1.74$^a$ | 8.53 ± 1.31$^{fg}$ |
| RC:PCP | | | | | |
| 1:1 | 24.41 ± 0.97 | 28.53 ± 1.65$^a$ | 33.26 ± 1.85$^{abde}$ | 4.11 ± 1.50$^a$ | 4.74 ± 1.55$^{gij}$ |
| 1:2 | 24.69 ± 1.33 | 28.56 ± 1.78$^a$ | 35.24 ± 2.54$^{ab}$ | 3.88 ± 1.46$^a$ | 6.68 ± 2.55$^{fg}$ |
| 1:4 | 24.40 ± 0.97 | 28.44 ± 1.52$^a$ | 35.59 ± 2.05$^{ab}$ | 4.04 ± 1.72$^a$ | 7.15 ± 1.86$^{fg}$ |
| 1:6 | 24.65 ± 1.02 | 28.75 ± 1.72$^a$ | 35.60 ± 2.47$^{ab}$ | 4.10 ± 1.55$^a$ | 6.85 ± 2.47$^{fg}$ |
| 1:8 | 24.66 ± 1.11 | 28.69 ± 1.31$^a$ | 35.69 ± 1.95$^{ab}$ | 4.03 ± 1.51$^a$ | 7.00 ± 2.58$^{fg}$ |
| 2:1 | 24.58 ± 1.08 | 28.50 ± 1.54$^a$ | 32.29 ± 2.53$^{abce}$ | 3.93 ± 1.31$^a$ | 3.79 ± 2.28$^{gij}$ |
| 4:1 | 24.31 ± 1.86 | 28.41 ± 0.88$^a$ | 33.64 ± 1.45$^{abde}$ | 4.10 ± 1.63$^a$ | 5.23 ± 1.80$^{gij}$ |

TABLE 16-continued

| | Periods | | | | |
|---|---|---|---|---|---|
| | Body weights (g) | | | Body weight gains (g) | |
| Groups | At OVX [A]* | At initial treatment [C]* | At sacrifice [D]* | OVX recovery [B-A] | Treatment [D-C] |
| 6:1 | 23.86 ± 1.77 | 28.03 ± 1.35$^a$ | 35.53 ± 2.02$^{ab}$ | 4.16 ± 1.95$^a$ | 7.50 ± 1.11$^{fg}$ |
| 8:1 | 24.61 ± 1.77 | 28.73 ± 1.12$^a$ | 36.86 ± 4.74$^{ab}$ | 4.11 ± 1.52$^a$ | 8.14 ± 4.99$^h$ |

Values are expressed as mean ± standard deviation of 8 mice.
*All animals were fasted overnight.
$^a$p < 0.01: comparison with sham control according to LSD test
$^b$p < 0.01: comparison with OVX control according to LSD test
$^c$p < 0.01 and
$^d$p < 0.05: comparison with red clover extract administered group according to LSD test
$^e$p < 0.01: comparison with pomegranate extract administered group according to LSD test
$^f$p < 0.01: comparison with sham control according to MW test
$^g$p < 0.01 and
$^h$p < 0.05: comparison with OVX control according to MW test
$^i$p < 0.01: comparison with red clover extract administered group according to MW test
$^j$p < 0.01: comparison with pomegranate extract administered group according to MW test
RC:PCP = a mixture of red clover extract and pomegranate extract (g/g).

Example 3-3. Change in Food Consumption

In OVX control, significant (p<0.01) increases in food consumption were found at all measurement dates from 1 day to 83 days after start of administration as compared to sham control, and when compared to OVX control, only estradiol administered group started to show significant (p<0.01 or p<0.05) decreases in food consumption from 7 days after start of administration, while changes in food consumption were not found in red clover extract and pomegranate extract single formula, and 9 types of red clover:pomegranate extract (g/g) mixed formula administered groups as compared to OVX control, and significant changes in food consumption were not found in the 9 types of red clover:pomegranate extract (g/g) mixed formula administered groups as compared to each of red clover extract and pomegranate extract single formula administered groups (Table 17).

In the case of OVX control, the food consumption changed by 58.37, 75.12, 79.42, 72.71, 75.06 and 95.69% respectively 1, 3, 7, 28, 56 and 83 days after start of administration as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in food consumption by 0.87, −1.21, 4.52, 0.59, −2.78, −1.34, −0.93, 1.96, 2.36, 0.22, 0.70 and −0.46% respectively 1 day after start of administration as compared to OVX control, changes by −5.24, −0.92, 2.22, −1.19, −1.41, 2.02, 1.42, 0.48, 1.23, 1.25, −1.52 and 0.15% respectively 3 days after start of administration, changes by −13.04, −2.04, 2.05, −1.44, 0.37, 2.51, 0.66, 0.70, −2.27, 0.91, −0.22 and 0.68% respectively 7 days after start of administration, changes by −16.34, −2.35, −1.00, −0.79, −1.73, 4.05, 0.25, 0.48, −0.56, −0.34, 2.52 and 0.74% respectively 28 days after start of administration, changes by −20.01, −1.12, −0.59, −2.86, 1.89, −2.76, −1.35, 1.19, −0.75, −0.30, −2.73 and 0.46% respectively 56 days after start of administration, and changes by −27.82, −1.01, −0.57, −1.57, 0.24, −2.64, −4.01, −0.71, −1.08, 0.54, −0.85 and 0.95% respectively 83 days after start of administration.

TABLE 17

| | Points | | | | | |
|---|---|---|---|---|---|---|
| | Food consumption (g/24 hrs/rat): Days after initial treatment | | | | | |
| Groups | 1 | 3 | 7 | 28 | 56 | 83 |
| Controls | | | | | | |
| Sham | 7.20 ± 0.72 | 6.35 ± 0.67 | 6.29 ± 0.72 | 6.59 ± 0.77 | 7.31 ± 0.90 | 7.54 ± 0.78 |
| OVX | 11.40 ± 1.44$^a$ | 11.11 ± 0.98$^a$ | 11.29 ± 1.03$^a$ | 11.38 ± 1.33$^a$ | 12.80 ± 1.41$^a$ | 14.75 ± 1.57$^d$ |
| Estradiol | 11.49 ± 1.41$^a$ | 10.53 ± 0.93$^a$ | 9.82 ± 0.93$^{ac}$ | 9.52 ± 1.01$^{ab}$ | 10.24 ± 0.98$^{ab}$ | 10.65 ± 1.54$^{de}$ |
| RC | 11.26 ± 1.18$^a$ | 11.01 ± 1.53$^a$ | 11.06 ± 1.06$^a$ | 11.11 ± 0.92$^a$ | 12.66 ± 1.62$^a$ | 14.60 ± 1.08$^d$ |
| PCP | 11.91 ± 1.38$^a$ | 11.36 ± 1.67$^a$ | 11.52 ± 1.20$^a$ | 11.26 ± 1.31$^a$ | 12.87 ± 1.55$^a$ | 14.67 ± 1.34$^d$ |
| RC:PCP | | | | | | |
| 1:1 | 11.46 ± 1.12$^a$ | 10.98 ± 1.34$^a$ | 11.13 ± 1.24$^a$ | 11.29 ± 1.31$^a$ | 12.43 ± 1.36$^a$ | 14.52 ± 1.40$^d$ |
| 1:2 | 11.08 ± 1.19$^a$ | 10.96 ± 1.25$^a$ | 11.33 ± 1.25$^a$ | 11.57 ± 1.19$^a$ | 13.04 ± 0.91$^a$ | 14.79 ± 1.35$^d$ |
| 1:4 | 11.24 ± 1.13$^a$ | 11.34 ± 1.11$^a$ | 11.58 ± 1.32$^a$ | 11.84 ± 1.44$^a$ | 12.45 ± 0.84$^a$ | 14.38 ± 1.68$^d$ |
| 1:6 | 11.29 ± 0.94$^a$ | 11.27 ± 1.00$^a$ | 11.37 ± 1.48$^a$ | 11.40 ± 1.62$^a$ | 12.63 ± 1.55$^a$ | 14.16 ± 2.87$^d$ |
| 1:8 | 11.62 ± 1.01$^a$ | 11.17 ± 1.40$^a$ | 11.37 ± 1.55$^a$ | 11.43 ± 1.35$^a$ | 12.95 ± 0.92$^a$ | 14.65 ± 2.04$^d$ |
| 2:1 | 11.66 ± 0.93$^a$ | 11.25 ± 0.95$^a$ | 11.04 ± 1.61$^a$ | 11.31 ± 1.14$^a$ | 12.90 ± 1.33$^a$ | 14.59 ± 1.62$^d$ |
| 4:1 | 11.42 ± 1.46$^a$ | 11.25 ± 0.99$^a$ | 11.40 ± 1.26$^a$ | 11.34 ± 1.26$^a$ | 12.76 ± 1.17$^a$ | 14.83 ± 1.23$^d$ |

TABLE 17-continued

| | Points Food consumption (g/24 hrs/rat): Days after initial treatment | | | | | |
|---|---|---|---|---|---|---|
| Groups | 1 | 3 | 7 | 28 | 56 | 83 |
| 6:1 | 11.48 ± 1.31[a] | 10.94 ± 0.91[a] | 11.27 ± 1.14[a] | 11.66 ± 1.16[a] | 12.45 ± 1.34[a] | 14.63 ± 1.61[d] |
| 8:1 | 11.34 ± 1.99[a] | 11.13 ± 1.13[a] | 11.37 ± 1.58[a] | 11.46 ± 1.25[a] | 12.86 ± 0.72[a] | 14.89 ± 1.17[d] |

Figure 23:
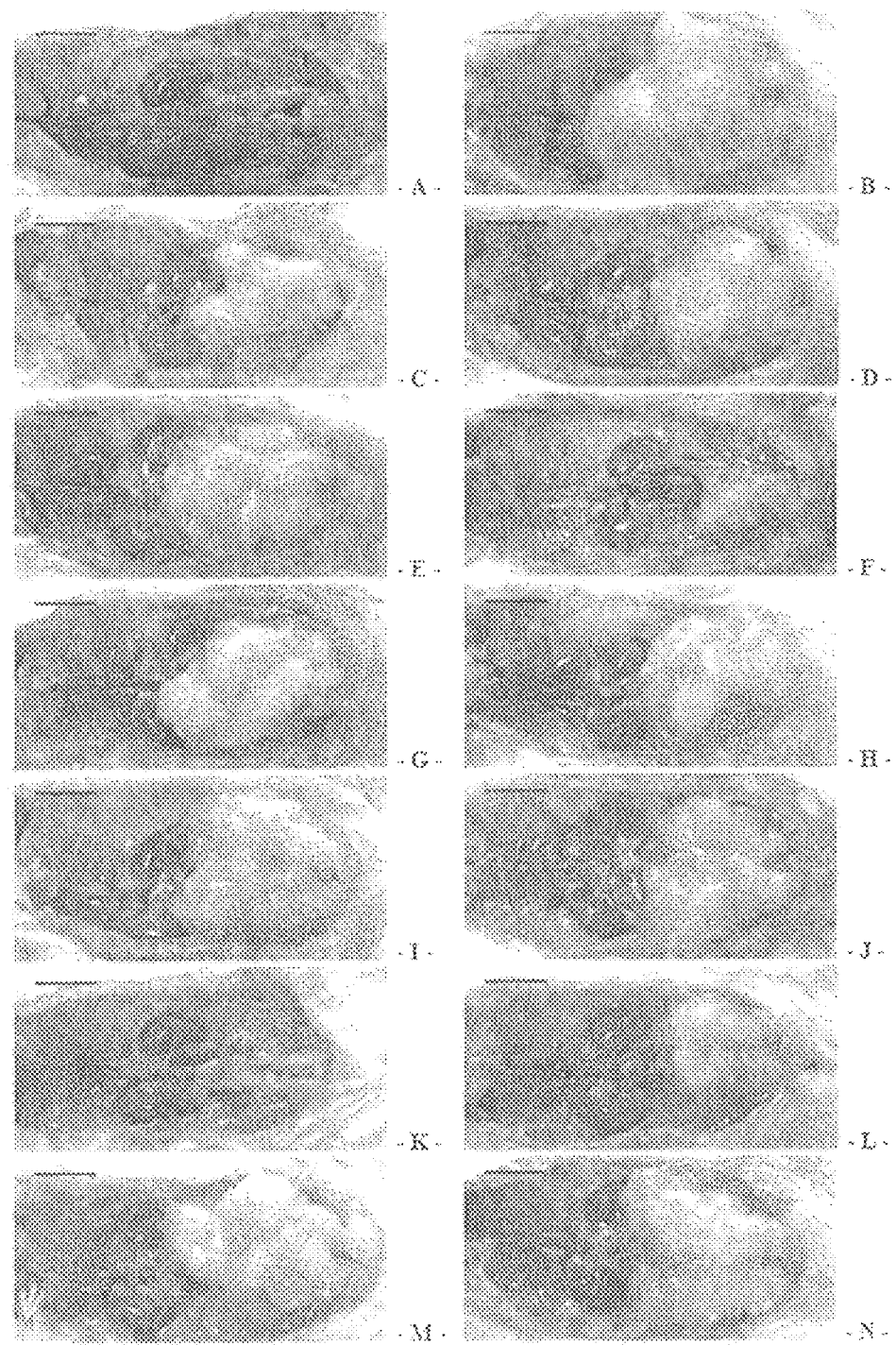
FIG. 23 shows a representative gross photographic image of abdominal fat pads deposited in abdominal cavities of sham control or OVX ddY mouse model. A shows sham control, B shows OVX control, C shows 17β-estradiol 0.03 ug/head treated OVX mice, D shows red clover extract 120 mg/kg administered group, E shows pomegranate extract 120 mg/kg administered group, F shows red clover:pomegranate extract 1:1 mixture (g/g) 120 mg/kg (60:60 mg/kg) administered group, G shows red clover:pomegranate extract 1:2 mixture (g/g) 120 mg/kg (40:80 mg/kg) administered group, H shows red clover:pomegranate extract 1:4 mixture (g/g) 120 mg/kg (24:96 mg/kg) administered group, I shows red clover:pomegranate extract 1:6 mixture (g/g) 120 mg/kg (17:103 mg/kg) administered group, J shows red clover:pomegranate extract 1:8 mixture (g/g) 120 mg/kg (13:107 mg/kg) administered group, K shows red clover:pomegranate extract 2:1 mixture (g/g) 120 mg/kg (80:40 mg/kg) administered group, L shows red clover:pomegranate extract 4:1 mixture (g/g) 120 mg/kg (96:24 mg/kg) administered group, M shows red clover:pomegranate extract 6:1 mixture (g/g) 120 mg/kg (103:17 mg/kg) administered group, N shows red clover:pomegranate extract 8:1 mixture (g/g) 120 mg/kg (107:13 mg/kg) administered group. (Scale bar=11 mm)

Values are expressed as mean ± standard deviation of 8 mice.
[a]$p < 0.01$: comparison with sham control according to LSD test
[b]$p < 0.01$ and [c]$p < 0.05$: comparison with OVX control according to LSD test
[d]$p < 0.01$: comparison with sham control according to MW test
[e]$p < 0.01$: comparison with OVX control according to MW test Example 3-4. Change in Abdominal Fat Pad Weight Significant ($p<0.01$) increases in absolute weight of abdominal fat pad and relative weight to body weight were each found in OVX control as compared to sham control, while significant ($p<0.01$) decreases in abdominal fat pad weight were found in all administered groups including estradiol as compared to OVX control, and particularly, significant ($p<0.01$ or $p<0.05$) decreases in abdominal fat pad weight were found in the order of red clover:pomegranate extract 2:1, 1:1 and 4:1 (g/g) mixture administered groups as compared to each of red clover extract and pomegranate extract single formula administered groups (Table 18, FIG. 23).

In the case of OVX control, the absolute weight of abdominal fat pad changed by 2375.48% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by −82.20, −50.38, −45.23, −73.29, −49.86, −54.48, −45.27, −48.56, −80.93, −70.89, −52.72 and −49.28% respectively as compared to OVX control.

In the case of OVX control, the relative weight of abdominal fat pad to body weight changed by 1491.59% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by −78.86, −41.76, −36.56, −65.51, −39.48, −45.64, −34.56, −38.46, −74.73, −62.83, −42.68 and −38.75% as compared to OVX control.

Example 3-5. Change in Uterus Weight

Figure 24:
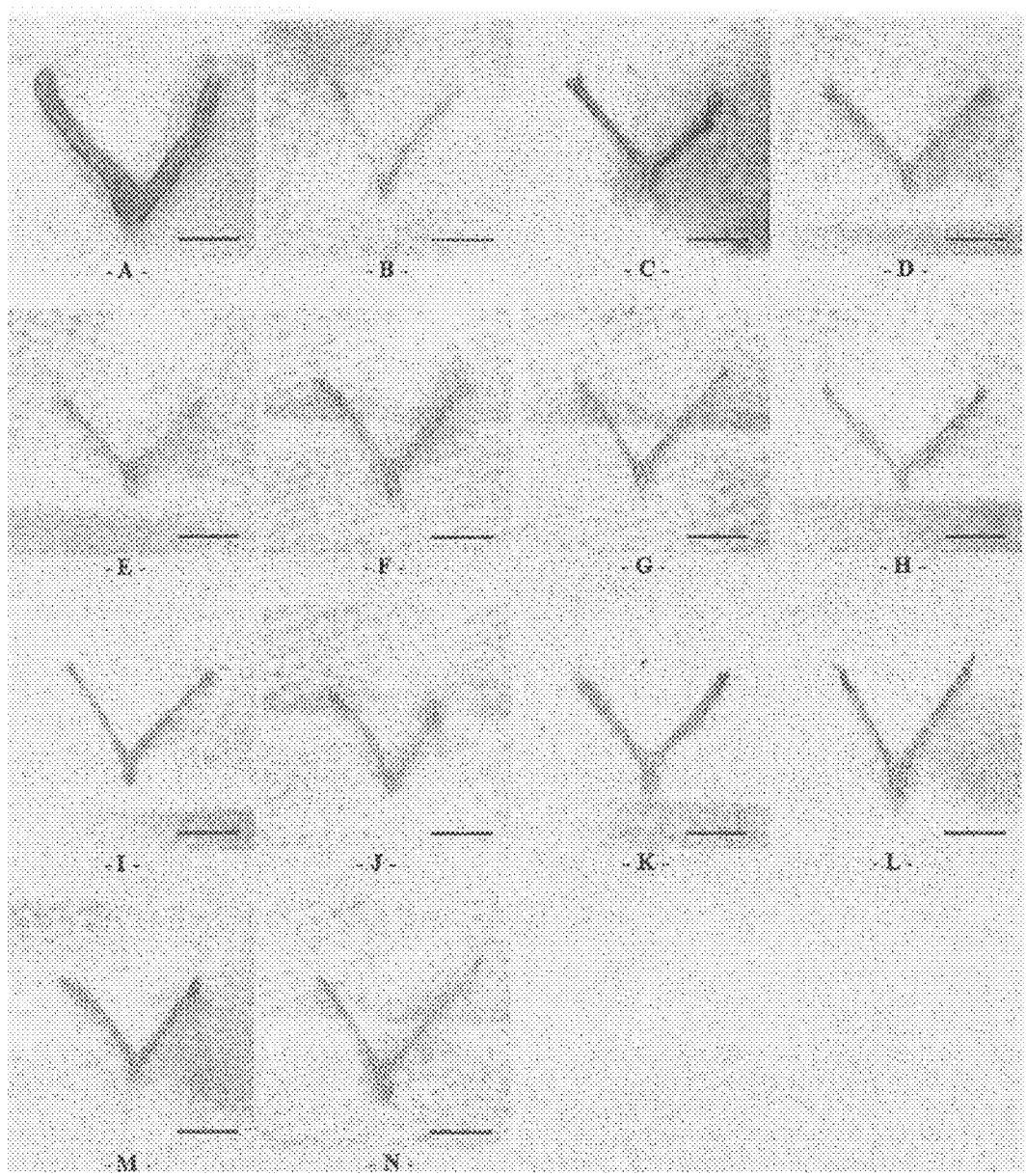
FIG. 24 shows a representative gross photographic image of uteri of sham control or OVX ddY mouse model. A shows sham control, B shows OVX control, C shows 17β-estradiol 0.03 ug/head treated OVX mice, D shows red clover extract 120 mg/kg administered group, E shows pomegranate extract 120 mg/kg administered group, F shows red clover:pomegranate extract 1:1 mixture (g/g) 120 mg/kg (60:60 mg/kg) administered group, G shows red clover:pomegranate extract 1:2 mixture (g/g) 120 mg/kg (40:80 mg/kg) administered group, H shows red clover:pomegranate extract 1:4 mixture (g/g) 120 mg/kg (24:96 mg/kg) administered group, I shows red clover:pomegranate extract 1:6 mixture (g/g) 120 mg/kg (17:103 mg/kg) administered group, J shows red clover:pomegranate extract 1:8 mixture (g/g) 120 mg/kg (13:107 mg/kg) administered group, K shows red clover:pomegranate extract 2:1 mixture (g/g) 120 mg/kg (80:40 mg/kg) administered group, L shows red clover:pomegranate extract 4:1 mixture (g/g) 120 mg/kg (96:24 mg/kg) administered group, M shows red clover:pomegranate extract 6:1 mixture (g/g) 120 mg/kg (103:17 mg/kg) administered group, N shows red clover:pomegranate extract 8:1 mixture (g/g) 120 mg/kg (107:13 mg/kg) administered group. (Scale bar=10 mm)

Significant ($p<0.01$) decreases in absolute weight of uterus and relative weight to body weight were each found in OVX control as compared to sham control, while significant ($p<0.01$) increases in uterus weight were each found in all test substance administered groups including red clover extract and pomegranate extract single formula as compared to OVX control. Particularly, significant ($p<0.01$) increases in uterus weight were found in the order of red clover:pomegranate extract 2:1, 1:1 and 4:1 (g/g) mixture administered groups as compared to each of red clover extract and pomegranate extract single formula administered groups (Table 18, FIG. 24).

In the case of OVX control, the absolute weight of uterus changed by −88.57% as compared to sham control, and estradiol, red clover extract and pomegranate extract single formula, red clover:pomegranate extract 1:1, 1:2, 1:4, 1:6, 1:8, 2:1, 4:1, 6:1 and 8:1 (g/g) mixed formula administered groups had changes by 288.64, 47.73, 45.00, 90.45, 50.00, 42.73, 45.45, 44.55, 125.00, 90.00, 71.82 and 52.73% respectively as compared to OVX control.

In the case of OVX control, the relative weight of uterus to body weight changed by −92.53% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by 372.56, 74.57, 67.51, 145.55, 84.03, 72.76, 76.97, 73.48, 200.64, 142.46, 109.43 and 80.95% respectively as compared to OVX control.

Example 3-6. Change in Liver Weight

Significant ($p<0.01$) decreases in relative weight of liver to body weight were found in OVX control as compared to sham control, while significant ($p<0.01$ or $p<0.05$) increases in relative liver weight were each found in all candidate substance administered groups including all 9 types of red clover:pomegranate extract mixed formula administered groups as compared to OVX control. Particularly, significant ($p<0.01$ or $p<0.05$) increases in relative liver weight were found in the order of red clover:pomegranate extract 2:1, 1:1 and 4:1 (g/g) mixture administered groups as compared to each of red clover extract and pomegranate extract single formula administered groups. On the other hand, when compared to sham control, significant changes in absolute liver weight were not found in all OVX control, and significant changes in absolute liver weight were not found in estradiol, red clover extract and pomegranate extract single formula, and 9 types of red clover:pomegranate extract mixed formula administered groups as compared to OVX control (Table 18).

In the case of OVX control, the absolute liver weight changed by 4.28% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by 5.37, 3.34, 4.95, 10.29, −1.80, −0.24, −1.10, 1.49, 12.28, 11.71, 1.66 and 0.54% respectively as compared to OVX control.

In the case of OVX control, the relative weight of liver to body weight changed by −31.75% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by 27.16, 21.96, 21.28, 42.26, 19.79, 21.18, 19.73, 22.57, 49.99, 42.54, 23.11 and 18.01% respectively as compared to OVX control.

TABLE 18

| Groups | Absolute wet-weight (g) | | | Relative wet-weight (% of body weight) | | |
|---|---|---|---|---|---|---|
| | Abdominal fat pad | Uterus | Liver | Abdominal fat pad | Uterus | Liver |
| Controls | | | | | | |
| Sham | 0.136 ± 0.107 | 0.241 ± 0.082 | 1.205 ± 0.281 | 0.492 ± 0.390 | 0.858 ± 0.286 | 4.291 ± 0.819 |
| OVX | 3.370 ± 0.467$^a$ | 0.028 ± 0.009$^a$ | 1.257 ± 0.174 | 7.835 ± 0.814$^a$ | 0.064 ± 0.022$^a$ | 2.929 ± 0.369$^a$ |
| Estradiol | 0.600 ± 0.536$^{bc}$ | 0.107 ± 0.040$^{ac}$ | 1.324 ± 0.073 | 1.656 ± 1.432$^{bc}$ | 0.303 ± 0.124$^{ac}$ | 3.724 ± 0.307$^c$ |
| RC | 1.672 ± 0.556$^{ac}$ | 0.041 ± 0.006$^{ad}$ | 1.299 ± 0.138 | 4.563 ± 1.417$^{ac}$ | 0.112 ± 0.018$^{ac}$ | 3.571 ± 0.429$^c$ |
| PCP | 1.846 ± 0.415$^{ac}$ | 0.040 ± 0.004$^{ac}$ | 1.319 ± 0.097 | 4.970 ± 1.163$^{ac}$ | 0.107 ± 0.013$^{ac}$ | 3.552 ± 0.388$^c$ |
| RC:PCP | | | | | | |
| 1:1 | 0.900 ± 0.289$^{acfg}$ | 0.052 ± 0.005$^{aceg}$ | 1.386 ± 0.095 | 2.702 ± 0.855$^{acfg}$ | 0.157 ± 0.010$^{aceg}$ | 4.166 ± 0.165$^{ceg}$ |
| 1:2 | 1.690 ± 0.644$^{ac}$ | 0.041 ± 0.007$^{ad}$ | 1.234 ± 0.192 | 4.741 ± 1.527$^{ac}$ | 0.118 ± 0.022$^{ac}$ | 3.508 ± 0.525$^{bd}$ |
| 1:4 | 1.534 ± 0.644$^{ac}$ | 0.039 ± 0.007$^{ad}$ | 1.254 ± 0.140 | 4.259 ± 1.641$^{ac}$ | 0.111 ± 0.020$^{ac}$ | 3.549 ± 0.576$^d$ |
| 1:6 | 1.844 ± 0.561$^{ac}$ | 0.040 ± 0.005$^{ad}$ | 1.234 ± 0.121 | 5.127 ± 1.277$^{ac}$ | 0.113 ± 0.021$^{ac}$ | 3.506 ± 0.420$^{bd}$ |
| 1:8 | 1.734 ± 0.515$^{ac}$ | 0.040 ± 0.006$^{ad}$ | 1.275 ± 0.131 | 4.822 ± 1.219$^{ac}$ | 0.111 ± 0.014$^{ac}$ | 3.590 ± 0.487$^c$ |
| 2:1 | 0.643 ± 0.354$^{aceg}$ | 0.062 ± 0.010$^{aceg}$ | 1.411 ± 0.092$^f$ | 1.980 ± 1.067$^{aceg}$ | 0.193 ± 0.032$^{aceg}$ | 4.392 ± 0.428$^{ceg}$ |
| 4:1 | 0.981 ± 0.310$^{aceg}$ | 0.052 ± 0.010$^{aceg}$ | 1.404 ± 0.107$^f$ | 2.912 ± 0.890$^{aceg}$ | 0.155 ± 0.028$^{aceg}$ | 4.174 ± 0.286$^{ceh}$ |
| 6:1 | 1.593 ± 0.370$^{ac}$ | 0.047 ± 0.016$^{ac}$ | 1.278 ± 0.088 | 4.491 ± 1.034$^{ac}$ | 0.134 ± 0.050$^{ac}$ | 3.605 ± 0.309$^{bc}$ |
| 8:1 | 1.709 ± 0.663$^{ac}$ | 0.042 ± 0.008$^{ac}$ | 1.263 ± 0.103 | 4.799 ± 2.144$^{ac}$ | 0.116 ± 0.029$^{ac}$ | 3.456 ± 0.352$^{bd}$ |

Values are expressed as mean ± standard deviation of 8 mice.
$^a$p < 0.01 and $^b$p < 0.05: comparison with sham control according to MW test
$^c$p < 0.01 and $^d$p < 0.05: comparison with OVX control according to MW test
$^e$p < 0.01 and $^f$p < 0.05: comparison with red clover extract alone administered group according to MW test
$^g$p < 0.01 and $^h$p < 0.05: comparison with pomegranate extract alone administered group according to MW test Example 3-7. Change in Femur Weight Significant (p<0.01) decreases in relative wet weight of femur to body weight as well as decreases in absolute and relative weights of dry and ash bone were found in OVX control as compared to sham control, while remarkable increases in femur weight were each found in all test substance administered groups including estradiol as compared to OVX control. Particularly, significant (p<0.01 or p<0.05) increases in relative wet weight of femur and increases in absolute and relative weights of dry and ash bone were found in the order of red clover:pomegranate extract 2:1, 1:1 and 4:1 (g/g) mixture administered groups as compared to each of red clover extract and pomegranate extract single formula administered groups (Table 19).

In the case of OVX control, the femur absolute wet weight and relative wet weight to body weight changed −4.19 and −37.68% respectively as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in absolute wet weight by 5.79, 1.27, 2.68, 3.67, 0.85, 0.56, 2.82, −0.71, 4.94, 3.39, 0.56 and 0.58% respectively, and changes in relative wet weight by 27.75, 19.30, 18.35, 33.90, 23.11, 21.48, 23.97, 19.47, 39.91, 31.87, 21.50 and 18.54% respectively, as compared to OVX control.

In the case of OVX control, the femur absolute dry weight and relative dry weight to body weight changed by −21.64 and −49.05% respectively as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in absolute dry weight by 14.93, 8.96, 8.46, 17.16, 10.70, 10.45, 12.69, 9.70, 20.65, 16.92, 10.70 and 9.95% respectively, and changes in relative dry weight by 38.22, 28.18, 24.70, 50.75, 35.13, 33.14, 35.43, 31.69, 60.65, 48.83, 33.29 and 29.00% respectively, as compared to OVX control.

In the case of OVX control, the femur absolute ash weight and relative ash weight to body weight changed by −34.74 and −57.77% respectively as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in absolute ash weight by 30.35, 21.39, 19.40, 38.81, 23.88, 25.87, 23.88, 22.39, 51.24, 36.32, 24.38 and 21.39% respectively, and changes in relative ash weight by 57.03, 43.35, 37.53, 79.44, 51.03, 52.74, 49.80, 47.40, 102.33, 74.11, 50.56 and 43.57% respectively, as compared to OVX control.

TABLE 19

| Groups | Absolute weight (g) | | | Relative weight (% of body weight) | | |
|---|---|---|---|---|---|---|
| | Wet | Dry | Ash | Wet | Dry | Ash |
| Controls | | | | | | |
| Sham | 0.092 ± 0.005 | 0.064 ± 0.003 | 0.039 ± 0.003 | 0.331 ± 0.028 | 0.213 ± 0.025 | 0.139 ± 0.019 |
| OVX | 0.089 ± 0.006 | 0.050 ± 0.003$^g$ | 0.025 ± 0.003$^a$ | 0.207 ± 0.013$^a$ | 0.118 ± 0.010$^g$ | 0.059 ± 0.007$^a$ |
| Estradiol | 0.094 ± 0.007 | 0.058 ± 0.004$^{gi}$ | 0.033 ± 0.002$^{ac}$ | 0.264 ± 0.032$^{ac}$ | 0.162 ± 0.016$^{gi}$ | 0.092 ± 0.007$^{ac}$ |
| RC | 0.090 ± 0.004 | 0.055 ± 0.002$^{gi}$ | 0.031 ± 0.003$^{ac}$ | 0.246 ± 0.015$^{ac}$ | 0.151 ± 0.011$^{gi}$ | 0.084 ± 0.010$^{ac}$ |
| PCP | 0.091 ± 0.005 | 0.055 ± 0.002$^{gi}$ | 0.030 ± 0.003$^{ac}$ | 0.244 ± 0.019$^{ac}$ | 0.147 ± 0.010$^{gi}$ | 0.081 ± 0.008$^{ac}$ |

TABLE 19-continued

| | Items | | | | | |
|---|---|---|---|---|---|---|
| | Absolute weight (g) | | | Relative weight (% of body weight) | | |
| Groups | Wet | Dry | Ash | Wet | Dry | Ash |
| RC:PCP | | | | | | |
| 1:1 | 0.092 ± 0.003 | 0.059 ± 0.003$^{gikm}$ | 0.035 ± 0.001$^{bvdf}$ | 0.277 ± 0.017$^{acdf}$ | 0.177 ± 0.006$^{gikm}$ | 0.105 ± 0.006$^{acdf}$ |
| 1:2 | 0.089 ± 0.005 | 0.056 ± 0.004$^{gi}$ | 0.031 ± 0.004$^{ac}$ | 0.254 ± 0.021$^{ac}$ | 0.159 ± 0.018$^{gi}$ | 0.088 ± 0.009$^{ac}$ |
| 1:4 | 0.089 ± 0.005 | 0.056 ± 0.003$^{gi}$ | 0.032 ± 0.004$^{ac}$ | 0.251 ± 0.022$^{ac}$ | 0.156 ± 0.014$^{gi}$ | 0.089 ± 0.016$^{ac}$ |
| 1:6 | 0.091 ± 0.006 | 0.057 ± 0.004$^{gi}$ | 0.031 ± 0.004$^{ac}$ | 0.256 ± 0.015$^{ac}$ | 0.159 ± 0.008$^{gin}$ | 0.088 ± 0.012$^{ac}$ |
| 1:8 | 0.088 ± 0.007 | 0.055 ± 0.005$^{g}$ | 0.031 ± 0.004$^{ac}$ | 0.247 ± 0.021$^{ac}$ | 0.155 ± 0.015$^{gi}$ | 0.086 ± 0.011$^{ac}$ |
| 2:1 | 0.093 ± 0.003 | 0.061 ± 0.002$^{hikm}$ | 0.038 ± 0.002$^{cdf}$ | 0.289 ± 0.021$^{acdf}$ | 0.189 ± 0.016$^{gikm}$ | 0.118 ± 0.012$^{acdf}$ |
| 4:1 | 0.092 ± 0.005 | 0.059 ± 0.003$^{giln}$ | 0.034 ± 0.003$^{acef}$ | 0.272 ± 0.016$^{acef}$ | 0.175 ± 0.012$^{gikn}$ | 0.102 ± 0.010$^{acdf}$ |
| 6:1 | 0.089 ± 0.004 | 0.056 ± 0.005$^{gi}$ | 0.031 ± 0.003$^{ac}$ | 0.251 ± 0.012$^{ac}$ | 0.157 ± 0.011$^{gi}$ | 0.088 ± 0.009$^{ac}$ |
| 8:1 | 0.089 ± 0.007 | 0.055 ± 0.005$^{g}$ | 0.031 ± 0.003$^{ac}$ | 0.245 ± 0.029$^{ac}$ | 0.152 ± 0.021$^{gi}$ | 0.084 ± 0.014$^{ac}$ |

Values are expressed as mean ± standard deviation of 8 mice.
$^a$p < 0.01 and $^b$p < 0.05: comparison with sham control according to LSD test
$^c$p < 0.01: comparison with OVX control according to LSD test
$^d$p < 0.01 and $^e$p < 0.05: comparison with red clover extract alone administered group according to LSD test
$^f$p < 0.01: comparison with pomegranate extract alone administered group according to LSD test
$^g$p < 0.01 and $^h$p < 0.05: comparison with sham control according to MW test
$^i$p < 0.01 and $^j$p < 0.05: comparison with OVX control according to MW test
$^k$p < 0.01 and $^l$p < 0.05: comparison with red clover extract alone administered group according to MW test
$^m$p < 0.01 and $^n$p < 0.05: comparison with pomegranate extract alone administered group according to MW test Example 3-8. Serum Biochemical Change (1): AST, ALT, TC, LDL, HDL and TG Significant (p<0.01) increases in serum Aspartate aminotransferase (AST), Alanine aminotransferase (ALT), Total cholesterol (TC), Low density lipoprotein (LDL) and Triglyceride (TG) levels as well as significant (p<0.01) decreases in High density lipoprotein (HDL) level were found in OVX control as compared to sham control, while significant (p<0.01) decreases in serum AST, ALT, TC, LDL and TG levels and significant (p<0.01) increases in serum HDL level were each found in all test substance administered groups including red clover extract single formula as compared to OVX control. Particularly, significant (p<0.01 or p<0.05) decreases in serum AST, ALT, TC, LDL and TG levels and increases in serum HDL level were found in the order of red clover:pomegranate extract 2:1, 1:1 and 4:1 (g/g) mixture administered groups as compared to each of red clover extract and pomegranate extract single formula administered groups (Table 20).

In the case of OVX control, the serum AST and ALT levels changed by 92.30 and 100.66% respectively as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in serum AST level by −33.98, −13.94, −12.56, −26.73, −14.10, −13.71, −12.25, −12.17, −32.67, −25.96, −16.26 and −13.10% respectively, and changes in serum AST level by −31.58, −17.11, −16.28, −31.74, −16.78, −19.08, −18.82, −17.60, −37.17, −30.43, −19.74 and −18.26% respectively, as compared to OVX control.

In the case of OVX control, the serum TC and LDL levels changed by 100.00 and 189.26% respectively as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in serum TC level by −25.94, −20.01, −17.85, −28.87, −20.64, −19.94, −18.27, −17.50, −36.33, −26.85, −21.27 and −19.46% respectively, and changes in serum LDL level by −26.87, −14.98, −11.96, −26.87, −14.57, −13.40, −12.92, −12.03, −36.49, −23.71, −15.40 and −15.05% respectively, as compared to OVX control.

In the case of OVX control, the serum HDL and TG levels changed by −50.45 and 305.74% respectively as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in serum HDL level by 52.09, 37.17, 33.25, 60.99, 36.91, 32.98, 34.55, 34.03, 87.70, 59.42, 39.27 and 34.29% respectively, and changes in serum TG level by −34.80, −17.99, −17.07, −31.56, −19.48, −18.98, −18.48, −17.74, −43.55, −28.56, −18.65 and −18.23% respectively, as compared to OVX control.

TABLE 20

| | Items | | | | | |
|---|---|---|---|---|---|---|
| | Serum biochemistrical values | | | | | |
| Groups | AST (U/L) | ALT (U/L) | TC (mg/dl) | LDL (mg/dl) | HDL (mg/dl) | TG (mg/dl) |
| Controls | | | | | | |
| Sham | 84.38 ± 13.95 | 37.88 ± 11.98 | 89.63 ± 16.87 | 62.88 ± 10.11 | 96.38 ± 11.78 | 37.00 ± 10.39 |
| OVX | 162.35 ± 15.84$^a$ | 76.00 ± 10.54$^a$ | 179.25 ± 21.41$^a$ | 181.88 ± 17.94$^a$ | 47.75 ± 11.20$^a$ | 150.13 ± 20.90$^a$ |
| Estradiol | 107.13 ± 12.43$^{ac}$ | 52.00 ± 10.03$^{ac}$ | 132.75 ± 21.06$^{ac}$ | 133.00 ± 10.54$^{ac}$ | 72.63 ± 11.04$^{ac}$ | 97.88 ± 18.16$^{ac}$ |
| RC | 139.63 ± 8.86$^{ac}$ | 63.00 ± 5.66$^{ac}$ | 143.38 ± 10.80$^{ac}$ | 154.63 ± 13.05$^{ac}$ | 65.50 ± 5.10$^{ac}$ | 123.13 ± 9.11$^{ac}$ |
| PCP | 141.88 ± 7.64$^{ac}$ | 63.63 ± 4.84$^{ac}$ | 147.25 ± 12.28$^{ac}$ | 160.13 ± 7.41$^{ac}$ | 63.63 ± 6.05$^{ac}$ | 124.50 ± 9.38$^{ac}$ |

TABLE 20-continued

| | | | Items Serum biochemistrical values | | | |
|---|---|---|---|---|---|---|
| Groups | AST (U/L) | ALT (U/L) | TC (mg/dl) | LDL (mg/dl) | HDL (mg/dl) | TG (mg/dl) |
| | | | RC:PCP | | | |
| 1:1 | 118.88 ± 13.26$^{acdf}$ | 51.88 ± 7.26$^{acef}$ | 127.50 ± 10.85$^{acef}$ | 133.00 ± 13.60$^{acdf}$ | 76.88 ± 8.25$^{acef}$ | 102.75 ± 12.96$^{acdf}$ |
| 1:2 | 139.38 ± 10.72$^{ac}$ | 63.25 ± 7.46$^{ac}$ | 142.25 ± 10.35$^{ac}$ | 155.38 ± 16.23$^{ac}$ | 65.38 ± 9.55$^{ac}$ | 120.88 ± 14.80$^{ac}$ |
| 1:4 | 140.00 ± 10.00$^{ac}$ | 61.50 ± 11.33$^{ac}$ | 143.50 ± 12.36$^{ac}$ | 157.50 ± 11.63$^{ac}$ | 63.50 ± 6.59$^{ac}$ | 121.63 ± 11.59$^{ac}$ |
| 1:6 | 142.38 ± 10.49$^{ac}$ | 62.00 ± 6.39$^{ac}$ | 146.50 ± 8.25$^{ac}$ | 158.38 ± 12.44$^{ac}$ | 64.25 ± 10.58$^{ac}$ | 122.38 ± 14.04$^{ac}$ |
| 1:8 | 142.50 ± 9.44$^{ac}$ | 62.63 ± 6.72$^{ac}$ | 147.88 ± 13.88$^{ac}$ | 160.00 ± 9.96$^{ac}$ | 64.00 ± 9.70$^{a}$ | 123.50 ± 12.14$^{ac}$ |
| 2:1 | 109.25 ± 7.74$^{acdf}$ | 47.75 ± 11.31$^{bcdf}$ | 114.13 ± 12.93$^{bcdf}$ | 115.50 ± 11.15$^{bcdf}$ | 89.63 ± 7.13$^{cdf}$ | 84.75 ± 13.64$^{cdf}$ |
| 4:1 | 120.13 ± 15.07$^{acdf}$ | 52.88 ± 6.10$^{aceg}$ | 131.13 ± 8.24$^{aceg}$ | 138.75 ± 8.81$^{acef}$ | 76.13 ± 9.75$^{acef}$ | 107.25 ± 9.85$^{acef}$ |
| 6:1 | 135.88 ± 10.01$^{ac}$ | 61.00 ± 8.09$^{ac}$ | 141.13 ± 9.63$^{ac}$ | 153.88 ± 13.92$^{ac}$ | 66.50 ± 13.64$^{ac}$ | 122.13 ± 9.25$^{ac}$ |
| 8:1 | 141.00 ± 8.35$^{ac}$ | 62.13 ± 11.01$^{ac}$ | 144.38 ± 14.81$^{ac}$ | 144.50 ± 12.24$^{ac}$ | 64.13 ± 10.43$^{ac}$ | 122.75 ± 9.68$^{ac}$ |

Figure 25:
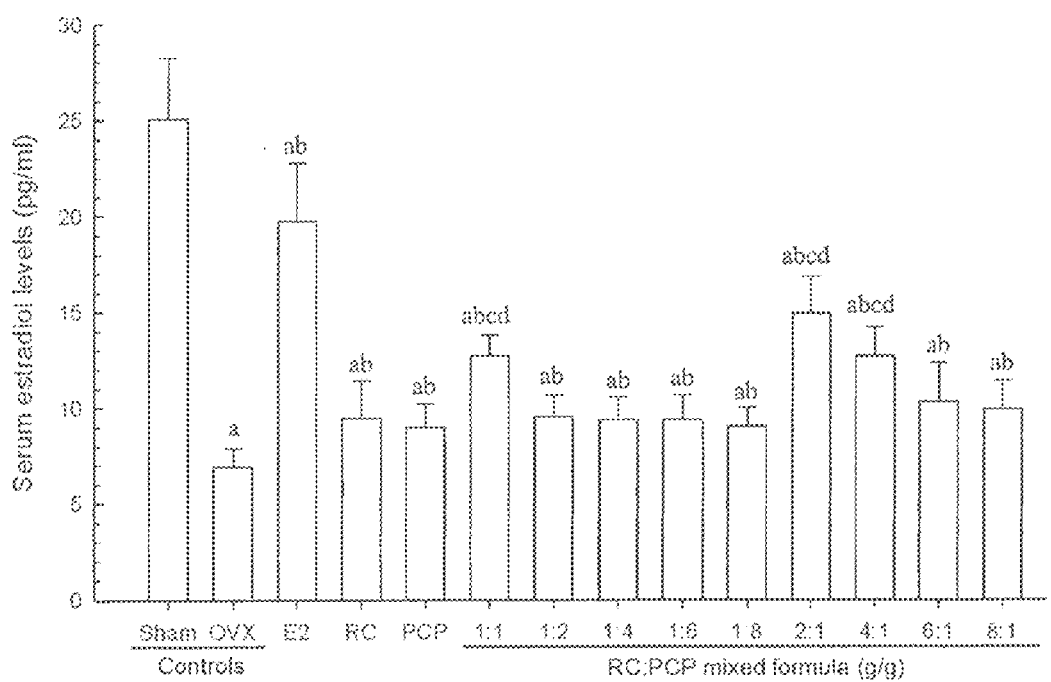
FIG. 25 shows serum estradiol levels of sham control or OVX ddY mice. a $p<0.01$: comparison with sham control according to MW test, b $p<0.01$: comparison with OVX control according to MW test, c $p<0.01$: comparison with red clover extract single formula treated group according to MW test, and d $p<0.01$: comparison with pomegranate extract single formula treated group according to MW test. (E2 represents 17β-estradiol)

Values are expressed as mean ± standard deviation of 8 mice.
$^{a}$p < 0.01 and $^{b}$p < 0.05: comparison with sham control according to LSD test
$^{c}$p < 0.01: comparison with OVX control according to LSD test
$^{d}$p < 0.01 and $^{e}$p < 0.05: comparison with red clover extract alone administered group according to LSD test
fp < 0.01 and $^{g}$p < 0.05: comparison with pomegranate extract alone administered group according to LSD test Example 3-9. Serum Biochemical Change (2): Estradiol Significant (p<0.01) decreases in serum estradiol level were found in OVX control as compared to sham control, while significant (p<0.01) increases in serum estradiol level were each found in all test substance administered groups including pomegranate extract single formula as compared to OVX control. Particularly, significant (p<0.01) increases in serum estradiol level were found in the order of red clover:pomegranate extract 2:1, 1:1 and 4:1 (g/g) mixture administered groups as compared to each of red clover extract and pomegranate extract single formula administered groups (FIG. 25).

In the case of OVX control, the serum estradiol level changed by −72.46% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by 185.69, 37.14, 30.62, 84.78, 37.86, 36.23, 35.87, 31.34, 116.30, 83.70, 49.64 and 44.02% respectively as compared to OVX control.

Example 3-10. Serum Biochemical Change (3): Osteocalcin and bALP

Figure 26:
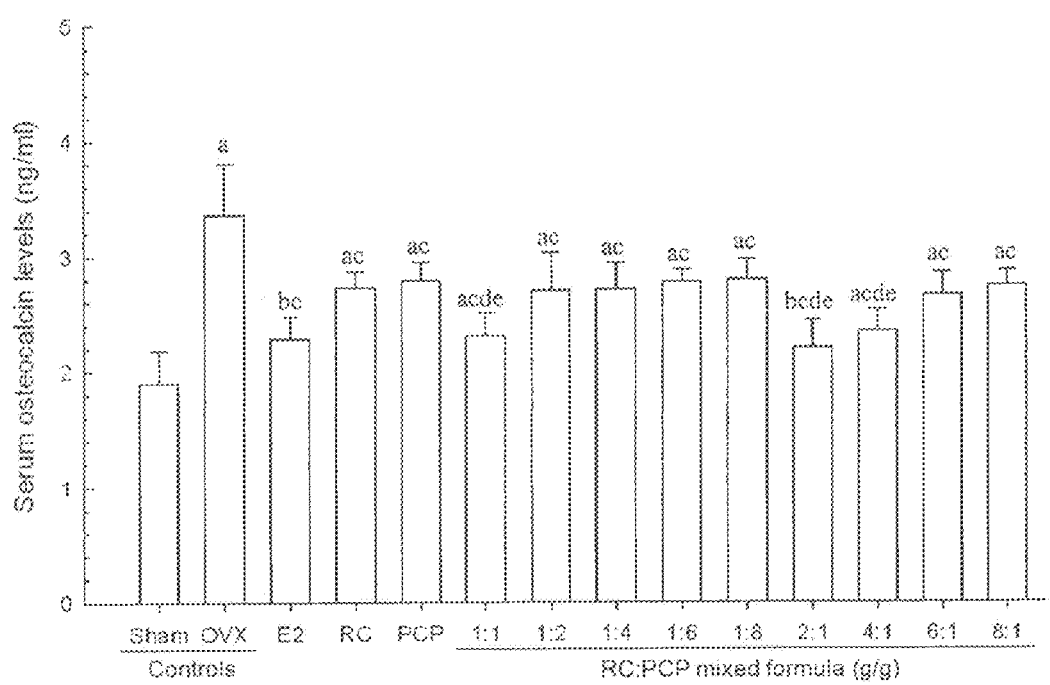
FIG. 26 shows serum osteocalcin levels of sham control or OVX ddY mice. a $p<0.01$ and b $p<0.05$: comparison with sham control according to MW test, c $p<0.01$: comparison with OVX control according to MW test, d $p<0.01$: comparison with red clover extract single formula treated group according to MW test, e $p<0.01$: comparison between pomegranate extract single formula treated group and comparison group according to MW test.
Figure 27:
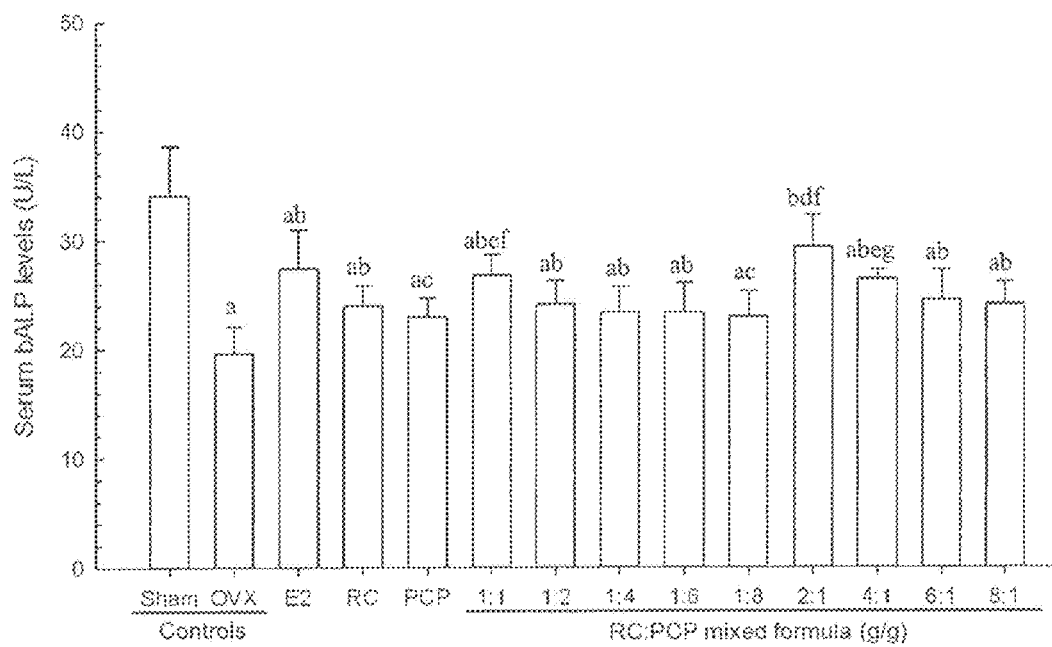
FIG. 27 shows serum bALP levels of sham control or OVX ddY mice. a $p<0.01$: comparison with sham control according to LSD test, b $p<0.01$ and c $p<0.05$: comparison with OVX control according to LSD test, d $p<0.01$ and e $p<0.05$: comparison with red clover extract 40 mg/kg administered group according to LSD test, f $p<0.01$ and g $p<0.05$: comparison with pomegranate extract 20 mg/kg administered group according to LSD test.

Significant (p<0.01) increases in serum osteocalcin level as well as significant (p<0.01) decreases in bALP level were found in OVX control as compared to sham control, while significant (p<0.01 or p<0.05) decreases in serum osteocalcin level and increases in serum bALP level were each found in all candidate substance administered groups including red clover extract and pomegranate extract single formula as compared to OVX control. Particularly, significant (p<0.01) decreases in serum osteocalcin level and increases in serum bALP level were found in the order of red clover:pomegranate extract 2:1, 1:1 and 4:1 (g/g) mixture administered groups as compared to each of red clover extract and pomegranate extract single formula administered groups (FIGS. 26 and 27).

In the case of OVX control, the serum osteocalcin and bALP levels changed by 77.11 and −42.35% respectively as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in serum osteocalcin level by −31.95, −18.80, −17.20, −31.43, −19.54, −19.35, −17.27, −16.83, −34.29, −30.05, −20.62 and −18.39% respectively, and change in serum bALP level by 39.72, 22.04, 17.04, 36.32, 22.87, 19.17, 18.92, 17.31, 49.67, 34.38, 24.84 and 22.84% respectively, as compared to OVX control.

Example 3-11. Chaste in Bone Mineral Density

Figure 28:
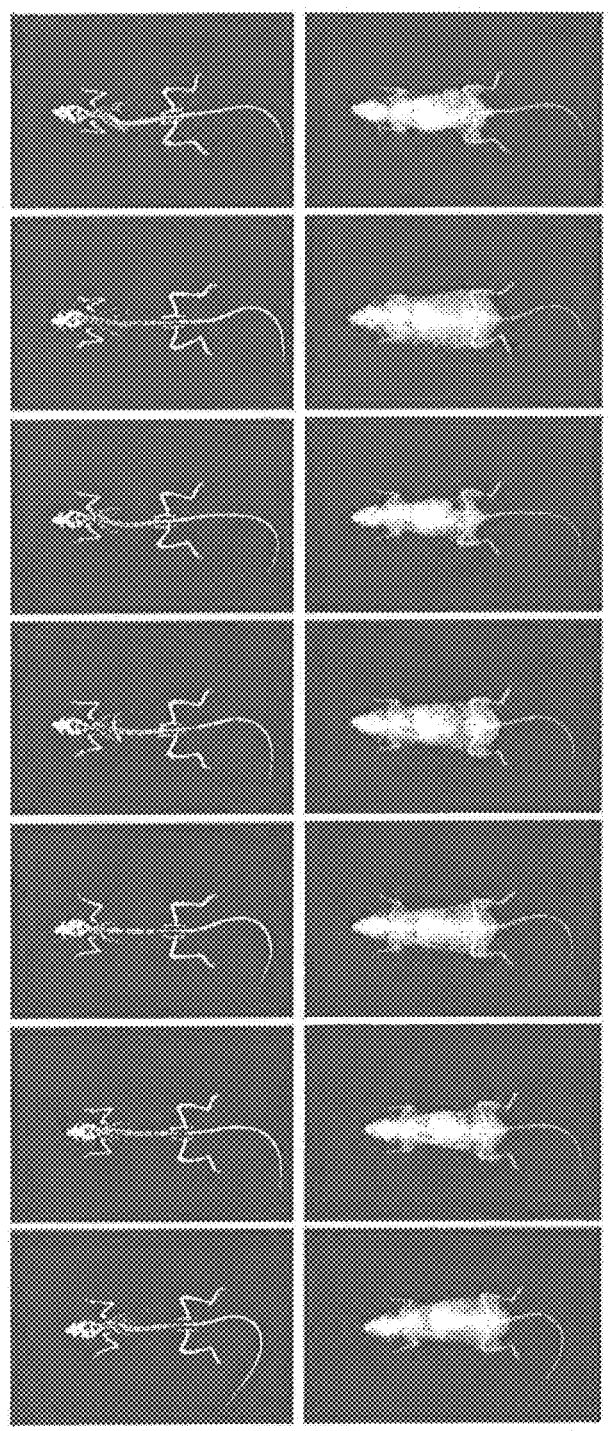
FIGS. 28 and 29 show Dual-energy x-ray absorptiometry (DEXA) images of sham control or OVX ddY mice. They show representative gross photographic images of abdominal fat pads deposited in abdominal cavities of models. A shows sham control, B shows OVX control, C shows 17β-estradiol 0.03 ug/head treated OVX mice, D shows red clover extract 120 mg/kg administered group, E shows pomegranate extract 120 mg/kg administered group, F shows red clover:pomegranate extract 1:1 mixture (g/g) 120 mg/kg (60:60 mg/kg) administered group, G shows red clover:pomegranate extract 1:2 mixture (g/g) 120 mg/kg (40:80 mg/kg) administered group, H shows red clover:pomegranate extract 1:4 mixture (g/g) 120 mg/kg (24:96 mg/kg) administered group, I shows red clover:pomegranate extract 1:6 mixture (g/g) 120 mg/kg (17:103 mg/kg) administered group, J shows red clover:pomegranate extract 1:8 mixture (g/g) 120 mg/kg (13:107 mg/kg) administered group, K shows red clover:pomegranate extract 2:1 mixture (g/g) 120 mg/kg (80:40 mg/kg) administered group, L shows red clover:pomegranate extract 4:1 mixture (g/g) 120 mg/kg (96:24 mg/kg) administered group, M shows red clover:pomegranate extract 6:1 mixture (g/g) 120 mg/kg (103:17 mg/kg) administered group, N shows red clover:pomegranate extract 8:1 mixture (g/g) 120 mg/kg (107:13 mg/kg) administered group.
Figure 28:
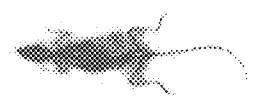
Figure 28:
Figure 28:
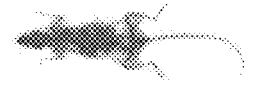
Figure 28:
Figure 28:
Figure 28:
Figure 28:
Figure 29:
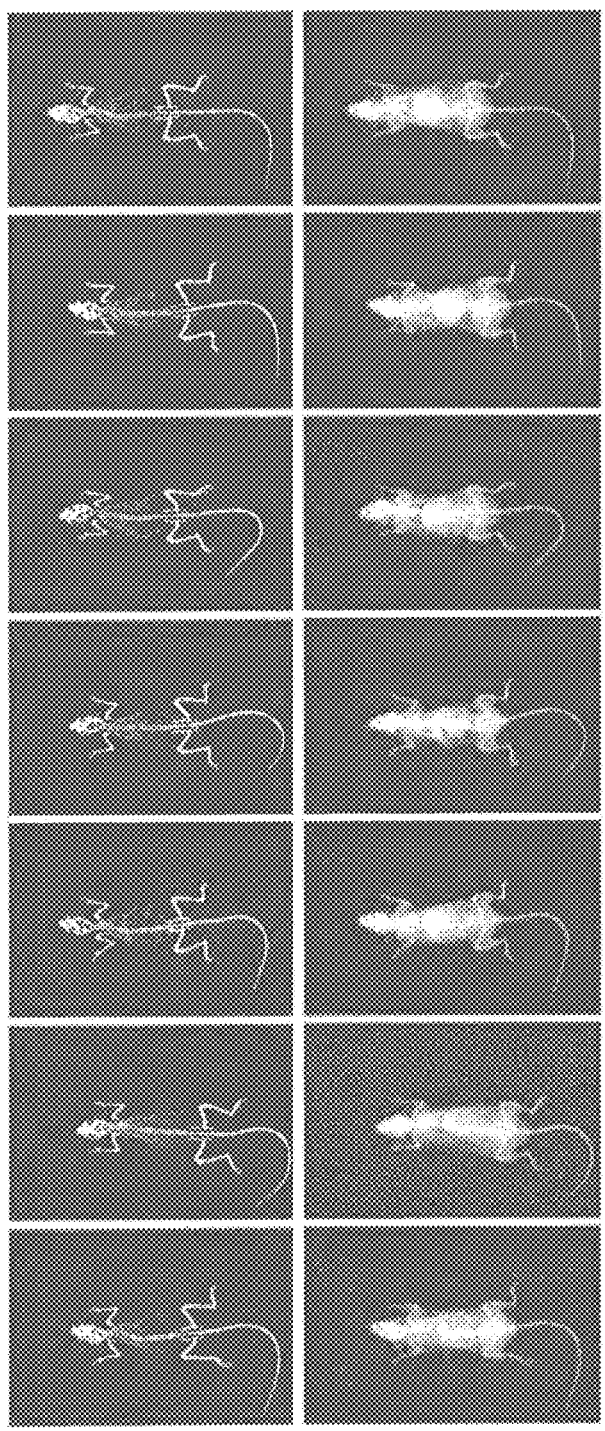
Figure 29:
Figure 29:
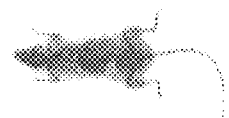
Figure 29:
Figure 29:
Figure 29:
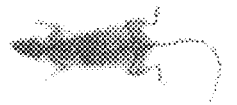
Figure 29:
Figure 29:

OVX control significantly (p<0.01) decreased in each of the mean total body bone mineral density and femur total bone mineral density as compared to sham control, while significant (p<0.01) increases in total body bone mineral density and total femur bone mineral density were found in all test substance administered groups including all 9 types of red clover:pomegranate extract mixed formulas as compared to OVX control. Particularly, significant (p<0.01) increases in mean total body bone mineral density and total femur bone mineral density were found in the order of red clover:pomegranate extract 2:1, 1:1 and 4:1 (g/g) mixture administered groups as compared to each of red clover extract and pomegranate extract single formula administered groups (Table 21, FIGS. 28 and 29).

In the case of OVX control, the mean total body bone mineral density changed by −12.75% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by 9.86, 4.41, 3.48, 8.00, 5.10, 4.29, 4.00, 3.77, 10.84, 7.42, 5.57 and 5.16% respectively as compared to OVX control.

In the case of OVX control, the total femur bone mineral density changed by −12.56% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by 10.78, 5.23, 5.18, 9.20, 6.73, 5.93, 5.61, 5.39, 11.53, 8.97, 7.42 and 5.02% respectively as compared to OVX control.

Example 3-12. Change in Amounts of Body Fat and Abdominal Fat

Significant (p<0.01) increases in amounts of body fat and abdominal fat were found in OVX control as compared to sham control, while significant (p<0.01) decreases in amounts of body fat and abdominal fat were each found in all test substance administered groups including estradiol as compared to OVX control. Particularly, significant ($p<0.01$ or $p<0.05$) decreases in amounts of body fat and abdominal fat were found in the order of red clover:pomegranate extract 2:1, 1:1 and 4:1 (g/g) mixture administered groups as compared to each of red clover extract and pomegranate extract single formula administered groups (Table 21).

In the case of OVX control, the amount of body fat changed by 213.34% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by −33.02, −15.21, −13.20, −31.06, −20.16, −15.67, −14.24, −13.90, −46.56, −27.58, −18.22 and −15.32% respectively as compared to OVX control.

Figure 30:
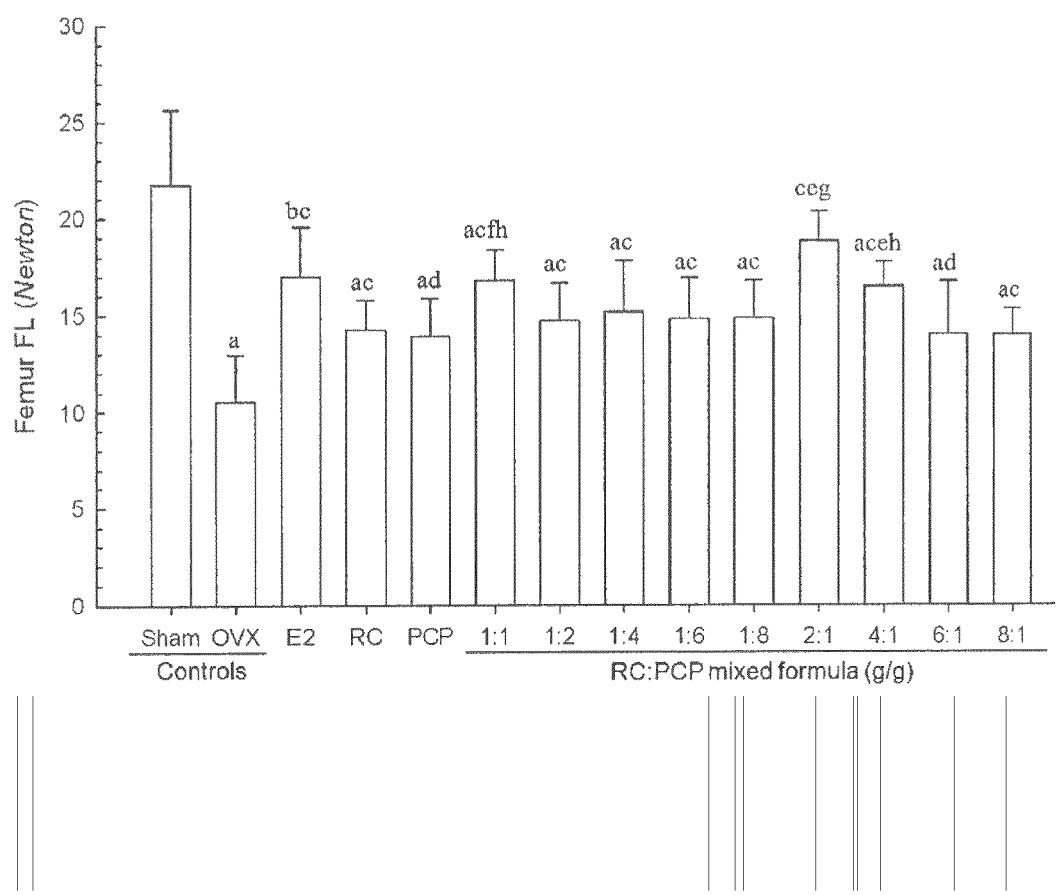
FIG. 30 shows femur failure load or bone strength of sham control or OVX ddY mice. a $p<0.01$ and b $p<0.05$: comparison with sham control according to MW test, c $p<0.01$ and d $p<0.05$: comparison with OVX control according to MW test, e $p<0.01$ and f $p<0.05$: comparison with red clover extract 40 mg/kg administered group according to MW test, g $p<0.01$ and h $p<0.05$: comparison with pomegranate extract 20 mg/kg administered group according to MW test.

In the case of OVX control, the amount of abdominal fat changed by 279.17% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by −35.00, −17.21, −15.43, −35.30, −18.61, −17.54, −16.07, −15.42, −43.69, −32.08, −19.54 and −17.66% respectively as compared to OVX control.

each of red clover extract and pomegranate extract single formula administered groups (FIG. 30).

In the case of OVX control, the bone strength of femur mid-shaft region changed by −51.62% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by 61.41, 35.17, 32.31, 59.11, 39.58, 44.06, 40.40, 40.85, 78.65, 56.44, 33.33 and 32.61% respectively as compared to OVX control.

Example 3-14. Histological Change (1): Abdominal Fat Pad, Uterus and Liver (1) Abdominal Fat Pad Due to remarkable abdominal fat deposition, significant ($p<0.01$) increases in abdominal fat pad thickness and mean adipocyte diameter were each found in OVX control as compared to sham control, while significant ($p<0.01$) decreases in abdominal fat pad thickness and mean adipocyte diameter were each found in all test substance administered groups including pomegranate extract single formula as compared to OVX control. Particularly, significant ($p<0.01$ or $p<0.05$) decreases in abdominal fat pad thickness and mean adipocyte diameter were each found in the order

TABLE 21

| | Items | | | |
|---|---|---|---|---|
| | Bone mineral density (g/cm$^2$) | | Fat density (% of body mass) | |
| Groups | Total body | Right femur | Total body | Abdominal cavity |
| Controls | | | | |
| Sham | 0.0247 ± 0.0006 | 0.0268 ± 0.0006 | 11.16 ± 2.15 | 10.85 ± 1.50 |
| OVX | 0.0216 ± 0.0003$^a$ | 0.0234 ± 0.0004$^a$ | 34.97 ± 3.52$^a$ | 41.15 ± 4.55$^a$ |
| Estradiol | 0.0237 ± 0.0004$^{ac}$ | 0.0259 ± 0.0008$^{bc}$ | 23.42 ± 4.24$^{ac}$ | 26.75 ± 4.22$^{ac}$ |
| RC | 0.0225 ± 0.0005$^{ac}$ | 0.0246 ± 0.0004$^{ac}$ | 29.65 ± 1.99$^{ac}$ | 34.06 ± 4.04$^{ac}$ |
| PCP | 0.0223 ± 0.0004$^{ac}$ | 0.0246 ± 0.0003$^{ac}$ | 30.35 ± 2.21$^{ac}$ | 34.80 ± 2.81$^{ac}$ |
| RC:PCP | | | | |
| 1:1 | 0.0233 ± 0.0005$^{acdf}$ | 0.0256 ± 0.0007$^{aceg}$ | 24.11 ± 4.25$^{acdf}$ | 26.62 ± 4.66$^{acdf}$ |
| 1:2 | 0.0227 ± 0.0005$^{ac}$ | 0.0250 ± 0.0011$^{ac}$ | 27.92 ± 5.30$^{ac}$ | 33.49 ± 4.25$^{ac}$ |
| 1:4 | 0.0225 ± 0.0003$^{ac}$ | 0.0248 ± 0.0007$^{ac}$ | 29.49 ± 2.00$^{ac}$ | 33.93 ± 4.26$^{ac}$ |
| 1:6 | 0.0224 ± 0.0004$^{ac}$ | 0.0247 ± 0.0006$^{ac}$ | 29.99 ± 3.28$^{ac}$ | 34.53 ± 4.18$^{ac}$ |
| 1:8 | 0.0224 ± 0.0006$^{ac}$ | 0.0247 ± 0.0009$^{ac}$ | 30.10 ± 2.58$^{ac}$ | 34.80 ± 3.48$^{ac}$ |
| 2:1 | 0.0239 ± 0.0005$^{acdf}$ | 0.0261 ± 0.0009$^{cdf}$ | 18.68 ± 3.99$^{acdf}$ | 23.17 ± 3.39$^{acdf}$ |
| 4:1 | 0.0232 ± 0.0004$^{acef}$ | 0.0255 ± 0.0007$^{aceg}$ | 25.32 ± 3.08$^{acef}$ | 27.94 ± 3.74$^{acdf}$ |
| 6:1 | 0.0228 ± 0.0007$^{ac}$ | 0.0252 ± 0.0009$^{ac}$ | 28.59 ± 2.77$^{ac}$ | 33.11 ± 4.36$^{ac}$ |
| 8:1 | 0.0227 ± 0.0008$^{ac}$ | 0.0246 ± 0.0007$^{ac}$ | 29.61 ± 2.64$^{ac}$ | 33.88 ± 3.55$^{ac}$ |

Figure 31:
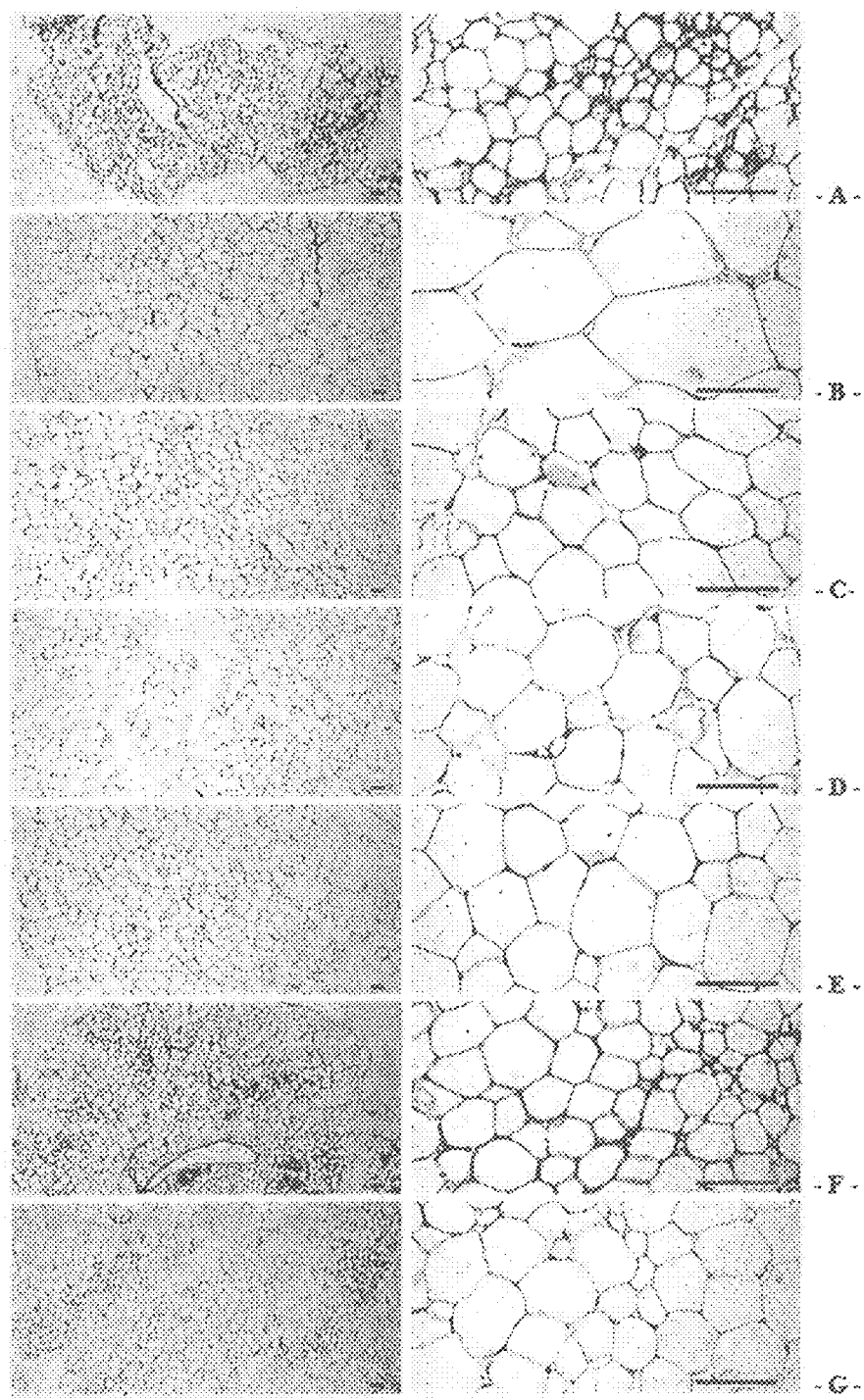
FIGS. 31 and 32 show histological images of adipocytes of fat within abdominal cavities of sham control or OVX ddY mice. A shows sham control, B shows OVX control, C shows 17β-estradiol 0.03 ug/head treated OVX mice, D shows red clover extract 120 mg/kg administered group, E shows pomegranate extract 120 mg/kg administered group, F shows red clover:pomegranate extract 1:1 mixture (g/g) 120 mg/kg (60:60 mg/kg) administered group, G shows red clover:pomegranate extract 1:2 mixture (g/g) 120 mg/kg (40:80 mg/kg) administered group, H shows red clover:pomegranate extract 1:4 mixture (g/g) 120 mg/kg (24:96 mg/kg) administered group, I shows red clover:pomegranate extract 1:6 mixture (g/g) 120 mg/kg (17:103 mg/kg) administered group, J shows red clover:pomegranate extract 1:8 mixture (g/g) 120 mg/kg (13:107 mg/kg) administered group, K shows red clover:pomegranate extract 2:1 mixture (g/g) 120 mg/kg (80:40 mg/kg) administered group, L shows red clover:pomegranate extract 4:1 mixture (g/g) 120 mg/kg (96:24 mg/kg) administered group, M shows red clover:pomegranate extract 6:1 mixture (g/g) 120 mg/kg (103:17 mg/kg) administered group, N shows red clover:pomegranate extract 8:1 mixture (g/g) 120 mg/kg (107:13 mg/kg) administered group. (Scale bar=120 um)
Figure 32:
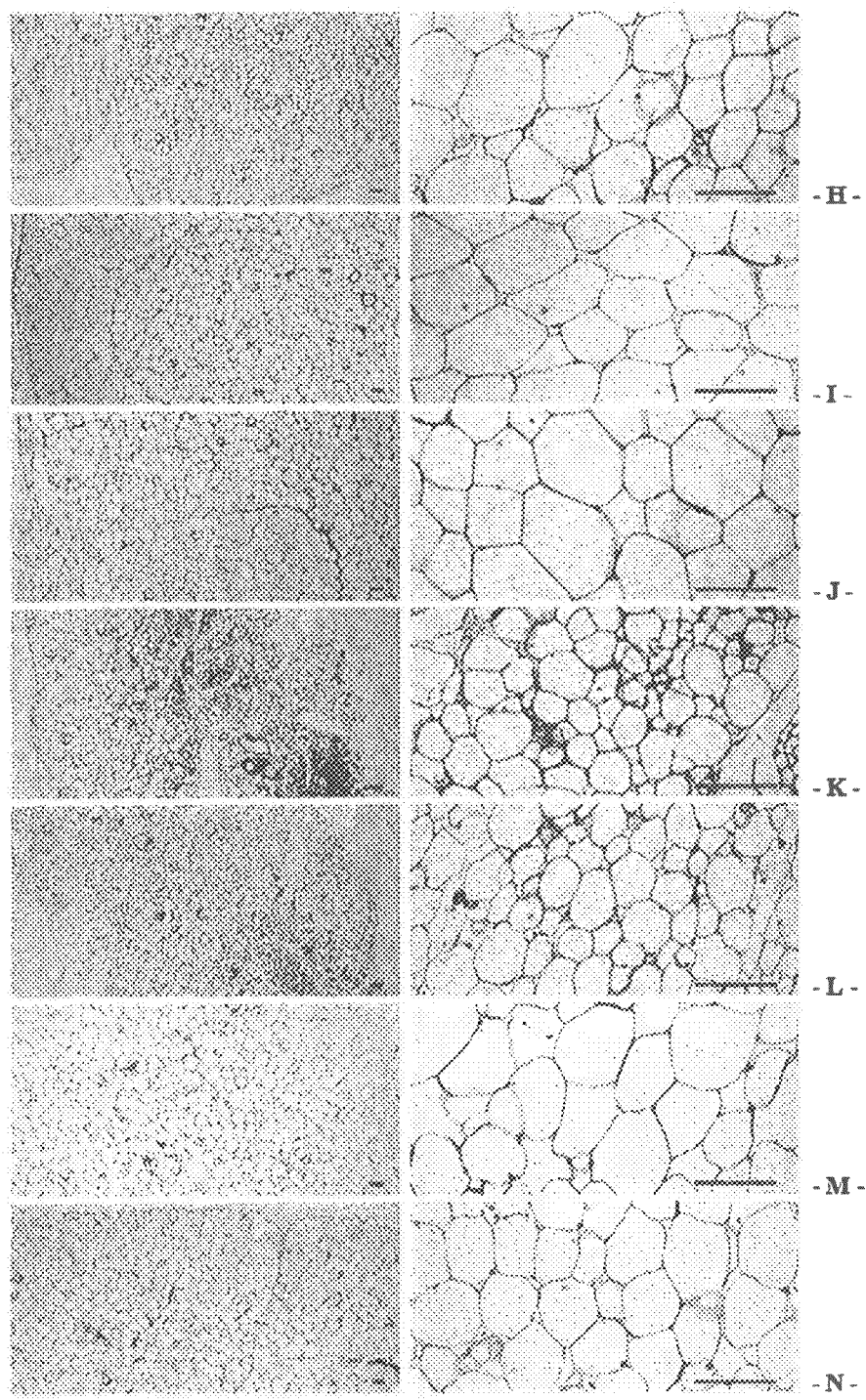

Values are expressed as mean ± standard deviation of 8 mice.
$^a$ $p < 0.01$ and
$^b$ $p < 0.05$: comparison with sham control according to LSD test
$^c$ $p < 0.01$: comparison with OVX control according to LSD test
$^d$ $p < 0.01$ and
$^e$ $p < 0.05$: comparison with red clover extract alone administered group according to LSD test
$^f$ $p < 0.01$ and
$^g$ $p < 0.05$: comparison with pomegranate extract alone administered group according to LSD test Example 3-13. Change in Bone Strength OVX control significantly ($p<0.01$) decreased in bone strength of femur mid-shaft region as compared to sham control, while significant ($p<0.01$ or $p<0.05$) increases in femur strength were each found in all candidate substance administered groups including red clover extract single formula as compared to OVX control. Particularly, significant ($p<0.01$ or $p<0.05$) increases in femur strength were found in the order of red clover:pomegranate extract 2:1, 1:1 and 4:1 (g/g) mixture administered groups as compared to of red clover:pomegranate extract 2:1, 1:1 and 4:1 (g/g) mixture administered groups as compared to each of red clover extract and pomegranate extract single formula administered groups (FIGS. 31 and 32).

In the case of OVX control, the abdominal fat pad thickness changed by 329.04% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by −52.23, −25.90, −22.25, −40.72, −23.97, −24.59, −24.45, −22.71, −55.21, −38.83, −26.54 and −25.98% respectively as compared to OVX control.

In the case of OVX control, the mean adipocyte diameter changed by 270.68% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by −48.06, −28.54, −25.14, −57.23, −31.57, −31.50, −27.72, −26.29, −63.70, −51.62, −28.55 and −27.24% respectively as compared to OVX control.

(2) Uterus

Figure 33:
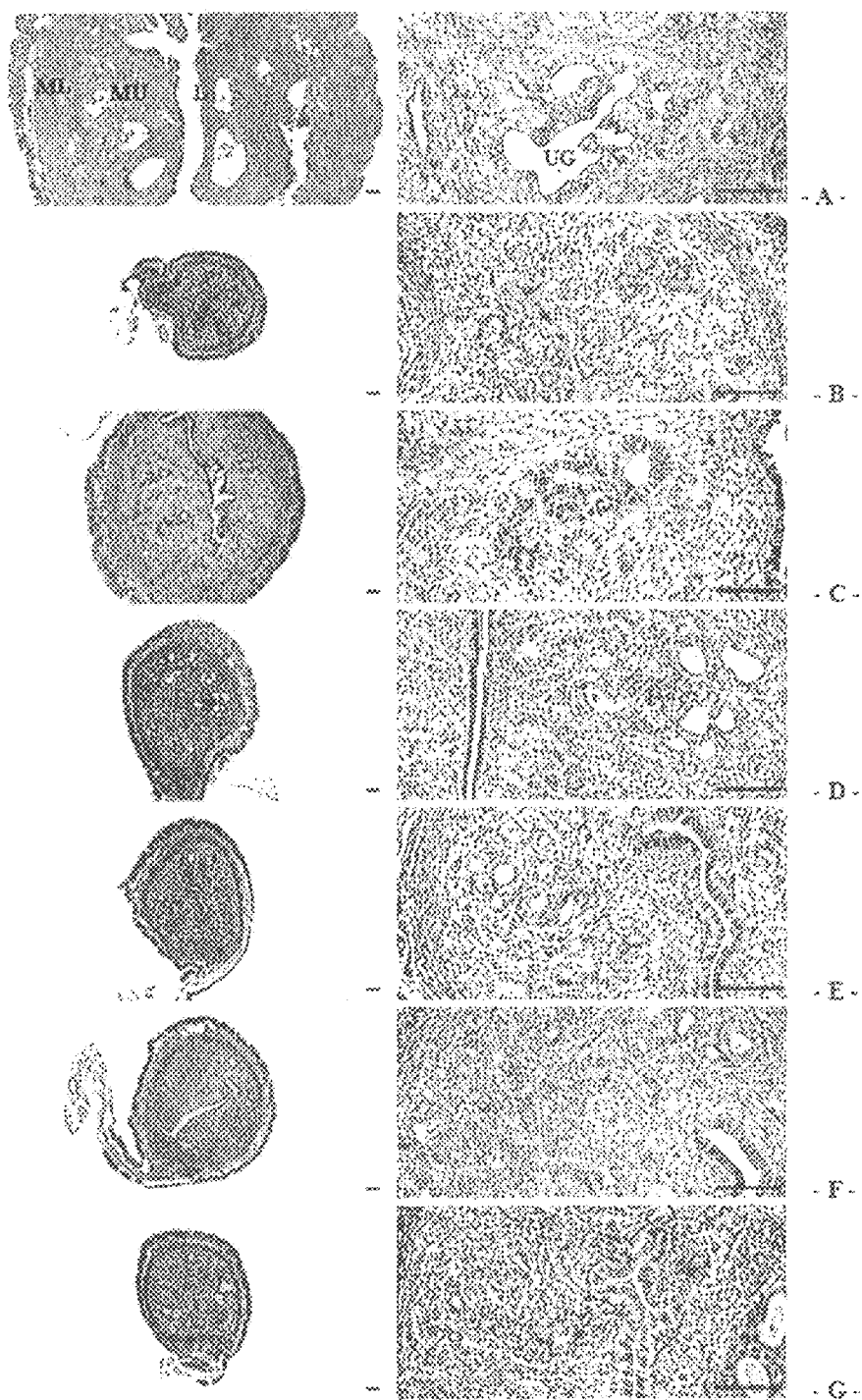
FIGS. 33 and 34 show histological images of left uterine horns taken from sham control or OVX ddY mice. A shows sham control, B shows OVX control, C shows 17β-estradiol 0.03 ug/head treated OVX mice, D shows red clover extract 120 mg/kg administered group, E shows pomegranate extract 120 mg/kg administered group, F shows red clover:pomegranate extract 1:1 mixture (g/g) 120 mg/kg (60:60 mg/kg) administered group, G shows red clover:pomegranate extract 1:2 mixture (g/g) 120 mg/kg (40:80 mg/kg) administered group, H shows red clover:pomegranate extract 1:4 mixture (g/g) 120 mg/kg (24:96 mg/kg) administered group, I shows red clover:pomegranate extract 1:6 mixture (g/g) 120 mg/kg (17:103 mg/kg) administered group, J shows red clover:pomegranate extract 1:8 mixture (g/g) 120 mg/kg (13:107 mg/kg) administered group, K shows red clover:pomegranate extract 2:1 mixture (g/g) 120 mg/kg (80:40 mg/kg) administered group, L shows red clover:pomegranate extract 4:1 mixture (g/g) 120 mg/kg (96:24 mg/kg) administered group, M shows red clover:pomegranate extract 6:1 mixture (g/g) 120 mg/kg (103:17 mg/kg) administered group, N shows red clover:pomegranate extract 8:1 mixture (g/g) 120 mg/kg (107:13 mg/kg) administered group. L represents Lumen; MU represents Mucosa; ML represents Muscular layer; Ep represents Epithelium; UG represents Uterine gland. (Scale bar=120 um)
Figure 34:
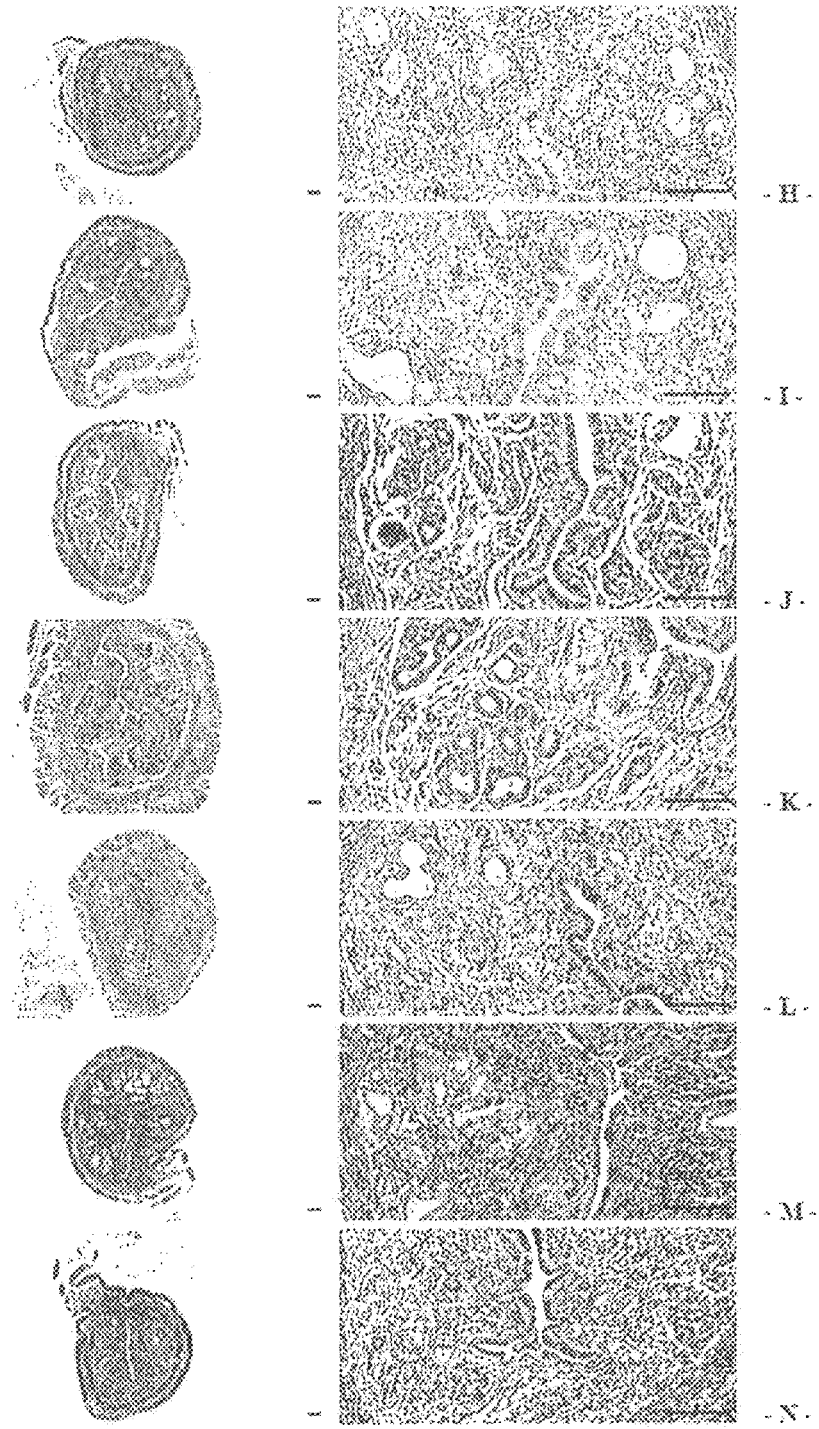

Disuse atrophy contributing to remarkable decreases in uterine mucosa occurred in OVX control, and significant (p<0.01) decreases in total, epithelium and mucosa thickness of uterus and percentage of uterine glands in the mucosa were each found in OVX control as compared to sham control, while significant (p<0.01 or p<0.05) increases in total, epithelium and mucosa thickness of uterus and percentage of uterine glands in the mucosa were each found in all candidate substance administered groups including 9 types of red clover:pomegranate extract mixed formulas as compared to OVX control, and particularly, significant (p<0.01 or p<0.05) increases in total, epithelium and mucosa thickness of uterus and percentage of uterine glands in the mucosa were found in the order of red clover:pomegranate extract 2:1, 1:1 and 4:1 (g/g) mixture administered groups as compared to each of red clover extract and pomegranate extract single formula administered groups (Table 22, FIGS. 33 and 34).

The mean thickness of uterus total and epithelium changed by −73.99 and −77.79% respectively in OVX control as compared to normal control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in uterus total mean thickness by 181.27, 37.05, 30.46, 77.23, 39.43, 37.12, 33.70, 31.79, 98.58, 61.95, 40.74 and 40.64% respectively, and changes in uterine epithelium mean thickness by 170.17, 51.29, 44.04, 133.75, 71.36, 62.15, 61.74, 46.04, 205.44, 119.58, 83.78 and 57.71% respectively, as compared to OVX control.

The mucosa mean thickness of uterus and percentage of uterine glands in the mucosa changed by −78.74 and −76.90% respectively in OVX control as compared to normal control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in uterine mucosa mean thickness by 196.04, 46.06, 39.48, 102.37, 55.72, 47.16, 44.15, 41.20, 125.29, 84.08, 53.63 and 53.00% respectively, and changes in percentage of uterine glands in the uterine mucosa by 180.37, 92.88, 80.37, 164.14, 109.49, 91.62, 84.40, 80.88, 186.05, 159.76, 112.69 and 98.34% respectively, as compared to OVX control.

TABLE 22

| Groups | Items Left uterine horn tissues | | | |
|---|---|---|---|---|
| | Total thickness (μm) | Epithelium thickness (μm) | Mucosa layer thickness (μm) | Uterine gland regions (%) |
| Controls | | | | |
| Sham | 2177.82 ± 573.19 | 34.58 ± 6.17 | 951.22 ± 242.86 | 53.94 ± 12.02 |
| OVX | 566.47 ± 128.78$^a$ | 7.68 ± 1.26$^a$ | 202.25 ± 46.58$^a$ | 12.46 ± 3.07$^a$ |
| Estradiol | 1593.32 ± 371.85$^{bc}$ | 20.75 ± 4.52$^{ac}$ | 598.74 ± 153.51$^{ac}$ | 34.93 ± 4.60$^{ac}$ |
| RC | 776.35 ± 97.07$^{ac}$ | 11.62 ± 3.02$^{ac}$ | 295.40 ± 45.06$^{ac}$ | 24.03 ± 6.13$^{ac}$ |
| PCP | 739.04 ± 84.66$^{ad}$ | 11.06 ± 2.72$^{ac}$ | 282.10 ± 37.26$^{ac}$ | 22.47 ± 4.28$^{ac}$ |
| RC:PCP | | | | |
| 1:1 | 1003.98 ± 173.11$^{aceg}$ | 17.96 ± 4.26$^{aceg}$ | 409.30 ± 31.93$^{aceg}$ | 32.91 ± 3.70$^{aceg}$ |
| 1:2 | 789.85 ± 116.09$^{ad}$ | 13.16 ± 4.17$^{ac}$ | 314.95 ± 79.42$^{ac}$ | 26.10 ± 6.70$^{ac}$ |
| 1:4 | 776.76 ± 98.02$^{ac}$ | 12.46 ± 3.50$^{ac}$ | 297.63 ± 45.24$^{ac}$ | 23.88 ± 3.85$^{ac}$ |
| 1:6 | 757.35 ± 66.86$^{ac}$ | 12.42 ± 4.31$^{ad}$ | 291.55 ± 34.89$^{ac}$ | 22.98 ± 5.17$^{ac}$ |
| 1:8 | 746.54 ± 64.96$^{ac}$ | 11.22 ± 2.41$^{ac}$ | 285.57 ± 40.39$^{ac}$ | 22.54 ± 4.56$^{ac}$ |
| 2:1 | 1124.93 ± 125.59$^{aceg}$ | 23.46 ± 4.93$^{aceg}$ | 455.64 ± 92.39$^{aceg}$ | 35.65 ± 6.07$^{aceg}$ |
| 4:1 | 917.42 ± 54.64$^{aceg}$ | 16.87 ± 4.11$^{aceg}$ | 372.29 ± 44.26$^{aceg}$ | 32.37 ± 4.67$^{acfg}$ |
| 6:1 | 797.22 ± 129.15$^{ac}$ | 14.12 ± 4.61$^{ac}$ | 310.71 ± 36.93$^{ac}$ | 26.50 ± 5.18$^{ac}$ |
| 8:1 | 796.67 ± 146.28$^{ac}$ | 12.11 ± 3.99$^{ad}$ | 309.44 ± 44.82$^{ac}$ | 24.71 ± 4.22$^{ac}$ |

Figure 35:
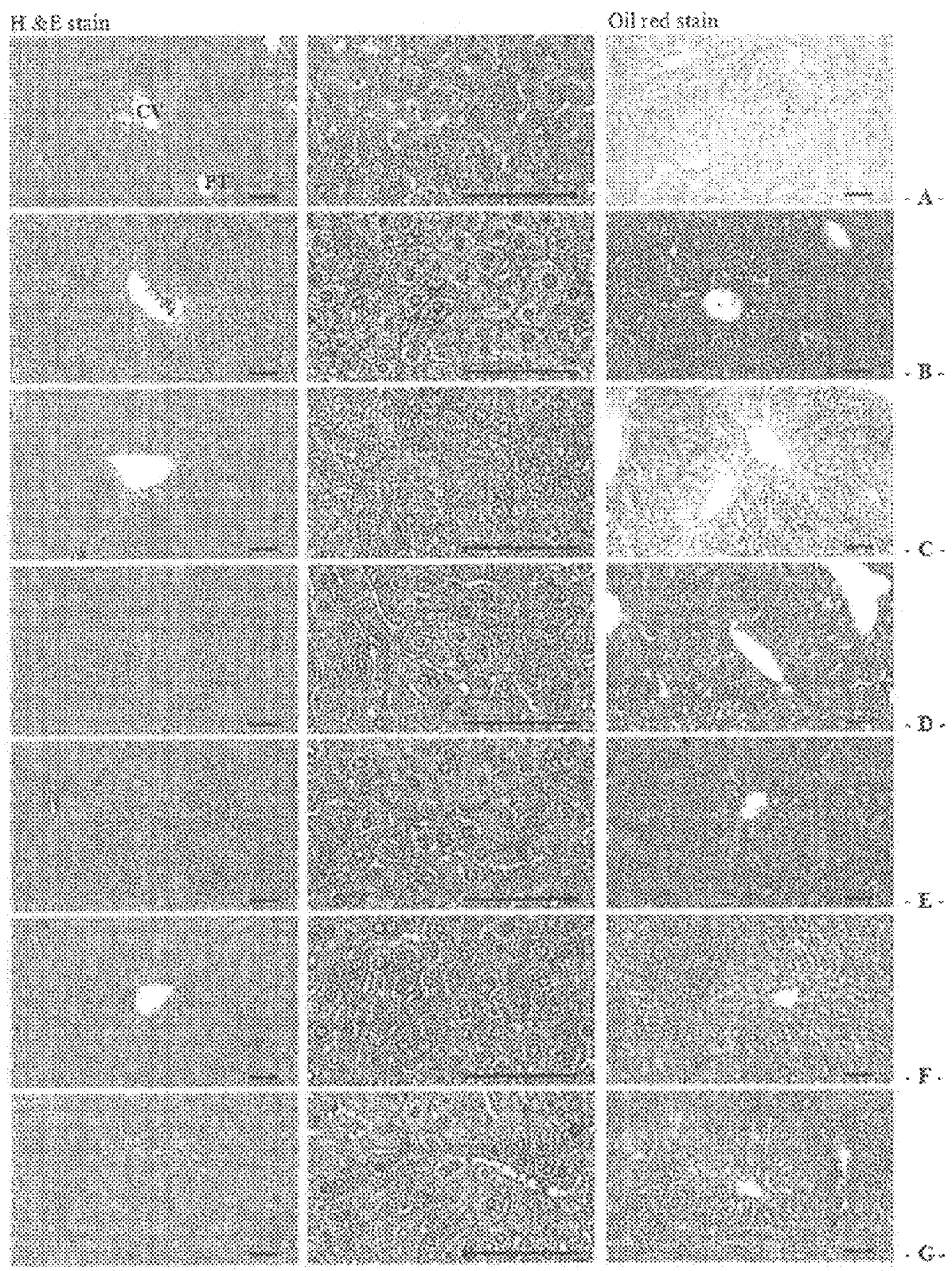
FIGS. 35 and 36 show histological images of left lateral lobes of livers taken from sham control or OVX ddY mice. A shows sham control, B shows OVX control, C shows 17β-estradiol 0.03 ug/head treated OVX mice, D shows red clover extract 120 mg/kg administered group, E shows pomegranate extract 120 mg/kg administered group, F shows red clover:pomegranate extract 1:1 mixture (g/g) 120 mg/kg (60:60 mg/kg) administered group, G shows red clover:pomegranate extract 1:2 mixture (g/g) 120 mg/kg (40:80 mg/kg) administered group, H shows red clover:pomegranate extract 1:4 mixture (g/g) 120 mg/kg (24:96 mg/kg) administered group, I shows red clover:pomegranate extract 1:6 mixture (g/g) 120 mg/kg (17:103 mg/kg) administered group, J shows red clover:pomegranate extract 1:8 mixture (g/g) 120 mg/kg (13:107 mg/kg) administered group, K shows red clover:pomegranate extract 2:1 mixture (g/g) 120 mg/kg (80:40 mg/kg) administered group, L shows red clover:pomegranate extract 4:1 mixture (g/g) 120 mg/kg (96:24 mg/kg) administered group, M shows red clover:pomegranate extract 6:1 mixture (g/g) 120 mg/kg (103:17 mg/kg) administered group, N shows red clover:pomegranate extract 8:1 mixture (g/g) 120 mg/kg (107:13 mg/kg) administered group. CV represents Central vein; PT represents Portal Triad. (Scale bar=120 um)
Figure 36:
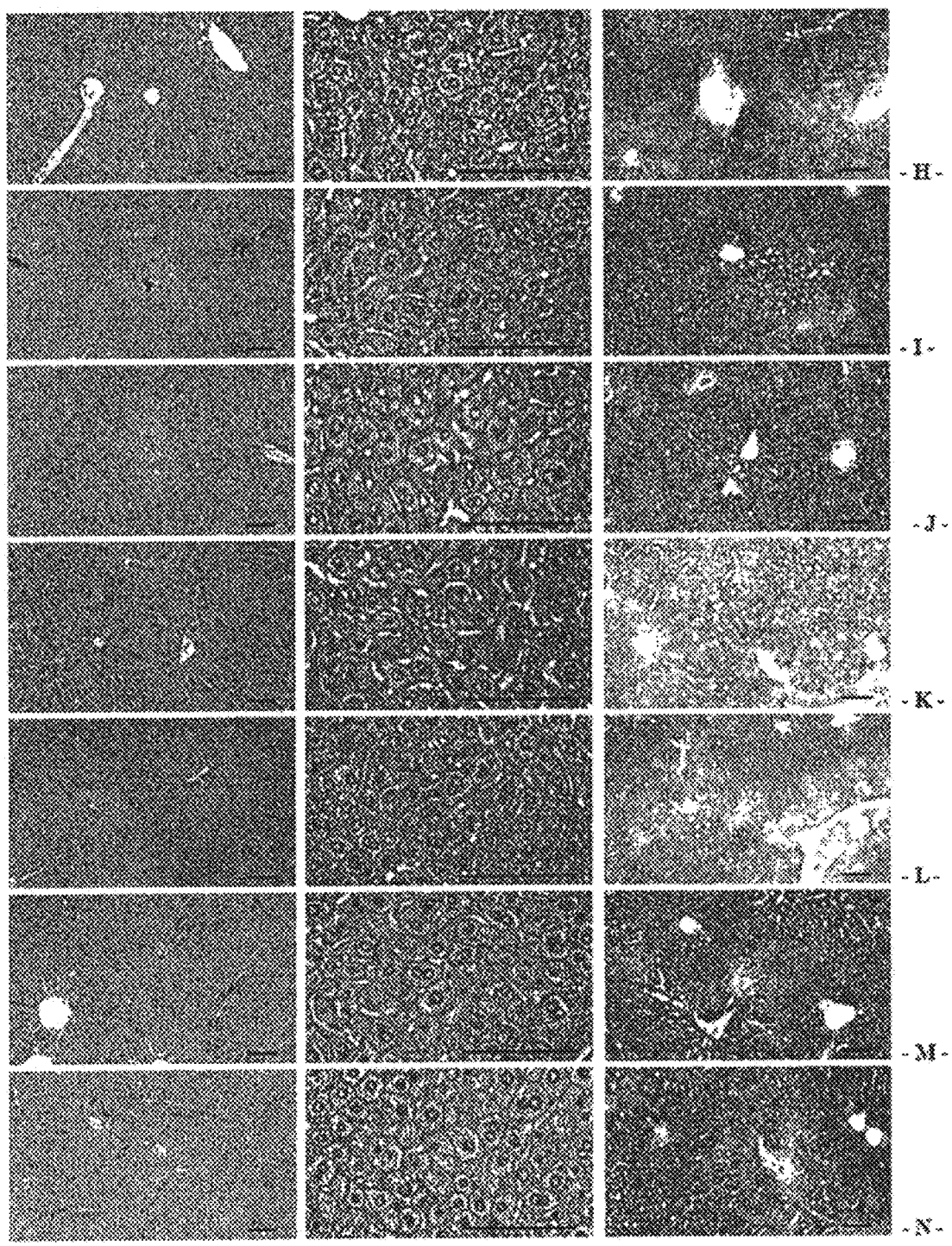

$^a$p < 0.01 and
$^b$p < 0.05: comparison with sham control according to MW test
$^c$p < 0.01 and
$^d$p < 0.05: comparison with OVX control according to MW test
$^e$p < 0.01 and
$^f$p < 0.05: comparison with red clover extract alone administered group according to MW test
$^g$p < 0.01: comparison with pomegranate extract alone administered group according to MW test (3) Liver Hepatic steatosis characterized by hypertrophy caused by remarkable fat deposition in hepatocytes occurred in OVX control, and significant (p<0.01) increases in region with hepatic fatty degeneration and mean hepatocyte diameter were each found in OVX control as compared to sham control, while significant (p<0.01) decreases in hepatic steatosis were each found in all test substance administered groups including estradiol as compared to OVX control, and particularly, significant (p<0.01) decreases in region with hepatic fatty degeneration and mean hepatocyte diameter were found in the order of red clover:pomegranate extract 2:1, 1:1 and 4:1 (g/g) mixture administered groups as compared to each of red clover extract and pomegranate extract single formula administered groups (Table 23, FIGS. 35 and 36).

Region with hepatic fatty degeneration and mean hepatocyte diameter changed by 500.66 and 224.65% respectively in OVX control as compared to normal control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in region with hepatic fatty degeneration by −44.73, −24.38, −21.08, −43.20, −25.72, −23.91, −23.20, −22.21, −51.85, −41.47, −27.38 and −23.67% respectively, and changes in mean hepatocyte diameter by −42.21, −26.50, −25.88, −49.87, −30.22, −30.02, −29.80, −25.35, −55.39, −45.10, −27.18 and −26.68% respectively, as compared to OVX control.

TABLE 23

| Groups | Abdominal fat pads | | Hepatic tissues | |
|---|---|---|---|---|
| | Total thickness (μm) | Mean adipocyte diameters (μm) | Steatosis regions (%) | Mean hepatocyte diameters (μm) |
| Controls | | | | |
| Sham | 1.41 ± 0.45 | 35.05 ± 10.25 | 13.08 ± 3.16 | 9.83 ± 3.34 |
| OVX | 6.04 ± 0.75$^a$ | 129.93 ± 24.06$^a$ | 78.58 ± 6.76$^a$ | 31.93 ± 4.92$^a$ |
| Estradiol | 2.89 ± 0.27$^{ac}$ | 67.49 ± 14.77$^{ac}$ | 43.43 ± 6.53$^{ac}$ | 18.45 ± 3.66$^{ac}$ |
| RC | 4.48 ± 0.51$^{ac}$ | 92.85 ± 12.70$^{ac}$ | 59.42 ± 7.08$^{ac}$ | 23.47 ± 3.83$^{ac}$ |
| PCP | 4.70 ± 0.63$^{ac}$ | 97.27 ± 15.68$^{ac}$ | 62.01 ± 7.82$^{ac}$ | 23.66 ± 3.59$^{ac}$ |
| RC:PCP | | | | |
| 1:1 | 3.58 ± 0.49$^{acdf}$ | 55.57 ± 12.55$^{acdf}$ | 44.63 ± 6.94$^{acdf}$ | 16.00 ± 3.73$^{acdf}$ |
| 1:2 | 4.59 ± 0.45$^{ac}$ | 88.91 ± 15.64$^{ac}$ | 58.37 ± 7.54$^{ac}$ | 22.28 ± 4.15$^{ac}$ |
| 1:4 | 4.55 ± 0.65$^{ac}$ | 89.01 ± 13.89$^{ac}$ | 59.80 ± 6.51$^{ac}$ | 22.34 ± 2.75$^{ac}$ |
| 1:6 | 4.56 ± 0.59$^{ac}$ | 93.91 ± 15.69$^{ac}$ | 60.35 ± 8.89$^{ac}$ | 22.41 ± 3.35$^{ac}$ |
| 1:8 | 4.67 ± 0.61$^{ac}$ | 95.77 ± 18.09$^{ac}$ | 61.13 ± 10.91$^{ac}$ | 23.83 ± 2.67$^{ac}$ |
| 2:1 | 2.71 ± 0.93$^{acdf}$ | 47.17 ± 10.84$^{cdf}$ | 37.84 ± 9.05$^{acdf}$ | 14.24 ± 4.07$^{bcdf}$ |
| 4:1 | 3.69 ± 0.50$^{acef}$ | 62.87 ± 14.30$^{acdf}$ | 45.99 ± 8.44$^{acdf}$ | 17.53 ± 3.43$^{acdf}$ |
| 6:1 | 4.44 ± 0.53$^{ac}$ | 92.84 ± 14.14$^{ac}$ | 57.06 ± 7.96$^{ac}$ | 23.25 ± 4.91$^{ac}$ |
| 8:1 | 4.47 ± 0.75$^{ac}$ | 94.54 ± 14.59$^{ac}$ | 59.98 ± 7.88$^{ac}$ | 23.41 ± 4.31$^{ac}$ |

Figure 37:
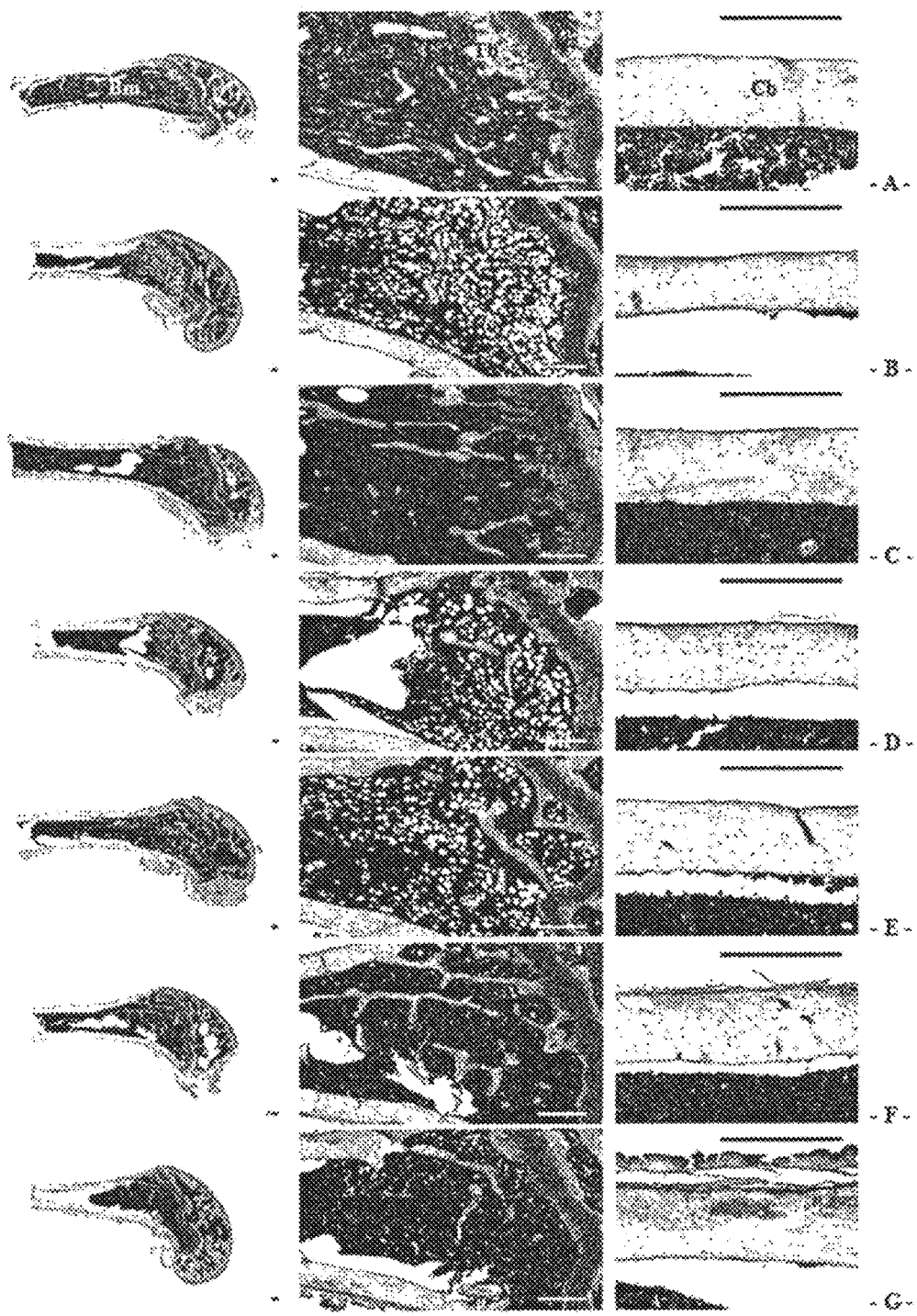
FIGS. 37 and 38 show histological profiles of left femurs taken from sham control or OVX ddY mice. A shows sham control, B shows OVX control, C shows 17β-estradiol 0.03 ug/head treated OVX mice, D shows red clover extract 120 mg/kg administered group, E shows pomegranate extract 120 mg/kg administered group, F shows red clover:pomegranate extract 1:1 mixture (g/g) 120 mg/kg (60:60 mg/kg) administered group, G shows red clover:pomegranate extract 1:2 mixture (g/g) 120 mg/kg (40:80 mg/kg) administered group, H shows red clover:pomegranate extract 1:4 mixture (g/g) 120 mg/kg (24:96 mg/kg) administered group, I shows red clover:pomegranate extract 1:6 mixture (g/g) 120 mg/kg (17:103 mg/kg) administered group, J shows red clover:pomegranate extract 1:8 mixture (g/g) 120 mg/kg (13:107 mg/kg) administered group, K shows red clover:pomegranate extract 2:1 mixture (g/g) 120 mg/kg (80:40 mg/kg) administered group, L shows red clover:pomegranate extract 4:1 mixture (g/g) 120 mg/kg (96:24 mg/kg) administered group, M shows red clover:pomegranate extract 6:1 mixture (g/g) 120 mg/kg (103:17 mg/kg) administered group, N shows red clover:pomegranate extract 8:1 mixture (g/g) 120 mg/kg (107:13 mg/kg) administered group. Cb represents cortical bone; Tb represents trabecular bone; Bm represents bone marrow; Gp represents growth plate. (Scale bar=240 um)
Figure 38:
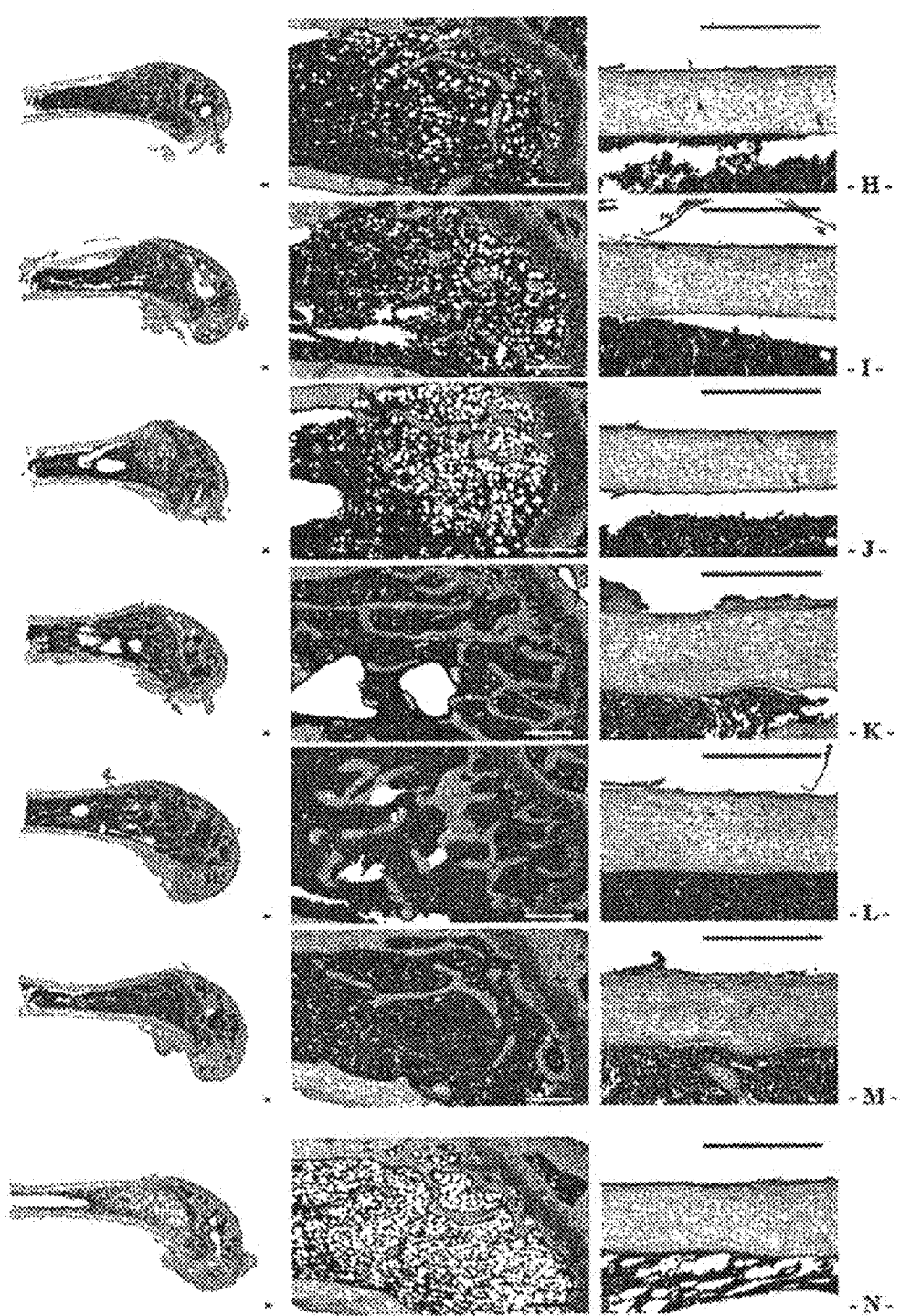

Values are expressed as mean ± standard deviation of 8 mice.
$^a$p < 0.01 and
$^b$p < 0.05: comparison with sham control according to LSD test
$^c$p < 0.01: comparison with OVX control according to LSD test
$^d$p < 0.01 and
$^e$p < 0.05: comparison with red clover extract alone administered group according to LSD test
$^f$p < 0.01: comparison with pomegranate extract alone administered group according to LSD test Example 3-15. Histological Change (2): Femur Trabecular bone and cortical bone developed relatively well were observed in femur of sham operated group, while decreases in trabecular bone and cortical bone mass caused by remarkable increases in number and activity of osteoclast cells were found in OVX control, but remarkable increases in bone mass and thickness of trabecular bone and cortical bone caused by osteoclast cell activity inhibition of femur were found in all test substance administered groups including red clover extract single formula, and particularly, remarkable osteoclast cell activity inhibition and bone mass preservation effects were provided in the order of red clover:pomegranate extract 2:1, 1:1 and 4:1 (g/g) mixture administered groups as compared to each of red clover extract and pomegranate extract single formula administered groups (Tables 24, 25 and FIGS. 37, 38).

(1) Bone Mass and Structure

OVX control significantly (p<0.01) decreased in each of the trabecular bone mass, mean trabecular bone length, thickness and number, and cortical bone thickness of midshaft region of femur as compared to sham control, while significant (p<0.01 or p<0.05) increases in femur trabecular bone mass, mean trabecular bone length, thickness and number, cortical bone thickness were found in all candidate substance administered groups including pomegranate extract single formula as compared to OVX control, and particularly, significant (p<0.01) increases in femur trabecular bone mass, mean trabecular bone length, thickness and number, and cortical bone thickness were found in the order of red clover:pomegranate extract 2:1, 1:1 and 4:1 (g/g) mixture administered groups as compared to each red clover extract and pomegranate extract single formula administered groups.

The trabecular bone mass and mean trabecular bone number of femur changed by −53.66 and −59.41% respectively in OVX control as compared to normal control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in trabecular bone mass by 73.01, 32.47, 25.54, 59.92, 31.08, 30.51, 26.55, 26.42, 81.75, 58.54, 33.70 and 30.75% respectively, and changes in mean trabecular bone number by 92.68, 46.34, 36.59, 102.44, 46.34, 43.90, 36.59, 34.15, 139.02, 97.56, 53.66 and 46.34% respectively, as compared to OVX control.

The mean length and thickness of femur trabecular bone changed by −53.47 and −55.82% respectively in OVX control as compared to normal control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes in mean length of trabecular bone by 89.04, 23.62, 20.88, 79.43, 27.47, 26.57, 25.18, 21.16, 99.20, 72.68, 27.65 and 24.04% respectively, and changes in mean thickness of trabecular bone by 70.56, 35.69, 33.29, 104.28, 44.40, 43.67, 34.65, 34.98, 129.10, 101.26, 40.19 and 37.58% respectively, as compared to OVX control.

In the case of OVX control, the femur cortical bone thickness changed by −27.80% as compared to sham control, and estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula administered groups had changes by 21.85, 16.11, 13.83, 25.23, 18.97, 16.70, 15.84, 15.01, 30.43, 24.33, 20.10 and 14.00% respectively as compared to OVX control.

TABLE 24

| Groups | Items Left femur tissues | | | |
|---|---|---|---|---|
| | TV/BV | Tbn | Tbl | Tbt |
| Controls | | | | |
| Sham | 37.28 ± 5.04 | 12.63 ± 1.69 | 1029.36 ± 145.55 | 73.44 ± 11.98 |
| OVX | 17.28 ± 2.91$^a$ | 5.13 ± 0.64$^e$ | 478.99 ± 80.94$^e$ | 32.45 ± 7.07$^e$ |
| Estradiol | 29.89 ± 5.24$^{ab}$ | 9.88 ± 1.36$^{eg}$ | 905.51 ± 146.34$^g$ | 55.34 ± 8.99$^{eg}$ |
| RC | 22.89 ± 2.05$^{ab}$ | 7.50 ± 0.93$^{eg}$ | 592.13 ± 35.08$^{eg}$ | 44.03 ± 3.97$^{eg}$ |
| PCP | 21.69 ± 1.85$^{ab}$ | 7.00 ± 1.20$^{eg}$ | 578.99 ± 39.41$^{eg}$ | 43.25 ± 2.49$^{eg}$ |
| RC:PCP | | | | |
| 1:1 | 27.63 ± 2.47$^{abcd}$ | 10.38 ± 1.30$^{gij}$ | 859.44 ± 173.38$^{egij}$ | 66.28 ± 14.40$^{gij}$ |
| 1:2 | 22.65 ± 2.58$^{ab}$ | 7.50 ± 0.76$^{eg}$ | 610.56 ± 60.98$^{eg}$ | 46.85 ± 8.26$^{eg}$ |
| 1:4 | 22.55 ± 2.72$^{ab}$ | 7.38 ± 0.92$^{eg}$ | 606.29 ± 36.21$^{eg}$ | 46.62 ± 8.71$^{eh}$ |
| 1:6 | 21.86 ± 2.30$^{ab}$ | 7.00 + 1.07$^{eg}$ | 599.59 ± 55.83$^{eg}$ | 43.69 ± 3.85$^{eg}$ |
| 1:8 | 21.84 ± 1.57$^{ab}$ | 6.88 ± 0.83$^{eg}$ | 580.37 ± 66.93$^{eh}$ | 43.80 ± 5.38$^{eg}$ |
| 2:1 | 31.40 ± 4.14$^{abcd}$ | 12.25 ± 1.04$^{egij}$ | 954.18 ± 140.48$^{gij}$ | 74.33 ± 14.63$^{gij}$ |
| 4:1 | 27.39 ± 3.68$^{abcd}$ | 10.13 ± 1.89$^{gij}$ | 827.11 ± 142.28$^{fgij}$ | 65.30 ± 11.84$^{gij}$ |
| 6:1 | 23.10 ± 2.83$^{ab}$ | 7.88 ± 0.83$^{eg}$ | 611.46 ± 38.35$^{eg}$ | 45.49 ± 5.74$^{eg}$ |
| 8:1 | 22.59 ± 3.67$^{ab}$ | 7.50 ± 0.93$^{eg}$ | 594.17 ± 49.46$^{eg}$ | 44.64 ± 3.53$^{eg}$ |

Values are expressed as mean ± standard deviation of 8 mice.
$^a$p < 0.01: comparison with sham control according to LSD test
$^b$p < 0.01: comparison with OVX control according to LSD test
$^c$p < 0.01: comparison with red clover extract alone administered group according to LSD test
$^d$p < 0.01: comparison with pomegranate extract alone administered group according to LSD test
$^e$p < 0.01 and
$^f$p < 0.05: comparison with sham control according to MW test
$^g$p < 0.01 and
$^h$p < 0.05: comparison with OVX control according to MW test
$^i$p < 0.01: comparison with red clover extract alone administered group according to MW test
$^j$p < 0.01: comparison with pomegranate extract alone administered group according to MW test (2) Bone Resorption In the case of OVX control, the osteoclast cell number and ratio (OS/BS) of femur significantly (p<0.01) increased as compared to sham control, while significant (p<0.01 or p<0.05) decreases in femur osteoclast cell number and OS/BS were each found in all test substance administered groups including 9 types of red clover:pomegranate extract mixed formulas as compared to OVX control, and particularly, significant (p<0.01) decreases in femur osteoclast cell number and OS/BS were found in the order of red clover: pomegranate extract 2:1, 1:1 and 4:1 (g/g) mixture administered groups as compared to each of red clover extract and pomegranate extract single formula administered groups.

In OVX control, the osteoclast cell number and OS/BS of femur changed by 209.09 and 146.31% respectively as compared to normal control, and estradiol, red clover extract and pomegranate extract single formula, and red clover: pomegranate extract 1:1, 1:2, 1:4, 1:6, 1:8, 2:1, 4:1, 6:1 and 8:1 (g/g) mixed formula administered groups had changes in osteoclast cell number by −55.15, −19.12, −16.91, −46.32, −23.53, −20.59, −19.85, −18.38, −58.82, −44.85, −21.32 and −19.85% respectively, and changes in OS/BS by −37.50, −18.29, −15.47, −35.88, −20.81, −18.67, −15.92, −20.12, −45.43, −35.05, −17.87 and −15.10% respectively, as compared to OVX control.

TABLE 25

| Groups | Items Left femur tissues | | |
|---|---|---|---|
| | Cbt | Ocn | OS/BS |
| Controls | | | |
| Sham | 209.33 ± 18.14 | 5.50 ± 0.93 | 8.52 ± 1.57 |
| OVX | 151.14 ± 11.14$^e$ | 17.00 ± 2.00$^a$ | 21.00 ± 2.39$^e$ |
| Estradiol | 184.17 ± 8.40$^{eg}$ | 7.63 ± 1.06$^{ab}$ | 13.12 ± 1.41$^{eg}$ |
| RC | 175.49 ± 4.41$^{eg}$ | 13.75 ± 1.49$^{ac}$ | 17.16 ± 1.89$^{eg}$ |
| PCP | 172.05 ± 8.17$^{eg}$ | 14.13 ± 1.64$^{ac}$ | 17.75 ± 1.46$^{eg}$ |
| RC:PCP | | | |
| 1:1 | 189.27 ± 7.10$^{gij}$ | 9.13 ± 1.13$^{abcd}$ | 13.46 ± 1.88$^{egij}$ |
| 1:2 | 179.81 ± 8.89$^{eg}$ | 13.00 ± 1.85$^{ab}$ | 16.63 ± 1.74$^{eg}$ |
| 1:4 | 176.39 ± 9.83$^{eg}$ | 13.50 ± 1.51$^{ab}$ | 17.08 ± 1.65$^{eg}$ |
| 1:6 | 175.08 ± 10.48$^{eg}$ | 13.63 ± 1.51$^{ab}$ | 17.65 ± 1.26$^{eg}$ |
| 1:8 | 173.84 ± 9.20$^{eg}$ | 13.88 ± 1.89$^{ab}$ | 16.77 ± 3.23$^{eh}$ |
| 2:1 | 197.13 ± 9.00$^{gij}$ | 7.00 ± 0.76$^{bcd}$ | 11.46 ± 1.37$^{egij}$ |
| 4:1 | 187.92 ± 10.08$^{fgij}$ | 9.38 ± 1.30$^{abcd}$ | 13.64 ± 1.99$^{egij}$ |
| 6:1 | 181.52 ± 12.63$^{eg}$ | 13.38 ± 1.69$^{ab}$ | 17.24 ± 1.48$^{eg}$ |
| 8:1 | 172.30 ± 6.68$^{eg}$ | 13.63 ± 2.33$^{ab}$ | 17.82 ± 0.98$^{eg}$ |

Values are expressed as mean ± standard deviation of 8 mice.
$^a$p < 0.01: comparison with sham control according to LSD test
$^b$p < 0.01: comparison with OVX control according to LSD test
$^c$p < 0.01: comparison with red clover extract alone administered group according to LSD test
$^d$p < 0.01 comparison with pomegranate extract alone administered group according to LSD test
$^e$p < 0.01 and
$^f$p < 0.05: comparison with sham control according to MW test
$^g$p < 0.01 and
$^h$p < 0.05: comparison with OVX control according to MW test
$^i$p < 0.01: comparison with red clover extract alone administered group according to MW test
$^j$p < 0.01: comparison with pomegranate extract alone administered group according to MW test Summary of Example 3

In the study, optimal mixture formula of red clover extract and pomegranate extract was evaluated using OVX ddY mouse model being currently used as experimental animal model for various menopausal disorders including osteoporosis [Yamaguchi et al., 1999; Ku and Lee, 2005; Han et al., 2007; Shin et al., 2007]. That is, from 28 days after OVX, red clover extract and pomegranate extract single formula, and 9 types of red clover:pomegranate extract mixed formulas (1:1, 1:2, 1:4, 1:6, 1:8, 2:1, 4:1, 6:1 and 8:1, g/g) 120 mg/kg was dissolved in or diluted with sterile distilled water and orally administered at a dose of 10 ml/kg once daily for 84 days, and evaluation was based on 5 pharmacological effects including an estrogen-like effect, an anti-obesity effect, a hyperlipidemia inhibitory effect, a protective effect against fatty liver and an osteoporosis inhibitory effect. To evaluate the estrogen-like effect and anti-obesity effect, changes in body weight and body weight gain, water and food consumption, amounts of body fat and abdominal fat, serum estradiol level, and weights of abdominal fat pad and uterus were evaluated together with histological changes such as abdominal fat pad thickness and mean adipocyte diameter, thickness of uterus total, epithelium and mucosa, and percentage of uterine glands in the mucosa, and the protective effect against fatty liver was evaluated by measuring liver weight, serum AST and ALT levels and histological change (mean hepatocyte diameter and region with hepatic degeneration showing fatty change), the hyperlipidemia alleviation effect was evaluated using changes in serum TC, LDL, HDL and TG levels, and to evaluate the osteoporosis reduction effect, namely, the bone protective effect, histological changes in wet, dry and ash weights of femur, BMD, bone strength, serum osteocalcin and bALP levels, femur bone mass and structure, and bone resorption were each measured. In the experiment, mixed formula showing statistically significant ($p<0.01$ or $p<0.05$) increases in efficacy at the same time when compared to each of red clover extract and pomegranate extract single formula was determined as red clover:pomegranate extract mixed formula showing a synergistic effect, and evaluation was conducted by comparing to results in 17β-estradiol 0.03 μg/head/day subcutaneously administered mice [Chiba et al., 2003; Murakami et al., 2007; Tousen et al., 2011].

The administration dose of mixed formula used in the experiment was set higher 12 times than a human clinical dose of 600 mg, i.e., 600 mg/60 kg)×12=120 mg/kg, in consideration of a body surface area of mouse, and the dose of each of red clover extract and pomegranate extract single formula was also set as 120 mg/kg for direct comparative evaluation of efficacy, and according to earlier researchers' method [Chiba et al., 2003; Murakami et al., 2007; Tousen et al., 2011], 0.03 μg of 17β-estradiol was dissolved in 0.2 ml of sterile saline and subcutaneously administered to back skin at a dose of 0.2 ml/mouse (0.03 μg/head/day) once daily for 84 days from 28 days after OVX surgery.

As a result of the experiment, remarkable increases in body weight and body weight gain, food consumption, amounts of body fat and abdominal fat, abdominal fat pad weight, serum AST, ALT, TC, LDL, TG and osteocalcin levels, and decreases in uterus, liver and femur weights, serum bALP and estradiol levels, mean total body bone mineral density and femur bone mineral density were found in OVX control as compared to sham vehicle control, and indication of remarkable increases in abdominal fat pad thickness and hypertrophy of adipocytes, hepatic steatosis, disuse atrophy of uterus, and decreases in bone mass of femur was each histologically detected together with remarkable increases of bone resorption marker (Ocn and OS/BS), so typical estrogen deficient menopausal disorders (obesity, hyperlipidemia, hepatic steatosis and osteoporosis) were induced by OVX. On the other hand, signs of menopausal disorders related to estrogen deficient menopause induced by OVX were remarkably inhibited by continuous administration of estradiol, red clover extract and pomegranate extract single formula, and all 9 types of red clover:pomegranate extract mixed formulas for 84 days, and particularly, a significant effect on reduction of on estrogen deficient menopausal disorders induced by OVX such as obesity, hyperlipidemia, hepatic steatosis and osteoporosis was provided in the order of red clover:pomegranate extract 2:1, 1:1 and 4:1 (g/g) mixture administered groups as compared to each of red clover extract and pomegranate extract single formula administered groups. Accordingly, it was observed that red clover:pomegranate extract mixture formula at an optimal ratio—red clover:pomegranate extract 2:1, 1:1 and 4:1 even synergistically increased an effect of red clover extract and pomegranate extract on reduction of OVX induced menopausal disorders through increased diversity of isoflavonoids contained, and among them, it was observed that red clover:pomegranate extract 2:1 mixed formula synergistically increased a best menopausal disorder reduction effect, but the present disclosure is not limited thereto.

In the study, food consumption remarkably increased due to OVX, resulting in remarkable increases in body weight as well as fat deposition and hypertrophy of adipocytes. On the other hand, signs of estrogen deficient obesity induced by OVX were remarkably inhibited by continuous administration of each of red clover extract and pomegranate extract single formula, and all 9 types of red clover:pomegranate extract mixed formulas for 84 days, and particularly, red clover:pomegranate extract 2:1, 1:1 and 4:1 (g/g) mixture administered group in a sequential order showed presumably significant inhibition of body fat deposition, adipocyte hypertrophy and body weight increase as compared to each of red clover extract and pomegranate extract single formula administered groups. These results serve as an evidence demonstrating that red clover:pomegranate extract mixed formula at an optimal ratio—red clover:pomegranate extract 2:1, 1:1 and 4:1 synergistically increases an effect of red clover extract and pomegranate extract on reduction of obesity related to menopausal disorders, and among them, it was observed that red clover:pomegranate extract 2:1 (g/g) mixed formula showed a best anti-obesity effect, but the present disclosure is not limited thereto.

In the study, due to OVX, significant decreases in uterus weight and significant decreases in serum estradiol level occurred, and histologically remarkable decreases in uterus total, mucosa and epithelium thickness and decreases in uterine glands in the mucosa occurred. On the other hand, signs of estrogen deficient uterus atrophy were remarkably inhibited by administration of estradiol, red clover extract and pomegranate extract single formula, red clover:pomegranate extract 1:1, 1:2, 1:4, 1:6, 1:8, 2:1, 4:1, 6:1 and 8:1 (g/g) mixed formula, and particularly, red clover:pomegranate extract 2:1, 1:1 and 4:1 (g/g) mixture administered group in a sequential order showed significant increases in serum estradiol level and presumable inhibition of uterus atrophy as compared to each of red clover extract and pomegranate extract single formula administered groups, which serves as an evidence demonstrating that red clover:pomegranate extract mixed formula at an optimal ratio—red clover:pomegranate extract 2:1, 1:1 and 4:1 synergistically increases an estrogenic effect of red clover extract and pomegranate extract through increased diversity of isoflavonoids contained, and among them, it was observed that red clover:pomegranate extract 2:1 (g/g) mixed formula showed a best estrogenic effect, but the present disclosure is not limited thereto.

In the study, the serum TC, LDL and TG levels were remarkably decreased and the HDL level was increased by subcutaneous administration of estradiol and oral administration of all red clover extract and pomegranate extract single or mixed formula, and particularly, significant increases in anti-hyperlipidemia effect were found in the order of red clover:pomegranate extract 2:1, 1:1 and 4:1 (g/g) mixture administered groups as compared to each of red clover extract and pomegranate extract single formula administered groups, which serves as an evidence demonstrating that red clover:pomegranate extract mixed formula at an optimal ratio—red clover:pomegranate extract 2:1, 1:1 and 4:1 synergistically increases an anti-hyperlipidemia effect of red clover extract and pomegranate extract at least under the experimental conditions via HMG-CoA, the enzyme involved in cholesterol synthesis [Di Croce et al., 1996], and among them, it was observed red clover:pomegranate extract 2:1 (g/g) mixed formula showed a best anti-hyperlipidemia effect, but the present disclosure is not limited thereto.

In the study, remarkable hepatic steatosis in OVX control was bio-chemically and histologically ascertained. On the other hand, signs of fatty liver induced by OVX were remarkably inhibited by administration of estradiol, red clover extract and pomegranate extract single formula, and 9 types of red clover:pomegranate extract mixed formulas, and particularly, significant increases in liver protective effect were found in the order of red clover:pomegranate extract 2:1, 1:1 and 4:1 (g/g) mixture administered groups as compared to each of red clover extract and pomegranate extract single formula administered groups, which serves as an evidence demonstrating that red clover:pomegranate extract mixed formula at an optimal ratio synergistically increases a liver protective effect of red clover extract and pomegranate extract, and among them, it was observed that red clover:pomegranate extract 2:1 (g/g) mixed formula showed a best liver protective effect, but the present disclosure is not limited thereto.

As a result of the experiment, remarkable increases in serum osteocalcin level and decreases in femur weight and serum bALP level were found in OVX control as compared to sham vehicle control, and indication of decreases in femur bone mass were histologically ascertained together with remarkable increases of bone resorption marker (Ocn and OS/BS), so it was observed that estrogen deficient osteoporosis was induced by OVX. On the other hand, signs of estrogen deficient osteoporosis were remarkably inhibited by administration of estradiol, red clover extract and pomegranate extract single formula, and red clover:pomegranate extract 1:1, 1:2, 1:4, 1:6, 1:8, 2:1, 4:1, 6:1 and 8:1 (g/g) mixed formula, and particularly, significant increases in effect on reduction of estrogen deficient osteoporosis were found in the order of red clover:pomegranate extract 2:1, 1:1 and 4:1 (g/g) mixture administered groups as compared to each of red clover extract and pomegranate extract single formula administered groups, which serves as an evidence demonstrating that red clover:pomegranate extract mixed formula at an optimal ratio—red clover:pomegranate extract 2:1, 1:1 and 4:1 synergistically increases an effect of red clover extract and pomegranate extract on reduction of estrogen deficient osteoporosis through increased diversity of isoflavonoids contained, and among them, it was observed that red clover:pomegranate extract 2:1 (g/g) mixed formula showed a best reduction effect for estrogen deficient osteoporosis.

As a result of the experiment, signs of menopausal disorders (obesity, hyperlipidemia, hepatic steatosis and osteoporosis) related to estrogen deficient menopause induced by OVX in ddY mice were remarkably inhibited by continuous administration of estradiol, red clover extract and pomegranate extract single formula, and all 9 types of red clover:pomegranate extract mixed formulas for 84 days, and particularly, a significant effect on reduction of menopausal disorders was provided in the order of red clover:pomegranate extract 2:1, 1:1 and 4:1 (g/g) mixture administered groups as compared to each of red clover extract and pomegranate extract single formula administered groups, so it was observed that red clover:pomegranate extract mixed formula red clover:pomegranate extract 2:1, 1:1 and 4:1 at an optimal ratio even synergistically increased a menopausal disorder reduction effect of red clover extract and pomegranate extract for OVX induced menopausal disorders through increased diversity of isoflavonoids, and among them, it was determined that red clover:pomegranate extract 2:1 mixed formula showed a best menopausal disorder alleviation effect. Accordingly, red clover:pomegranate extract 2:1 (g/g) mixture is expected to have a very high possibility of being developed as a new, more effective drug for treatment of menopausal disorders, and particularly, will be effective in reducing estrogen deficient obesity, hyperlipidemia, hepatic steatosis and osteoporosis.

What is claimed is:

1. A method for reducing a menopausal disorder, comprising: administering a composition comprising a composite of pomegranate extract and red clover extract as an active ingredient to a subject in need thereof;
   wherein the weight ratio of the pomegranate extract to the red clover extract is 1:1-4
   wherein the red clover extract comprises 50-150 mg/g of isoflavone in relation to total red clover extract, and
   wherein the composite of pomegranate extract and red clover extract comprises 30-100 mg/g of isoflavone and 0.15-0.4 mg/g of ellagic acid.

2. The method for reducing a menopausal disorder according to claim 1, wherein the menopausal disorder shows at least one menopausal symptom selected from the group consisting of facial flushing, sweating, insomnia, nervousness, depression, dizziness, poor concentration, arthralgia, headache, tachycardia, vaginal dryness, fatigue, excitement, sleeplessness, memory loss, anxiety and atherosclerosis.

3. The method for reducing a menopausal disorder according to claim 1, wherein the menopausal disorder reduction shows at least one effect selected from the group consisting of menopausal symptom relief, anti-obesity, hyperlipidemia inhibition, fatty liver inhibition, osteoporosis inhibition, liver protection and uterus protection.

4. The method according to claim 1, wherein the weight ratio of the pomegranate extract to the red clover extract is 1:2.

5. The method according to claim 1, wherein the composite of pomegranate extract and red clover extract is present in 50-150 mg per 100 ml of the composition.

6. The method according to claim 1, wherein the pomegranate extract comprises 0.5-1 mg/g of ellagic acid in relation to total pomegranate extract.

7. The method according to claim 1, wherein the red clover extract is obtained by extraction using water, lower alcohol with 1-4 carbons, or mixtures thereof as a solvent.

8. The method according to claim 1, wherein the red clover extract is a red clover extract powder.

9. The method according to claim 1, wherein the pomegranate extract is a pomegranate extract powder.

* * * * *